US007763253B2

(12) United States Patent
Hedlund et al.

(10) Patent No.: US 7,763,253 B2
(45) Date of Patent: Jul. 27, 2010

(54) TREATMENT OF HYPERPROLIFERATIVE DISEASE WITH SUPERANTIGENS IN COMBINATION WITH ANOTHER ANTICANCER AGENT

(75) Inventors: Gunnar Hedlund, Lund (SE); Göran Forsberg, Eslöv (SE); Marie Wallén-öhman, Lund (SE)

(73) Assignee: Active Biotech, AB, Lund (SE)

( * ) Notice: Subject to any disclaimer, the term of this patent is extended or adjusted under 35 U.S.C. 154(b) by 0 days.

(21) Appl. No.: 11/202,507

(22) Filed: Aug. 12, 2005

(65) Prior Publication Data

US 2006/0057111 A1 Mar. 16, 2006

Related U.S. Application Data

(60) Provisional application No. 60/601,548, filed on Aug. 13, 2004.

(30) Foreign Application Priority Data

Aug. 17, 2004 (SE) .................................... 0402025

(51) Int. Cl.
*A61K 39/00* (2006.01)
(52) U.S. Cl. .................................................. 424/185.1
(58) Field of Classification Search ..................... None
See application file for complete search history.

(56) References Cited

U.S. PATENT DOCUMENTS

| 5,194,596 | A | 3/1993 | Tischer et al. |
| 5,350,836 | A | 9/1994 | Kopchick et al. |
| 5,858,363 | A | 1/1999 | Dohlsten et al. |
| 6,126,945 | A | 10/2000 | Terman et al. |
| 6,187,908 | B1 | 2/2001 | Terrett et al. |
| 6,197,299 | B1 | 3/2001 | Dohlsten et al. |
| 6,221,351 | B1 | 4/2001 | Terman |
| 6,399,332 | B1 | 6/2002 | Ulrich et al. |
| 6,514,498 | B1 | 2/2003 | Antonsson et al. |
| 6,692,746 | B1 | 2/2004 | Terman et al. |
| 6,962,694 | B1 | 11/2005 | Soegaard et al. |
| 7,125,554 | B2 * | 10/2006 | Forsberg et al. ........... 424/183.1 |
| 7,179,625 | B2 | 2/2007 | Han et al. |
| 7,220,724 | B2 | 5/2007 | Markland, Jr. et al. |
| 7,226,595 | B2 | 6/2007 | Antonsson et al. |
| 7,226,601 | B1 | 6/2007 | Abrahmsen et al. |
| 2002/0177551 | A1 | 11/2002 | Terman |
| 2005/0226885 | A1 | 10/2005 | Soegaard et al. |
| 2005/0260215 | A1 | 11/2005 | Abrahmsen et al. |
| 2006/0052295 | A1 | 3/2006 | Terman |
| 2006/0062795 | A1 | 3/2006 | Abrahmsen et al. |
| 2007/0082001 | A1 | 4/2007 | Forsberg et al. |

FOREIGN PATENT DOCUMENTS

| DE | 102 10 312 A1 | 12/2003 |
| WO | WO 93/24136 A | 12/1993 |
| WO | WO 01/14884 A | 3/2001 |
| WO | WO 03/094846 A2 * | 11/2003 |
| WO | WO 2006/015882 A3 | 2/2006 |

OTHER PUBLICATIONS

Forsberg et al (The Journal of Biological Chemistry, May 1997, 272(19):12430-12346).*
French and Robson, "What is a Conserved Substitution?" J. Mol. Evol. 19: 171-175 (1983).
Landunga and Smith, "Amino acid substitutions preserve protein folding by conserving steric and hydrophobibicy properties." Prot. Eng'r . 10: 187-196 (1997).
International Search Report; International Application No. PCT/EP2005/008815; Feb. 6, 2007.
Bertram et al., "Staphylococcal Protein A Column: Correlation of Mitogenicity of Perfused Plasma With Clinical Response," Cancer Res. Sep. 1985;45(9):4486-94.
Céspedes, "Mouse Models in Oncogenesis and Cancer Therapy," Clin Transl Oncol. May 2006;8(5):318-29.
Cooper et al., "Substances That Can Trigger Activation of the Alternative Pathway of Complement Have Anti-Melanoma Activity in Mice," Int J Cancer. May 15, 1984;33(5):683-7.
Das et al., "Mechanisms of Protein a Superantigen-Induced Signal Transduction for Proliferation of Mouse B Cell," Immunol Lett. Oct. 1, 1999;70(1):43-51.
Das, "Dissociation Between Murine Spleen Cell Mitogenic Activity of Enterotoxin Contaminants and Anti-Tumor Activity of Staphylococcal Protein A," J Immunol. Apr. 15, 1989;142(8):2943-8.
Declaration of Dr. Eugene Spier, Jan. 29, 2002, in prosecution of USSN 669274 and EP Patent 6692746.
Declaration of Dr. Saleem Kahn Sep. 18, 1995, in prosecution of US patent 6126945 and EP Patent 1103268.
Declaration of Professor Howard Grey Aug. 28, 2002, with exhibits A-D in prosecution of EP Patent 1129717.
Declaration of Professor Howard Grey, Sep. 25, 2003, and Attachments A1-A26 in prosecution of EP Patent 1129717.
Declaration of Professor William R. Pearson, Jan. 30, 2002, in prosecution of US Patent 6692746 and EP Patent 1129717.
Dennis, "Cancer: Off by a Whisker," Nature. Aug. 17, 2006;442(7104):739-41. No abstract available.

(Continued)

*Primary Examiner*—Sean E Aeder
(74) *Attorney, Agent, or Firm*—Osha • Liang LLP

(57) ABSTRACT

The present invention relates to methods of treating mammals affected by, for example, a hyperproliferative disease such as cancer, by administering a tumor-targeted superantigen and a chemotherapeutic agent, whereby the administration of the tumor-targeted superantigen and chemotherapeutic agent reduce the antibody response and enhance the T cell response. The superantigen, wild-type or modified, is fused to a target-seeking moiety, such as an antibody or an antibody active fragment. The combined administration of a superantigen and a chemotherapeutic agent provides enhanced therapeutic effects in a treated animal.

57 Claims, 13 Drawing Sheets

OTHER PUBLICATIONS

Dohlsten et al., "Human Major Histocompatibility Complex Class II-Negative Colon Carcinoma Cells Present Staphylococcal Superantigens to Cytotoxic T Lymphocytes: Evidence for a Novel Enterotoxin Receptor," Eur J Immunol. May 1991;21(5):1229-33.

Fraser, "Superantigens—Powerful Modifiers of the Immune System," Mol Med Today. Mar. 2000;6(3):125-32.

Gattinoni et al. "Removal of Homeostatic Cytokine Sinks by Lymphodepletion Enhances the Efficacy of Adoptively Transferred Tumor-Specific CD8+ T Cells," J Exp Med. Oct. 3, 2005;202(7):907-12.

Lipman et al, "Rapid and Sensitive Protein Similarity Searches," Science. Mar. 22, 1985;227(4693):1435-41.

Nakanishi et al., "Plasma Therapy of Primary Rat Mammary Carcinoma: Dependence of Consumption of C3 During Absorption of Plasma With Sepharose Derivatives on the Anticoagulant," Cancer Res. Sep. 1985;45(9):4122-7.

Pearson et al., "Improved Tools for Biological Sequence Comparison," Proc Natl Acad Sci U S A. Apr. 1988;85(8):2444-8. J Exp Med. Oct. 3, 2005;202(7):907-12.

Rosendahl et al., T-Cell Cytotoxicity Assays for Studying the Functional Interaction Between the Superantigen Staphylococcal Enterotoxin A and T-Cell Receptors, Methods Mol Biol. 2000;145:241-57. (Bacterial Toxins: Methods and Protocols Edited by O. Hoist, Human Press Inc., Totowa, NJ, 1993).

Shearer et al., "[(Igg)2 Protein A]2 Complex Stimulates Cytosine Arabinoside Incorporation Into DNA and Inhibits L Cell Proliferation," Immunopharmacology. Oct. 1984;8(2):103-10.

Shearer et al., "IgG-Protein A Complexes Modulate Thymidine Incorporation Into DNA of Antibody and Complement-Stimulated Cells," J Immunol. May 1984;132(5):2279-84.

Stedman's Medical Dictionary definition of "Parentral" 27th edition, Lippincott Williams & Wilkins, p. 1316.

Sukumar et al.," Plasma Therapy of Primary Rat Mammary Carcinoma: Antitumor Activity of Tumor-Bearer Plasma Adsorbed Against Inactivated Cnbr Sepharose or Protein A-Sepharose," J Biol Response Mod. 1984;3(3):303-15.

Talmadge et al., "Murine Models to Evaluate Novel and Conventional Therapeutic Strategies for Cancer," Am J Pathol. Mar. 2007;170(3):793-804.

Office Action Summary issued Oct. 23, 2008 during the prosecution of U.S. Appl. No. 10/513,466; 24 pages.

Office Action Summary issued Mar. 7, 2007 during the prosecution of U.S. Appl. No. 10/513,466; 30 pages.

Office Action Summary issued Jun. 2, 2009 during the prosecution of U.S. Appl. No. 10/513,466; 36 pages.

Office Action Summary issued Nov. 29, 2007 during the prosecution of U.S. Appl. No. 10/513,466; 26 pages.

Amendment/Req. Reconsideration-After Non-Final Reject issued Mar. 4, 2009; during the prosecution of U.S. Appl. No. 10/513,466, with enclosures.

Notice to the applicant regarding a non-compliant or non-responsive amendment; issued Feb. 26, 2009, with enclosures.

Informal or Non-Responsive Amendment; issued Jan. 20, 2009; during the prosecution of U.S. Appl. No. 10/513,466, with enclosures.

Amendment/Req. Reconsideration-After Non-Final Reject; issued May 27, 2008 during the prosecution of U.S. Appl. No. 10/513,466, with enclosures.

Notice to the applicant regarding a non-compliant or non-responsive amendment; issued Mar. 13, 2008 during the prosecution of U.S. Appl. No. 10/513,466.

Request for Continued Examination (RCE); dated Feb. 26, 2008 filed during the prosecution of U.S. Appl. No. 10/513,466, with enclosures.

Amendment Submitted/Entered with Filing of CPA/RCE; dated Feb. 26, 2008; filed during the prosecution of U.S. Appl. No. 10/513,466, with enclosures.

Amendment/Req. Reconsideration-After Non-Final Reject; dated Sep. 7, 2007; filed during the prosecution of U.S. Appl. No. 10/513,466, with enclosures.

Preliminary Amendment; dated Apr. 4, 2006; filed during the prosecution of U.S. Appl. No. 10/513,466, with enclosures.

Preliminary Amendment; dated Nov. 8, 2004; filed during the prosecution of U.S. Appl. No. 10/513,466, with enclosures.

Interview Summary issued Jun. 22, 2009, in the prosecution of related U.S. Appl. No. 10/513,466 (4 pages).

Information Disclosure Statement filed Aug. 5, 2009, in the prosecution of related U.S. Appl. No. 10/513,466 (5 pages).

RCE and Amendment filed Aug. 7, 2009, in the prosecution of related U.S. Appl. No. 10/513,466 (21 pages).

RCE and Amendment filed Aug. 1, 2009, in the prosecution of related U.S. Appl. No. 10/513,466 (21 pages).

Information Disclosure Statement Review issued Nov. 2, 2009, in the prosecution of related U.S. Appl. No. 10/513,466 (3 pages).

Office Action issued Nov. 2, 2009, in the prosecution of related U.S. Appl. No. 10/513,466 (34 pages).

Interview Summary issued Nov. 16, 2009, in the prosecution of related U.S. Appl. No. 10/513,466 (3 pages).

Amendment filed Dec. 4, 2009, in the prosecution of related U.S. Appl. No. 10/513,466 (25 pages).

Information Disclosure Statement filed Dec. 4, 2009, in the prosecution of related U.S. Appl. No. 10/513,466 (6 pages).

Later Publication of International Search Report issused Apr. 19, 2007, in International Application No. PCT/EP2005/008815 (6 pages).

International Preliminary Report on Patentability Chapter II issued Jul. 4, 2007, in International Application No. PCT/EP2005/008815 (5 pages).

Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol. Nov. 1990;111(5 Pt 1):2129-38.

Chen, "Novel cancer vaccines: an update," Expert Opinion on Therapeutic Patents, vol. 13(12), Dec. 1, 2003 , pp. 1787-1799.

Cheng et al., "Individualized patient dosing in phase I clinical trials: the role of escalation with overdose control in PNU-214936," J Clin Oncol. Feb. 15, 2004;22(4):602-9.

Das et al., "Mechanisms of protein A superantigen-induced signal transduction for proliferation of mouse B cell," Immunol Lett. Oct. 1, 1999;70(1):43-51.

Doerks et al., "Protein annotation: detective work for function prediction," Trends Genet. Jun. 1998;14(6):248-50.

Dohlsten et al., "Human major histocompatibility complex class II-negative colon carcinoma cells present staphylococcal superantigens to cytotoxic T lymphocytes: evidence for a novel enterotoxin receptor," Eur J Immunol. May 1991;21(5):1229-33.

Dray et. al., "Cyclophosphamide and melphalan as immunopotentiating agents in cancer therapy", Med Oncol Tumor Pharmacother. 1989 ;6 (1):77-85.

Erlandsson et al., "Identification of the antigenic epitopes in staphylococcal enterotoxins A and E and design of a superantigen for human cancer therapy," J Mol Biol. Nov. 7, 2003;333(5):893-905.

Forsberg et al, "Therapy of human non-small-cell lung carcinoma using antibody targeting of a modified superantigen," Br J Cancer. Jul. 6, 2001;85(1):129-36.

Fraser, "Superantigens—powerful modifiers of the immune system," Mol Med Today. Mar. 2000;6(3):125-32.

Hedlund et al., "Superantigen-based tumor therapy: in vivo activation of cytotoxic T cells," Cancer Immunol Immunother. 1993;36(2):89-93.

Imanishi et al., "Activation of murine T cells by streptococcal pyrogenic exotoxin type A. Requirement for MHC class II molecules on accessory cells and identification of V beta elements in T cell receptor of toxin-reactive T cells," J Immunol. Nov. 15, 1990;145(10):3170-6.

Keck et al., "Vascular permeability factor, an endothelial cell mitogen related to PDGF," Science. Dec. 8, 1989;246(4935):1309-12.

Lamphear et al., "Intercellular adhesion molecule-1 and leukocyte function-associated antigen-3 provide costimulation for superantigen-induced T lymphocyte proliferation in the absence of a specific presenting molecule,"J Immunol. Jan. 15, 1998;160(2):615-23.

Lavoie et al., "Understanding the mechanism of action of bacterial superantigens from a decade of research", Immunol Rev. Apr. 1999;168:257-69.

Lazar et al., "Transforming growth factor alpha: mutation of aspartic acid 47 and leucine 48 results in different biological activities," Mol Cell Biol. Mar. 1988;8(3):1247-52.

Le Poole, "Recent progress in tumour vaccine development" Expert Opin Investig Drugs. Jun. 2003;12(6):971-81.

Massague, "The TGF-beta family of growth and differentiation factors," Cell. May 22, 1987;49(4):437-8.

Merino et al, "Treatment strategies for solid tumors and implications on host defense," in Wingard JR and Bowden RA eds. *Management of Infection in Oncology Patients* p. 3-15 Taylor and Trancis, Independence KY (2003).

Mokyr et al., "Interplay between the toxic effects of. anticancer drugs and host antitumor immunity in cancer therapy", Cancer Invest 5: 31-38, 1987.

Mondal et al., "Repeated treatment with *S. aureus* superantigens expands the survival rate of ehrlich ascites tumor bearing mice", Immunological investigations, 2002, vol. 31, No. 1, pp. 13-28.

Mondal et al., "Superantigen-induced apoptotic death of tumor cells is mediated by cytotoxic lymphocytes, cytokines, and nitric oxide", Biochem Biophys Res Commun, 2002, 290:1336-1342.

Papageorgiou et al., "Structural basis for the recognition of superantigen streptococcal pyrogenic exotoxin A (SpeA1) by MHC class II molecules and T-cell receptors," EMBO J. Jan. 4, 1999;18(1):9-21.

Perabo, "Preclinical evaluation of superantigen (staphylococcal enterotoxin B) in the intravesical immunotherapy of superficial bladder cancer": Int J Cancer. Jul. 1, 2005;115(4):591-8.

Pilbeam et al., "Comparison of the effects of various lengths of synthetic human parathyroid hormone-related peptide (hPTHrP) of malignancy on bone resorption and formation in organ culture," Bone. Sep.-Oct. 1993;14(5):717-20.

Plautz et al., "Defining the synergistic effects of irradiation and T-cell immunotherapy for murine intracranial tumors", Cell. Immunol., 171: 277-284, 1996.

Pulaski et al., "Cooperativity of *Staphylococcal aureus* enterotoxin B superantigen, major histocompatibility complex class II, and CD80 for immunotherapy of advanced spontaneous metastases in a clinically relevant postoperative mouse breast cancer model," Cancer Res. May 15, 2000;60(10):2710-5.

Reid et al., "The bispecific antibody 500A2×96.5 targets T-lymphocytes activated in vivo with staphylococcal enterotoxin B (SEB) against CL62 melanoma cells in vitro", Surg Oncol. Oct. 1994;3(5):279-85.a.

Rosendahl et al., "Repeated treatment with antibody-targeted superantigens strongly inhibits tumor growth", Int J Cancer. Apr. 13, 1998;76(2):274-83.

Rosendahl et al., T-cell cytotoxicity assays for studying the functional interaction between the superantigen staphylococcal enterotoxin A and T-cell receptors, Methods Mol Biol. 2000;145:241-57.

Rubin et al., "Cooperation between staphylococcal enterotoxin B and low dose melphalan in the cure of mice bearing a large MOPC-315 tumor and extensive metastases", The Journal of immunology, 1994, vol. 152, No. 7, pp. 3522-3529.

Shaw et al., "A phase II study of a 5T4 oncofoetal antigen tumour-targeted superantigen (ABR-214936) therapy in patients with advanced renal cell carcinoma," Br J Cancer. Feb. 26, 2007;96(4):567-74. Epub Feb. 6, 2007.

Skolnick et al., From genes to protein structure and function: novel applications of computational approaches in the genomic era.Trends Biotechnol. Jan. 2000;18 vol. (1):34-9.

Smith et al., "The challenges of genome sequence annotation or The devil is in the details," Nat Biotechnol. Nov. 1997;15(12):1222-3.

Stedman's Medical Dictionary definition of "parentra.1" 27th edition, Lippincott Williams & Wilkins, p. 1316, 2006.

Sundberg et al., "So many ways of getting in the way: diversity in the molecular architecture of superantigen-dependent T-cell signaling complexes," Curr Opin Immunol. Feb. 2002;14(1):36-44. Review.

Sundstrom et al., "Hypofractionated palliative radiotherapy (17 Gy per two fractions) in advanced non-small-cell lung carcinoma is comparable to standard fractionation for symptom control and survival: a national phase III trial," J Clin Oncol. Mar. 1, 2004;22(5):801-810.

Takemura et al., "A mutated superantigen SEA D227A fusion diabody specific to MUC1 and CD3 in targeted cancer immunotherapy for bile duct carcinoma," Cancer Immunol Immunother. Mar. 2002; Epub 2002 Jan. 11, 2002; vol. 51(1):33-44.

Terman et al., "Staphylococcal superantigens of the enterotoxin gene cluster (egc) for treatment of stage IIIb non-small cell lung cancer with pleural effusion," Clin Chest Med. Jun. 2006;27(2):321-34.

Terman et al., "Tumoricidal response induced by cytosine arabinoside after plasma perfusion over protein A," Science. Sep. 12, 1980;209(4462):1257-9.

Tester, "Innovative treatments for non-small cell lung cancer," Expert Opin Investig Drugs. Jun. 2001;10(6):1021-32.

Vukicevic et al., "Induction of nephrogenic mesenchyme by osteogenic protein 1 (bone morphogenetic protein 7)." Proc Natl Acad Sci U S A. Aug. 20, 1996;93(17):9021-6.

Supplemental Declaration of Professor Howard Grey Aug. 28, 2002, with exhibits A-D in prosecution of EP Patent 1129717.

Supplemental Declaration of Professor Howard Grey, Sep. 25, 2003, and Attachments A1-A26 in prosecution of EP Patent 1129717.

Supplemental Declaration of Professor William R. Pearson, Jan. 30, 2002, in prosecution of US Patent 6692746 and EP Patent 1129717.

Supplemental Declaration of Dr. Eugene Spier, Jan. 29, 2002, in prosecution of USSN 669274 and EP Patent 6692746.

Supplemental Declaration of Dr. Saleem Kahn Sep. 18, 1995, in prosecution of US patent 6126945 and EP Patent 1103268.

Alpaugh et al., "Superantigen-targeted therapy: Phase I escalating repeat dose trial of the fusion protein PNU-214565 in patients with advanced gastrointestinal malignancies", Clin Cancer Res 1998. vol. (4): 1903-1914.

Antonnson et al., "Functional characterization of the interaction between the superantigen staphylococcal enterotoxin A and the TCR," J Immunol. May 1, 1997;158(9):4245-4251.

Belka et al., "Impact of localized radiotherapy on blood immune cells counts and function in humans," Radiother Oncol. Feb. 1999;50(2):199-204.

Benjamin et al., "A plasticity window for blood vessel remodelling is defined by pericyte coverage of the preformed endothelial network and is regulated by PDGF-B and VEGF," Development. May 1998;125(9):1591-8.

Bork, "Go hunting in sequence databases but watch out for the traps," Trends Genet. Oct. 1996;12(10):425-7.

Bork, "Powers and pitfalls in sequence analysis: the 70% hurdle," Genome Res. Apr. 2000;10(4):398-400.

Bowie et al., "Deciphering the message in protein sequences: tolerance to amino acid substitutions," Science. Mar. 16, 1990;247(4948):1306-10.

Brenner, "Errors in genome annotation," Trends Genet. Apr. 1999;15(4):132-3.

* cited by examiner

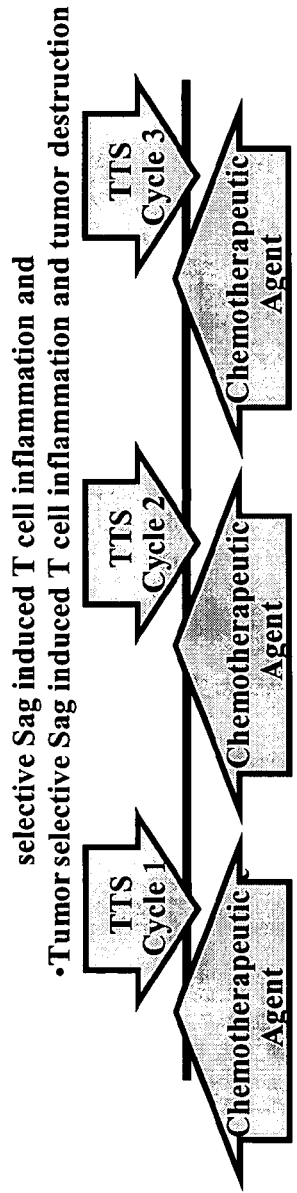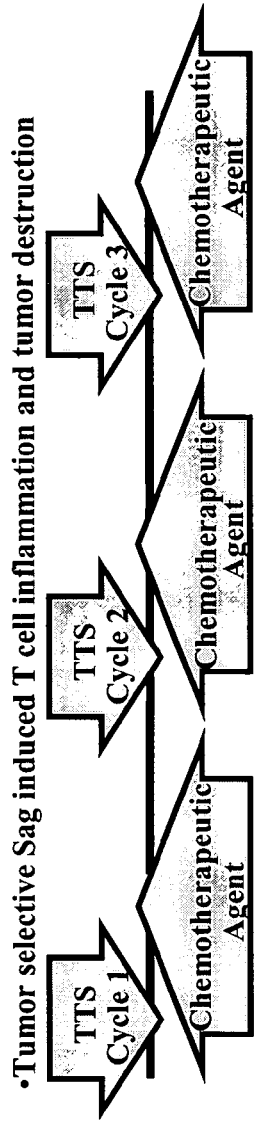
FIG. 1

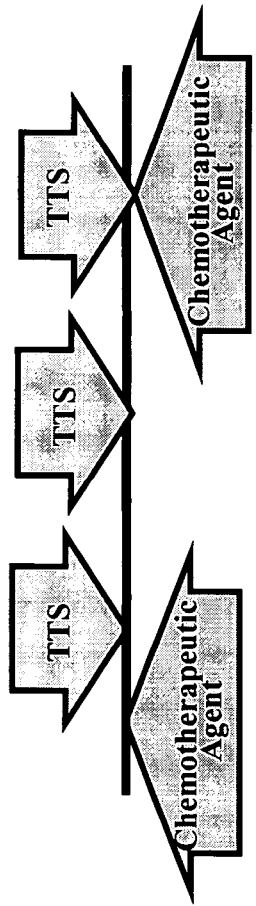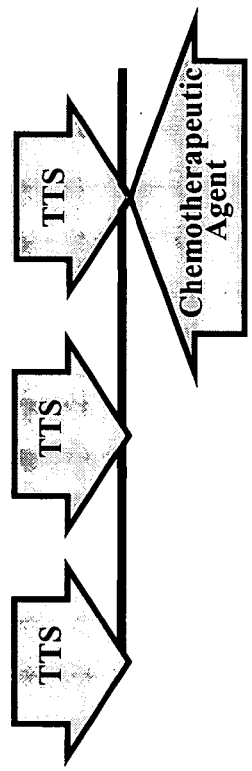
FIG. 1

```
                                   A                        B
SEA/E-120    SEKSEEINEKDLRKKSELQGTALGNLKQIYYYNSKAITSSEKSADQFLTNTLLFKGFFTG 60
SEE          SEKSEEINEKDLRKKSELQRNALSNLRQIYYYNEKAITENKESDDQFLENTLLFKGFFTG 60
SEA          SEKSEEINEKDLRKKSELQGTALGNLKQIYYYNEKAKTENKESHDQFLQHTILFKGFFTD 60
             ****************** .**.**:******.** *..::* **** :*:*******.
                           C
SEA/E-120    HPWYNDLLVDLGSTAATSEYEGSSVDLYGAYYGYQCAGGTPNKTACMYGGVTLHDNNRLT 120
SEE          HPWYNDLLVDLGSKDATNKYKGKKVDLYGAYYGYQCAGGTPNKTACMYGGVTLHDNNRLT 120
SEA          HSWYNDLLVDFDSKDIVDKYKGKKVDLYGAYYGYQCAGGTPNKTACMYGGVTLHDNNRLT 120
             *.********:.*.   ..:*:*..***********************************

SEA/E-120    EEKKVPINLWIDGKQTTVPIDKVKTSKKEVTVQELDLQARHYLHGKFGLYNSDSFGGKVQ 180
SEE          EEKKVPINLWIDGKQTTVPIDKVKTSKKEVTVQELDLQARHYLHGKFGLYNSDSFGGKVQ 180
SEA          EEKKVPINLWLDGKQNTVPLETVKTNKKNVTVQELDLQARRYLQEKYNLYNSDVFDGKVQ 180
             **********:****.***::.***.**:***********:**: *:.***** *.****
                  D                                      E
SEA/E-120    RGLIVFHSSEGSTVSYDLFDAQGQYPDTLLRIYRDNTTISSTSLSISLYLYTT 233
SEE          RGLIVFHSSEGSTVSYDLFDAQGQYPDTLLRIYRDNKTINSENLHIDLYLYTT 233
SEA          RGLIVFHTSTEPSVNYDLFGAQGQYSNTLLRIYRDNKTINSENMHIDIYLYTS 233
             *******:*   .:*.****.*****.:*********.**.*  .: * :****:
```

TREATMENT OF HYPERPROLIFERATIVE DISEASE WITH SUPERANTIGENS IN COMBINATION WITH ANOTHER ANTICANCER AGENT

CROSS-REFERENCE TO RELATED APPLICATIONS

This application is claims priority to U.S. Provisional Patent Application No. 60/601,548, filed Aug. 13, 2004, which is also incorporated herein by reference in its entirety, and to Swedish Patent Application Number SE 0402025-1, filed Aug. 17, 2004.

This application is also related to the following U.S. patents and patent applications, each of which are incorporated herein by reference in their entirety: U.S. Pat. Nos. 5,858,363, 6,197,299, 6,514,498, 6,926,694, 7,125,554, 7,226,595, and 7,226,601.

TECHNICAL FIELD

The present invention relates to methods of treating mammals, for example humans, by administering a superantigen and an anticancer agent. More particularly, the invention relates to the administration of a superantigen and an anticancer agent for the treatment of a hyperproliferative disease, for example, cancer. Still more particularly, the present invention relates to the administration of an anticancer agent, such as a chemotherapy drug, in sequenced dosage with a bacterial superantigen, such as a tumor-targeted superantigen ("TTS"), in the treatment of cancer, whereby the administration results in a synergistic effect compared to the administration of each agent alone. Still further, the present invention relates to a method of administering a superantigen, such as tumor-targeted superantigen and an anticancer agent, such as a cytostatic chemotherapeutic, whereby the administration reduces the production of antibodies to the superantigen in the treated host, compared with the administration of superantigen alone. Embodiments of the present invention also relates to kits containing a superantigen, such as a tumor-targeted superantigen, and an anticancer agent, such as a chemotherapeutic drug.

BACKGROUND OF THE INVENTION

Developing effective treatments of malignant tumors is still a challenge, despite encouraging progress during the last decades. Today, the most commonly used treatment for advanced metastasized cancer involves the use of cytostatic drugs, sometimes one or more in combination. Cytostatic drugs affect proliferating cells by interfering with fundamental processes of cell multiplication, thereby inducing cell arrest or cell death. Targets include DNA, nucleotide metabolism, enzymes related to DNA integrity, and the cytoskeleton. A group of cytostatic drugs proven to be effective in the treatment of cancer comprises alkylating agents, antimetabolites, inhibitors of mitosis, cytostatic antibiotics, platinum based compounds and topoisomerase inhibitors.

Superantigens are bacterial, viral proteins, and now, human-engineered molecules, capable of activating T lymphocytes at picomolar concentrations. They bind directly to the major histocompatibility complex (MHC) without being processed. Superantigens bind unprocessed outside the antigen-binding groove on MHC class II molecules, thereby avoiding most of the polymorphism in the conventional peptide-binding site. Superantigens bind to the Vβ chain of the T cell receptor (TCR), instead of binding to the hypervariable loops of the T cell receptor (TCR) and activate T cells. Therefore, when a superantigen is administered to an animal, such as a human, a subset of T cells is non-specifically activated by the superantigen, as opposed to administration of a "regular" antigen, which would specifically activate only a small subset of T cells. Examples of bacterial superantigens include, but are not limited to, Staphylococcal enterotoxin (SE), *Streptococcus pyogenes* exotoxin (SPE), *Staphylococcus aureus* toxic shock-syndrome toxin (TSST-1), Streptococcal mitogenic exotoxin (SME), Streptococcal superantigen (SSA), Staphylococcal enterotoxin A (SEA), and Staphylococcal enterotoxin E (SEE).

As discussed in more detail below, and in the U.S. patent applications and patents noted and incorporated herein by reference, superantigens can be modified, for example, by modifying the DNA sequences encoding superantigens, such that, for example, they encode modified superantigens having improved therapeutic properties. For example, modified superantigens can have reduced binding to MHC class II antigens compared to unmodified wild-type superantigens, resulting in reduced systemic toxicity, and/or can have reduced seroreactivity and/or decreased ability to induce an antibody response compared to the wild-type superantigens, resulting in reduced encounters with, and potential difficulties with, host antibodies. An example of a modified superantigen is SEA/E (e.g., SEA/E-120), described in detail below, which binds to MHC class II antigens to activate T cells (e.g., like that of wild-type SEA), and has reduced seroreactivity (e.g., lower than wild-type SEE).

In some embodiments of the present invention, a targeting moiety, for example an antibody or antibody fragment, may be conjugated to a superantigen (wild-type or modified), providing a targeted superantigen. If the antibody, or antibody fragment recognizes a tumor-associated antigen, the targeted superantigen may be called a tumor-targeted superantigen ("TTS"). Targeted superantigens retain the ability to activate large number of T lymphocytes, and add the ability to direct the activated lymphocytes to cells bearing the target moiety. For example, TTS molecules activate large numbers of T cells and direct them to tissues containing the tumor-associate antigen that is recognized by the targeting moiety. By doing so, specific target cells can be killed, leaving the rest of the body relatively unharmed. Such "magic bullet" therapy is quite desired in the art, as non-specific anticancer agents, such as radiation, and cytostatic and cytotoxic chemotherapeutic drugs, are nonspecific and kill large numbers of cells that are not associated with tumors to be treated. For example, studies with TTS have show that inflammation by cytotoxic T lymphocytes (CTLs) into tumor tissue increases rapidly in response to the first injection of a targeted superantigen (Dohlsten et al., 1995). This inflammation with infiltration of CTLs into the tumor is one of the major effectors of the anti-tumor therapeutic of targeted superantigens.

Anticancer agents, such as cytostatic drugs and radiation, generally work by affecting or preventing cell division. Because they are nonspecific, for example, all dividing cells in a treated animal, such as a human, are affected. This typically results in extreme adverse side effects from chemotherapy treatment, such as gastrological disturbances, loss of hair, and damage to the immune system, that are notoriously well-known, both to those skilled in the art as well as to the population as a whole.

Many aspects of the immune system is characterized by dividing cells. For example, in an immune response, the requisite immunocyte expansion phase is characterized by immune cell proliferation. This proliferation is fundamental and essential to a productive immune response. Since cytostatic agents affect dividing cells, cytostatic agents are known to be deleterious to the immune system. In fact, a compromised immune system is one of the more common and serious side effects of treating cancer with chemotherapeutic drugs.

On the other hand, immune therapy relies on a functional immune system. (Chen 2003; Le Poole et al., 2003). Immune therapies such as tumor vaccines rely on a functional immune response in a treated patient. For example, for a productive immune response to a tumor vaccine, T and B lymphocytes must be activated, expand and differentiate into sufficient numbers of effector cells (Le Poole et al., 2003; Chen 2003). This of course requires cell division. Further, it is highly probable that such an immune response also requires that the immunocyte proliferation repeat a second time in order to reach a productive antitumor response (Tester and Mora 2001).

One skilled in the art would, therefore, not expect immune therapy to be compatible with anticancer agents such as cytostatic agents that affect cell division. Immune therapy is expected to require cell division in the immune system, and cytostatic agents are known to affect or prevent cell division.

Therefore, prior to the advent of the instant invention, it was not expected to be possible to combine immunotherapy with anticancer agents, such as cytostatic or cytocidal drugs. Applicants understand that the present invention is the first time that effective use has been made of immunotherapy in the context of anticancer treatment, such as with cytostatic or cytotoxic drugs. As explained below, the inventors have discovered that not only is immunotherapy with superantigens compatible with anticancer agents such as cytostatic drugs, but in fact, coordinating the dosing of these two agents results in synergistic anticancer results. Furthermore, this combination therapy affords the benefit of reducing the production of antibodies in a treated person to the superantigens.

BRIEF SUMMARY OF THE INVENTION

The instant invention relates to a method of treating a mammal, such as a human, with superantigens and an anticancer agent, such as a chemotherapeutic agent. The instant invention relates to the discovery that superantigen therapy and other anticancer therapies can be combined to result in synergistic treatment effects, and reduced antibody production in the treated host to superantigen therapy.

One embodiment of the present invention comprises a method of reducing an antibody response to a tumor-targeted superantigen in a mammal, comprising systemically administering to the mammal a tumor-targeted superantigen and administering a chemotherapeutic agent. The tumor-targeted superantigen is administered by an administration selected from the group consisting of administration of the tumor-targeted superantigen prior to the administration of the chemotherapeutic agent, administration of the tumor-targeted superantigen after the administration of the chemotherapeutic agent, administration of the tumor-targeted superantigen during the administration of the chemotherapeutic agent, and administration of the tumor-targeted superantigen between administration of the chemotherapeutic agent.

In certain embodiments, the tumor-targeted superantigen is selected from the group consisting of staphylococcal enterotoxin A, modified staphylococcal enterotoxin A, staphylococcal enterotoxin E, and modified staphylococcal enterotoxin E. More specifically, the tumor-targeted superantigen comprises a targeting moiety selected from the group consisting of an antibody and a fragment of an antibody. Yet further, the targeted-superantigen is selected from the group consisting of, but not limited to SEQ. ID. NO. 5, SEQ. ID. NO. 6, SEQ. ID. NO. 7, SEQ. ID. NO. 8, SEQ. ID. NO. 9, and SEQ. ID. NO. 10.

The chemotherapeutic drug can be a cytostatic drug. For example, the cytostatic drug is selected from the group consisting of, but not limited to alkylating agents, antimetabolites, inhibitors of mitosis, anti-tumor antibiotics, and platinum based compounds.

In certain embodiments, the alkylating agent is selected from the group consisting of, but not limited to busulfan, chlorambucil, cyclophosphamide, melphalan, carmustine, and lomustine.

Still further, the antimetabolite can be selected from the group consisting of, but not limited to 5-fluorouracil, gemcitabine, and pemetrexed.

More particularly, the antitumor antibiotic is selected from the group consisting of, but not limited to doxorubicin, daunorubicin, mitomycin, actinomycin D, and bleomycin.

In further embodiments, the mitotic inhibitor is selected from the group consisting of, but not limited to paclitaxel, docetaxel, vinblastine, vincristine, and etoposide.

Still further, the platimun based compound is selected from the group consisting of, but not limited to cisplatin, carboplatin, and oxaliplatin.

In certain embodiments, the mammal, for example a human, is suffering from a hyperproliferative disease, wherein the hyperproliferative disease is further defined as cancer. More particularly, the cancer is selected from the group consisting of, but not limited to lung, breast, colon, kidney, pancreatic, ovarian, stomach, cervix and prostate cancer.

Another embodiment of the present invention comprises a method for enhancing the T cell response a tumor-targeted superantigen in a mammal, comprising systemically administering to the mammal a tumor-targeted superantigen and a chemotherapeutic agent, wherein administration of the chemotherapeutic agent reduces the antibody response to the tumor-targeted superantigen. The mammal is a human.

Still further, another embodiment of the present invention comprises a method for increasing the anti-tumor effect of a chemotherapeutic agent in a mammal, comprising administering to the mammal a chemotherapeutic agent and systemically administering to the mammal a tumor-targeted superantigen. The mammal is a human.

In preferred embodiments of the present invention, the superantigen is a bacterial superantigen, and the anticancer agent is a chemotherapy drug, such that the superantigen is directed to cells or other locations that express the antigen recognized by the targeting moiety. In certain embodiments, the targeting moiety may be an antibody or an antibody fragment. In certain embodiments, the targeting moiety may be a soluble T cell receptor (TCR) (e.g., a soluble TCR) or other specific binding moiety. In certain embodiments, the superantigen may be modified, for example, by genetic engineering or other treatments, to have modified properties from wild-type superantigen, for example but not limited to, reduced MHC class II binding and/or reduced seroreactivity and/or ability to generate an antibody response.

An embodiment of the present invention is a method for treating a hyperproliferative disease in a mammal comprising the steps of administering to the mammal a therapeutically effective amount of a superantigen, such as TTS, and administering a therapeutically effective amount of an anticancer agent. In certain embodiments, the anticancer agent is a chemotherapeutic drug or agent, and/or the anticancer agent may be radiation. In preferred embodiments, the mammal is a human. In other preferred embodiments, the hyperproliferative disease is cancer. In other preferred embodiments, the anticancer agent is a chemotherapeutic drug.

Still further, in some embodiments of the present invention the chemotherapeutic drug is a cytostatic drug. In certain embodiments, the cytostatic drug may have a mechanism of action selected from the group consisting of alkylating agents (e.g., busulfan, chlorambucil, cyclophosphamide, melphalan, carmustine, and lomustine), antimetabolites (e.g., 5-fluorouracil, gemcitabine, and pemetrexed), inhibitors of mitosis (e.g., paclitaxel, docetaxel, vinblastine, vincristine, and etoposide), anti-tumor antibiotics (e.g., doxorubicin, daunorubicin, mitomycin, actinomycin D, and bleomycin), and platinum based compounds (e.g., cisplatin, carboplatin, and oxaliplatin).

In further embodiments of the present invention, the superantigen is a wild-type superantigen or a modified superantigen. The superantigen, in some embodiments of the present invention, is conjugated to at least one targeting moiety. The targeting moiety, in certain embodiments, is an antibody moiety. More particularly, the antibody moiety may be selected from the group consisting of polyclonal antibodies, monoclonal antibodies, Fv, Fab and F(ab)$_2$, single chain antibodies, nanobodies (Gibbs, 2005), and humanized antibodies. Still further, the targeting moiety is a soluble T cell receptor.

In preferred embodiments of the present invention the superantigen is derived from a bacterium or a virus. More particularly, the superantigen is staphylococcal enterotoxin E, modified staphylococcal enterotoxin E, staphylococcal enterotoxin A, or modified staphylococcal enterotoxin A. Still more particularly, the superantigen is C215Fab-SEA having the amino acid sequence of SEQ ID NO 5; 5T4Fab-SEAD227A having the amino acid sequence SEQ ID NO 6; or 5T4Fab-SEA/E-120 having the amino acid sequence of SEQ ID NO 7. Still further, the superantigen is C215Fab-SEA and is encoded by the nucleic acid sequence of SEQ ID NO 9; is 5T4Fab-SEAD227A encoded by the nucleic acid sequence SEQ ID NO 8; or is 5T4Fab-SEA/E-120 encoded by the nucleic acid sequence of SEQ ID NO 10. In some embodiments the superantigen has the amino acid sequence according to SEQ ID NO 2.

In some embodiments of the present invention the superantigen, such as TTS is encoded by a DNA sequence that has been modified so that the superantigen has reduced MHC class II binding, relative to wild-type superantigen. In some embodiments the superantigen is encoded by a DNA sequence that has been modified so that the superantigen has reduced seroreactivity compared to wild-type superantigen.

In certain embodiments of the present invention the superantigen is administered in an amount of from 0.001 to 500 µg/kg body weight of the subject.

In some embodiments the superantigen is administered prior to the administration of the anti-cancer agent. In some embodiments the superantigen is administered partially simultaneously with the administration of the anti-cancer agent. In some embodiments the superantigen is administered simultaneous with the administration of the anti-cancer angent. Further, in some embodiments of the present invention the superantigen is administered subsequent to the administration of the anticancer agent.

In some embodiments of the present invention a cytostatic drug is administered first, and a superantigen is administered when the level of the cytostatic drug drops to where it is no longer cytostatic. In some embodiments a cytostatic drug is administered first, and a superantigen is administered 0 to 6 days following the administration of the cytostatic agent. In certain embodiments of the invention, a cytostatic drug is administered first, and a superantigen is administered 12-72 hours following the administration of the cytostatic agent. In some embodiments a cytostatic drug is administered first, and a superantigen is administered 0 to 6 days after the level of the cytostatic drug drops to where it is no longer cytostatic. In some embodiments of the invention a cytostatic drug is administered first, and a superantigen is administered 0-72 hours after the level of the cytostatic drug drops to where it is no longer cytostatic. Further, in some embodiments acytostatic drug is administered first, and a superantigen is administered 12-72 hours after the level of the cytostatic drug drops to where it is no longer cytostatic.

In some embodiments of the invention a superantigen, such as TTS and an anticancer agent are administered within 0 to 6 days of each other. In some embodiments, a superantigen and an anticancer agent are administered within 0-72 hours of each other. In some cases, a superantigen an anticancer agent are administered within 3-4 months of each other. Optionally, a superantigen and an anticancer agent are administered within 1 month of each other. Further, in some instances within the scope of the present invention, a superantigen and an anticancer agent are administered within 2 weeks of each other. Still further, in some embodiments a superantigen and an anticancer agent are administered within 1 week of each other. Also, in some embodiments a superantigen and an anticancer agent are administered within 7-10 days of each other. Still further, in some cases a superantigen and an anticancer agent are administered within 0-30 days of each other. Optionally, in some embodiments a superantigen and an anticancer agent are administered within 1-10 days of each other. In other embodiments, a superantigen and an anticancer agent are administered within 0-72 hours of each other. In some embodiments a superantigen and an anticancer agent are administered within 0-24 hours of each other. In still other embodiments, a superantigen and an anticancer agent are administered within 0-12 hours of each other.

In certain preferred embodiments, a superantigen and an anticancer agent are administered in sequential dosage. In some embodiments of sequential dosage administration, a superantigen is administered first. Yet further, in some embodiments of sequential dosage administration, a anticancer agent is administered first. In some embodiments of sequential dosage administration the sequential dosage follows a pattern selected from the following, or approximations thereof, where A=superantigen and B=anticancer agent: A/B/A B/A/B B/B/A A/A/B A/B/B B/A/A A/B/B/B; B/A/B/B B/B/B/A B/B/A/B A/A/B/B A/B/A/B A/B/B/A; B/B/A/A B/A/B/A B/A/A/B A/A/A/B B/A/A/A A/B/A/A; and A/A/B/A.

In certain embodiments of sequential dosage administration, the administration of a superantigen and the administration of an anticancer agent are separated by 0-6 days. In certain embodiments of sequential dosage the administration of a superantigen and the administration of an anticancer agent are separated by 0-72 hours.

In preferred embodiments, the hyperproliferative disease is associated with the formation of tumors or other forms of localized concentrations of hyperproliferative cells.

In preferred embodiments of the present invention, the hyperproliferative disease to be treated is cancer and is selected from the group consisting of tumors of lung, breast, colon, kidney, pancreatic, ovarian, stomach, cervix and prostate cancer. In preferred embodiments, a human is treated for a cancer selected from the group consisting of lung, breast, colon, kidney, pancreatic, ovarian, stomach, cervix and prostate cancer. More preferred embodiments include the treatment of a human having tumors associated with a cancer selected from the group consisting of lung, breast, colon, kidney, pancreatic, ovarian, stomach, cervix and prostate cancer, with a superantigen that is a wild-type or modified Staphyloccal bacterial superantigen fused to a targeting moiety. In still more preferred embodiments, a human having one of the above-described cancers is treated with a superantigen selected from the group consisting of C215Fab-SEA having the amino acid sequence of SEQ ID NO 5, 5T4Fab-SEAD227A having the amino acid sequence SEQ ID NO 6, and 5T4Fab-SEA/E-120 having the amino acid sequence of SEQ ID NO 7, and an anticancer agent selected from the group consisting of gemcitabine or docetaxel.

Certain preferred embodiments of the present invention include a method for treating a mammal comprising the steps of administering to the mammal a therapeutically effective amount of a superantigen, and a therapeutically effective amount of an anticancer agent, wherein the anticancer agent reduces formation of antibodies in the mammal to the superantigen and/or targeting moiety of the TTS compared with the administration of a superantigen alone. In more preferred embodiments of this method, the mammal is a human and the supertantigen is TTS.

Additional embodiments of the instant invention include kits comprising a first container having a superantigen and a second container having an anti-cancer agent. Such kits, in some embodiments, are for the treatment of a disease of a mammal, which in preferred embodiments is a human. In more preferred embodiments, the mammal is a human and the disease treated is a cancer. In still more preferred embodiments of the kit, the superantigen is selected from the group consisting of C215Fab-SEA having the amino acid sequence of SEQ ID NO 5, 5T4Fab-SEAD227A having the amino acid sequence SEQ ID NO 6, or 5T4Fab-SEA/E-120 having the amino acid sequence of SEQ ID NO 7, and the anticancer agent is selected from the group consisting of gemcitabine or docetaxel. In still other embodiments of the kit, superantigen is C215Fab-SEA having the amino acid sequence of SEQ ID NO 5, and/or the superantigen is 5T4Fab-SEAD227A having the amino acid sequence SEQ ID NO 6 and/or the superantigen is 5T4Fab-SEA/E-120 having the amino acid sequence of SEQ ID NO 7. Still further, the kit comprises a superantigen, for example, C215Fab-SEA encoded by the nucleic acid sequence of SEQ ID NO 9; 5T4Fab-SEAD227A encoded by the nucleic acid sequence SEQ ID NO 8; or 5T4Fab-SEA/E-120 encoded by the nucleic acid sequence of SEQ ID NO 10.

The foregoing has outlined rather broadly the features and technical advantages of the present invention in order that the detailed description of the invention that follows may be better understood. Additional features and advantages of the invention will be described hereinafter which form the subject of the sentences of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended. The novel features which are believed to be characteristic of the invention, both as to its organization and method of operation, together with further objects and advantages will be better understood from the following description when considered in connection with the accompanying figures. It is to be expressly understood, however, that each of the examples and figures are provided for the purpose of illustration and description only and are not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIGS. 1A-1D show a schematic showing of exemplary embodiments of the present invention regarding administration of TTS and a chemotherapeutic agent to an animal, such as a human. FIG. 1A shows the administration of a chemotherapeutic agent prior to administration of TTS. FIG. 1B shows the administration of TTS prior to the administration of a chemotherapeutic agent. FIG. 1C shows the administration of a chemotherapeutic agent followed by administration of TTS followed by simultaneous administration of TTS and a chemotherapeutic agent. FIG. 1D shows the administration of TTS followed by administration simultaneous administration of TTS and a chemotherapeutic agent.

FIG. 3 is a comparison of SEA, SEE and SEA/E-120 superantigens.

FIG. 6A shows expansion of $CD4^+ V_\beta 3$ T cells (SEA reactive) using various concentrations of gemcitabine. FIG. 6B shows expansion of $CD4^+ V_\beta 8$ T cells (control) using various concentrations of gemcitabine. FIG. 6C shows $CD8^+ V_\beta 3$ T cells (SEA reactive) using various concentrations of gemcitabine. FIG. 6D shows $CD8^+ V_\beta 8$ T cells (control) using various concentrations of gemcitabine.

FIG. 7A shows the number of CD4+ $V_\beta 3$ T cells (SEA reactive) using various concentrations and dosing schedules of gemcitabine. FIG. 7B shows the number of CD4+ $V_\beta 8$ T cells (control) using various concentrations and dosing schedules of gemcitabine.

FIGS. 9A-9D show T-cell dynamics of splenocytes of mice treated sequentially with gemcitabine and then Fab-SEA. Mice (3 mice/group) were injected with gemcitabine (2.4 mg/mouse) every third day for four doses (days 1, 4, 7 and 10), followed by treatment with three daily injections of C215Fab-SEA (10 µg/animal), starting at different time intervals after the last gemcitabine injection. 48 hours after the last injection, spleens were removed and $V_\beta 3$ specific expansion of CD4 and CD8 cells was measured. Data points representing results from individual mice, as well as trend lines representing average values from 3 individual mice. FIG. 9B shows the number of CD4+ $V_\beta 8$ T cells (control) using various concentrations of gemcitabine. FIG. 9C shows the number of CD8+ $V_\beta 3$ T cells (SEA reactive) using various concentrations of gemcitabine. FIG. 9D shows the number of CD8+ $V_\beta 8$ T cells (control) using various concentrations of gemcitabine.

FIG. 12A shows the number of CD4+ $V_\beta 3$ T cells (SEA reactive) using various concentrations of docetaxel. FIG. 12B shows the number of CD4+ $V_\beta 8$ T cells (control) using various concentrations of docetaxel. FIG. 12C shows the number of CD8+ $V_\beta 3$ T cells (SEA reactive) using various concentrations of docetaxel. FIG. 12D shows the number of CD8+ $V_\beta 8$ T cells (control) using various concentrations of docetaxel.

DETAILED DESCRIPTION OF THE INVENTION

Figure 2:
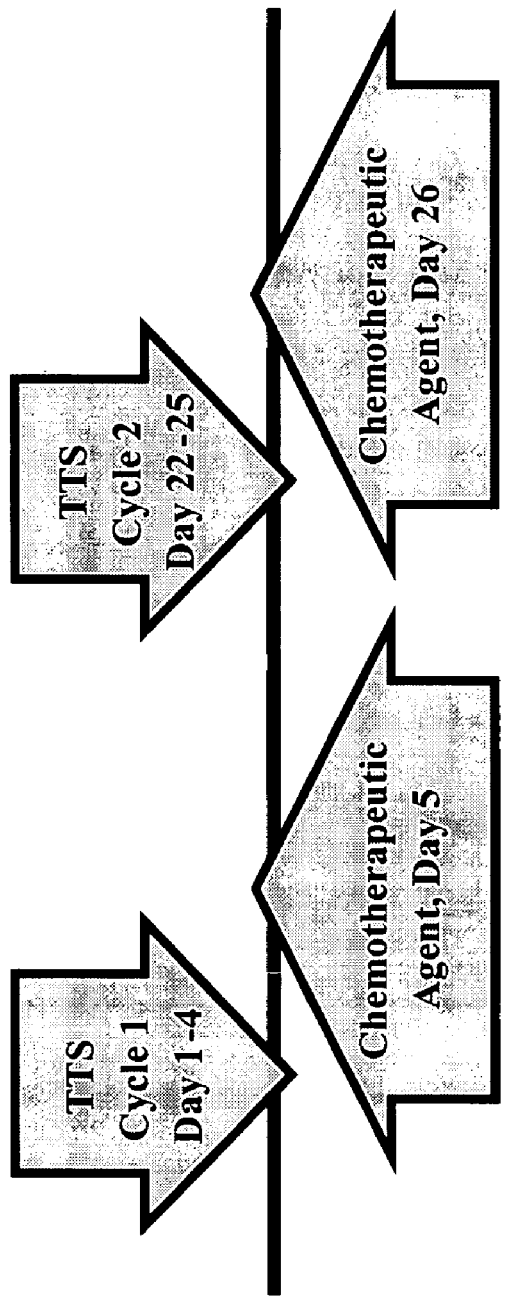
FIG. 2 a schematic showing embodiments of the present invention regarding administration of TTS and a chemotherapeutic agent to an animal, such as a human.

It is readily apparent to one skilled in the art that various embodiments and modifications may be made to the present invention without departing from the scope and spirit of the invention.

The present invention relates to methods of treating mammals, for example humans, by administering a superantigen and an anticancer agent. The inventors have discovered that combined administration of superantigens (which may be called a form of immune therapy) with anticancer agents, such as cytostatic drugs, results in enhanced anticancer effect for both agents, compared to when each agent is administered alone. Further, this combined therapy results in a reduced antibody response to the superantigen, compared to administration of the superantigen alone, which assists in treatment, especially in cases where it is desired to administer superantigens several different times throughout a course of treatment.

I. DEFINITIONS

Unless defined otherwise, technical and scientific terms used herein have the same meaning as commonly understood by one of ordinary skill in the art to which this invention belongs. For purposes of the present invention, the following terms are defined below.

As used herein the specification, "a" or "an" may mean one or more. As used herein in conjunction with the word "comprising", the words "a" or "an" may mean one or more than one. As used herein "another" may mean at least a second or more. For example, a statement such as "treatment with a superantigen and a cytostatic agent," whether in the specification or claims of this application may mean treatment: with one superantigen and one anticancer agent; with more than one superantigen and one anticancer agent; with one superantigen and more than one anticancer agent; with more than one superantigen and more than one anticancer agent; or with various other combinations thereof.

As used herein, the term "antibody" refers to an immunoglobulin molecule, which is able to specifically bind to a specific object, such as, for example, an epitope on an antigen. As used herein, an antibody is intended to refer broadly to any immunologic binding agent such as IgG, IgM, IgA, IgD and IgE, as well as synthetic and modified antibodies, as well as to antibodies from or derived from various animals, such as but not limited to, humans, mice and llamas. Antibodies can be intact immunoglobulins derived from natural sources, or from recombinant sources and can be immunoactive portions of intact immunoglobulins. The antibodies in the present invention may exist in a variety of forms including, for example, polyclonal antibodies, monoclonal antibodies, Fv, Fab and F(ab)$_2$, as well as single chain antibodies, chimeric antibodies, humanized antibodies, and fully humanized antibodies (Bird et al., 1988).

As used herein, the terms "disease," "disorder" and "condition," describe any condition or disease of a mammal, for example, but not limited to a human, and are intended to have a broad coverage, covering all types of diseases and disorders, including but not limited to cancers, neoplasms, and other types of hyperproliferative diseases and disorders.

As used herein, the terms "agent" and "drug," may be interchangeable. For example, where it is clear from the context, the terms "cytostatic agent(s)," or "anticancer agent(s)," may mean the same thing as the terms "cytostatic drug(s)," or "anticancer drug(s)," respectively.

As used herein, the terms "cancer" and "cancerous" refer to or describe the physiological condition in mammals that is typically characterized by unregulated cell growth. Examples of cancer include, but are not limited to, melanoma, carcinoma, lymphoma, blastoma, sarcoma, and leukemia or lymphoid malignancies. More particular examples of cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used herein, the term "hyperproliferative disease" is defined as a disease that results from a hyperproliferation of cells. Exemplary hyperproliferative diseases include, but are not limited to, cancer or autoimmune diseases. Examples include, but are not limited to, cancers, such as the cancer is melanoma, non-small cell lung, small-cell lung, lung, hepatocarcinoma, retinoblastoma, astrocytoma, glioblastoma, gum, tongue, leukemia, neuroblastoma, head, neck, breast, pancreatic, prostate, renal, bone, testicular, ovarian, mesothelioma, cervical, gastrointestinal, lymphoma, brain, colon, sarcoma or bladder cancer. The cancer may include a tumor comprised of tumor cells. In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

As used herein, the term "immunogen" is defined as a molecule that provokes (evokes, induces, or causes) an immune response. This immune response may involve antibody production, the activation of certain cells, such as, for example, specific immunologically-competent cells, or both. An immunogen may be derived from many types of substances, such as, but not limited to, molecules from organisms, such as, for example, proteins, subunits of proteins, killed or inactivated whole cells or lysates, synthetic molecules, and a wide variety of other agents both biological and nonbiological. Therefore, a skilled artisan realizes that any macromolecule, including virtually all proteins, can serve as immunogens. Furthermore, immunogens can be derived from recombinant DNA.

As used herein, the term "immunogenicity" is related to the ability of an immunogen to provoke (evoke, induce, or cause) an immune response. As is known in the art, different molecules may have differing degrees of immunogenicity, and a molecule having an immunogenicity that is greater compared to another molecule is known, for example, to be capable of provoking (evoking, inducing, or causing) a greater immune response than would an agent having a lower immunogenicity. As is know in the art, certain agents may have no immunogenicity.

As used herein, the term "antigen" is defined as a molecule that is recognized by antibodies, specific immunologically-competent cells, or both. An antigen may be derived from many types of substances, such as, but not limited to, molecules from organisms, such as, for example, proteins, subunits of proteins, killed or inactivated whole cells or lysates, synthetic molecules, and a wide variety of other agents both biological and nonbiological. Therefore, a skilled artisan realizes that any macromolecule, including virtually all proteins, can serve as antigens. Furthermore, antigens can be derived from recombinant DNA.

As used herein, the term "antigenicity" is related to the ability of an antigen to be recognized by antibodies, specific immunologically-competent cells, or both.

As used herein, the term "major histocompatibility complex," or "MHC," is defined as a specific cluster of genes, many of which encode evolutionarily related cell surface proteins involved in antigen presentation, that are among the most important determinants of histocompatibility. Class I MHC, or MHC-I, function mainly in antigen presentation to CD8 T lymphocytes. Class II MHC, or MHC-II, function mainly in antigen presentation to CD4 T lymphocytes.

As used herein, the term "conjugated" or "fused" means joined, and includes joining by any means, including but not limited to, by chemical means (e.g., chemical conjugation), by recombinant gene expression (e.g., a fusion protein) and by non-covalent means, permanently or non-permanently, including, but not limited to, the terms fusion or fused, and including joining one or more items, objects, molecules or the like.

As used herein, the term "derived," for example "derived from," includes, but is not limited to, for example, wild-type molecules derived from biological hosts such as bacteria, viruses and eukaryotic cells and organisms, and modified molecules, for example, modified by chemical means or produced in recombinant expression systems.

As used herein, the term "container," means any containment means whatsoever and is not limited to any particular containment means or device.

As used herein, the terms "neoplasm" or "neoplastic cells" refer to cells that multiply in an abnormal manner. Neoplasms can be classified as either benign, histoid, malignant, mixed multicentric, organoid or unicentric.

As used herein, the term "seroreactive," "seroreaction" or "seroreactivity" is defined as the ability of an agent, such as a molecule, to react with antibodies in the serum of a mammal, such as, but not limited to, a human. This includes reactions with all types of antibodies, including, for example, antibodies specific for the molecule and nonspecific antibodies that bind to the molecule, regardless of whether the antibodies inactivate or neutralize the agent. As is know in the art, different agents may have different seroreactivity relative to one another, wherein an agent having a seroreactivity lower than another would, for example, react with fewer antibodies and/or have a lower affinity and/or avidity to antibodies than would an agent having a higher seroreactivity. This may also include the ability of the agent to elicit an antibody immune response in an animan, such as a mammal, such as a human.

As used herein, the term "soluble T cell receptor," or "soluble TCR," refers to a "soluble" T cell receptor consisting of the chains of a full-length (e.g., membrane bound) receptor, except that, minimally, the transmembrane region of the receptor chains are deleted or mutated so that the receptor, when expressed by a cell, will not associate with the membrane. Typically, a soluble receptor will consist of only the extracellular domains of the chains of the wild-type receptor (e.g., lacks the transmembrane and cytoplasmic domains).

As used herein, the term "superantigen" is defined as a class of molecules that stimulate a subset of T-cells by binding to MHC class II molecules and Vβ domains of T-cell receptors, stimulating the activation of T-cells expressing particular Vβ V gene segments. This term includes wild-type and natural superantigens, for example, those isolated from certain bacteria viruses or expressed from unmodified genes from same, as well as modified superantigens, wherein, for example, the DNA sequence encoding a superantigen has been modified by genetic engineering, for example, but not limited to, to produce a fusion protein with a targeting moiety, and/or to alter certain properties of the superantigen, such as, but not limited to, its MHC class II binding (for example, to reduce affinity) and/or its seroreactivity, and/or its immunogenicity, and/or antigenicity (for example, to reduce its seroreactivity). This definition includes synthetic molecules having the properties of a superantigen as described herein. This definition includes the superantigens, including wild-type and modified, and conjugated/fused/targeted superantigens described in the following U.S. patents and patent applications, which are hereby incorporated herein by reference in their entireties: U.S. Pat. Nos. 5,858,363, 6,197,299, 6,514,498, 6,713,284, 6,692,746, 6,632,640, 6,632,441, 6,447,777, 6,399,332, 6,340,461, 6,338,845, 6,251,385, 6,221,351, 6,180,097, 6,126,945, 6,042,837, 6,713,284, 6,632,640, 6,632,441, 5,859,207, 5,728,388, 5,545,716, 5,519,114, 6,926,694, 7,125,554, 7,226,595, 7,226,601, 7,094,603, 7,087,235, 6,835,818, 7,198,398, 6,774,218, 6,913,755, 6,969,616, and 6,713,284, U.S. Patent Application Nos. 20030157113, 20030124142, 20020177551, 20020141981, 20020115190, 20020051765, 20010046501, 60/378,988, 60/389,366, 60/406,697, 60/406,750, 60/415,310, 60/415,400, and 60/438,686 and PCT International Publication Number WO/03/094846.

As used herein, the term "targeting moiety" is defined as any structure that is able to bind to a cell surface structure, preferable a disease specific structure. The targeting moiety is usually different from the Vβ chain epitope which the superantigen binds and the MHC class II epitopes to which superantigens bind. Exemplary targeting moieties comprise, but are not limited to, antibodies, antibody fragments and the like, soluble T-cell receptors, interleukins, hormones, and growth factors.

As used herein, the term "tumor-targeted superantigen" (sometimes referred to herein as "TTS") is defined as a molecule comprising one or more superantigens (as defined herein) joined, fused or conjugated with one or more targeting moieties (as defined herein). Non-limiting examples of tumor-targeted superantigens include but are not limited to, C215Fab-SEA (SEQ. ID. No. 5), 5T4Fab-SEA/E-120 (SEQ. ID. NO. 7) and 5T4Fab-SEA$_{D227A}$ (SEQ. ID. NO. 6).

As used herein, the term "T-cell receptor" is defined as receptor that is specific to T cells. This definition expressly includes the understanding of the term as known in the art, and includes, for example, a receptor that consists of a disulfide-linked heterodimer of the highly variable α or β chains expressed at the cell membrane as a complex with the invariant CD3 chains, and a receptor made up of variable γ and δ chains expressed at the cell membrane as a complex with CD3 on a subset of T-cells.

As used herein, the term "tumor" refers to a localized concentration, gathering or other organization (including but not limited to hyperproliferative cells located within a sheath (theca) or organ) of hyperproliferating (hyperproliferative) cells, including for example but not limited to neoplastic cells, whether malignant or benign, pre-cancerous and cancerous cells.

As used herein, the term "therapeutically effective" and "effective amount," is defined as the amount of the pharmaceutical composition that produces at least some effect in treating a disease or a condition. For example, in a combination according to the invention, an effective amount is the amount required to inhibit the growth of cells of a neoplasm in vivo. The effective amount of active compound(s) used to practice the present invention for therapeutic treatment of neoplasms (e.g., cancer) varies depending upon the manner of administration, the age, body weight, and general health of the subject. It is within the skill in the art for an attending physician or veterinarian to determine the appropriate amount and dosage regimen. Such amounts may be referred to as an "effective" amounts. These terms include, but are not limited to synergistic situations such as those presented and described in the instant invention wherein a single agent alone, such as a superantigen or an anticancer agent such as a chemotherapeutic drug, may act weakly or not at all, but when combined with each other, for example, but not limited to, via sequential dosage, the two or more agents act to produce a synergistic result.

As used herein, the term "inhibits the growth of a neoplasm" refers to measurably slowing, stopping, or reversing the growth rate of the neoplasm or neoplastic cells in vitro or in vivo. Desirably, the growth rate is slowed by 20%, 30%, 50%, or 70% or more, as determined using a suitable assay for determination of cell growth rates. Typically, a reversal of growth rate is accomplished by initiating or accelerating necrotic or apoptotic mechanisms of cell death in neoplastic cells, resulting in a shrinkage of a neoplasm.

As used herein, the term "variant," "variants," "modified," "altered," "mutated," and the like, refer to proteins or peptides and/or other agents and/or compounds that differ from a reference protein, peptide or other compound. Variants in this sense are described below and elsewhere in the present disclosure in greater detail. For example, changes in the nucleic acid sequence of the variant may be silent, e.g., they may not alter the amino acids encoded by the nucleic acid sequence. Where alterations are limited to silent changes of this type a variant will encode a peptide with the same amino acid sequence as the reference peptide. Changes in the nucleic acid sequence of the variant may alter the amino acid sequence of a peptide encoded by the reference nucleic acid sequence. Such nucleic acid changes may result in amino acid substitutions, additions, deletions, fusions and truncations in the peptide encoded by the reference sequence, as discussed below. Generally, differences in amino acid sequences are limited so that the sequences of the reference and the variant are closely similar overall and, in many regions, identical. A variant and reference peptide may differ in amino acid sequence by one or more substitutions, additions, deletions, fusions and truncations, which may be present in any combination. A variant may also be a fragment of a peptide of the invention that differs from a reference peptide sequence by being shorter than the reference sequence, such as by a terminal or internal deletion. Another variant of a peptide of the invention also includes a peptide which retains essentially the same function or activity as such peptide. A variant may also be but is not limited to: (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature peptide is fused with another compound, such as a compound to increase the half-life of the peptide (for example, polyethylene glycol), or (iv) one in which the additional amino acids are fused to the mature peptide, such as a leader or secretory sequence or a sequence which is employed for purification of the mature peptide. Variants may be made by mutagenesis techniques, and/or altering mechanisms such as chemical alterations, fusions, adjuncts and the like, including those applied to nucleic acids, amino acids, cells or organisms, and/or may be made by recombinant means. Variants including all of those defined above, are within the scope of those skilled in the art, for example, from the teachings herein and from the art.

As used herein, the terms "chemotherapy," "chemotherapeutic," "chemotherapeutic drug or agent," "anti-cancer drug or agent," "antiproliferative agent or drug," "cytotoxic agent or drug," "cytocidal agent or drug," and "cytostatic agent or drug," include anything, that alone or in combination that has any affect on a hyperproliferative disease or condition in a mammal, such as a human. These terms include, but are not limited to, chemical, biological, and physical agents that act directly on (e.g., affects) a hyperproliferative cell (e.g., cancer or tumor) or the vascularization of a hyperproliferation. In this context, the term "agent" includes, but is not limited to a drug. Chemotherapeutic agents (e.g., drugs) include, but are not limited to, cytostatic agents, cytotoxic (cytocidal) agents, and anti-angiogenesis agents. The terms "chemotherapy," "chemotherapeutic," "chemotherapeutic drug or agent," "anti-cancer drug or agent," "antiproliferative agent or drug," "cytotoxic agent or drug," "cytocidal agent or drug," and "cytostatic agent or drug," as used herein, do not include immune modulators (agents that act by modulating the immune system (other than by cytotoxic or cytostatic action) such as interleukin-2 (IL-2) and linomide.

As used herein, the term "sequential dosage" and related terminology refers to the administration of at least one superantigen, with at least one anticancer agent, for example, but not limited to, a chemotherapeutic drug. This definition includes staggered doses of these agents (i.e., time-staggered) and variations in dosage amounts. This includes one agent being administered before, overlapping with (partially or totally), or after administration of another agent. This term generally considers the best administration scheme to achieve a synergistic combination of at least one superantigen and at least one anticancer agent and/or to achieve administration of at least one superantigen while limiting or eliminating the generation of an antibody response to the superantigen. Determining sequential dosage administration plans is within the skill on one skilled in the art, from the background skill and teaching in the art and the teaching of this application. In certain embodiments, for example, one skilled in the art will recognize that sequential dosing, for example, with a superantigen and a cytostatic agent, depends on the half-life of the cytostatic drug. For example, as explained in detail below, dosing of a cytostatic drug and a superantigen, such as a TTS, may be calculated by first administering a cytostatic agent, then administering TTS at a pre-determined time after the cytostatic agent, the time calculated to be when the concentration of the cytostatic agent falls below a functional level. By such a dosing strategy (i.e., a sequential dosage), one can achieve synergistic effects of combined superantigen and cytostatic agent administration. Such a sequenced dosage can also reduce the formation of antibodies against the superantigen in a treated patient compared with, for example, administration of superantigen alone, resulting in fewer anti-superantigen antibodies in a patient treated with such a sequential dosage.

As used herein, the terms "systemic" and "systemically" refer to administration of an agent such that the agent is exposed to at least one system associated with the whole body, such as but not limited to the circulatory system, immune system, and lymphatic system, rather than only to a localized part of the body, such as but not limited to within a tumor. Thus, for example, a systemic therapy or an agent administered systematically is a therapy or an agent in which at least one system associated with the entire body is exposed to the therapy or agent, as opposed to, rather than just a target tissue.

As used herein, the term "parenteral administration" includes any form of administration in which the compound is absorbed into the subject without involving absorption via the intestines. Exemplary parenteral administrations that are used in the present invention include, but are not limited to intramuscular, intravenous, intraperitoneal, or intraarticular administration.

II. THE PRESENT INVENTION

FIG. 1 shows a schematic of an embodiment of the present invention. For example, one or more treatments of TTS are followed directly by one or more treatments of a chemotherapeutic agent, such as a cytostatic agent. In the present invention it has, for example, been unexpectedly discovered that administration, such as systemic administration, of a chemotherapeutic agent, such as a cytotoxic or cytostatic agent, for example shortly following administration of TTS enhances, for example synergistically, the anti-tumor effect of the TTS and chemotherapeutic agent. This is unexpected as, for example, one skilled in the art at the time of the invention understood that in order for TTS therapy to work, activation of the immune system was necessary. For example, activation of T-cells against targeted tumor cells. One skilled in the art at the time of the invention also understood that chemotherapeutic agents such as cytotoxic and cytostatic agents inhibit immune activation since they inhibit cell division. Applicants have unexpectedly found that chemotherapeutic agents, such as cytostatic and cytotoxic agents, may be administered together with TTS with the result being an enhanced effect of both the TTS and the chemotherapeutic agents. This includes the administration of both TTS and chemotherapeutic agents systemically, for example, by intravenous injection. The instant invention has discovered that TTS and chemotherapeutic drugs may be administered in varying combinations and doses, including but not limited to, full doses of TTS and chemotherapeutic agents wherein the chemotherapeutic is administered before TTS administration, with TTS administration or following TTS administration, for example and including shortly following TTS administration, as illustrated in FIG. 1. The instant invention has also discovered the multiple rounds of administration of varying combinations of TTS and chemotherapeutic agents may also be administered. For example, FIG. 1 shows multiple rounds of administration of TTS shortly followed by administration of a chemotherapeutic agent, such as a cytotoxic or cytostatic agent.

It has been discovered that combination administration of superantigens or TTS with chemotherapeutic agents reduces the development of an antibody response to the superantigen or TTS, whereas administration of TTS alone generates an antibody response to the superantigen or TTS. One skilled in the art at the time of the present invention knows that when superantigen or TTS is administered to animals, including mammals, including humans, it is not uncommon for the animal to develop an antibody response to the superantigen or TTS (e.g., to the superantigen or targeting moiety parts of the TTS or to both) following the first administration. This, therefore, makes repeated TTS therapy difficult, as increasing titers of antibodies in a patient may interfere with the anti-tumor action of the superantigen or TTS therapy. It is therefore an unexpected discovery of the present invention that coadministration of superantigen or TTS and chemotherapeutic agents, such as cytotoxic or cytostatic agents, for example but not limited to doses administered systemically, reduces the antibody response to the superantigen or TTS in a treated animal, thereby allowing for repeated administration of superantigen or TTS without the problems generated by an antibody response in the treated animal. One embodiment of achieving this effect is shown in the schematic treatment regime of FIG. 1, wherein a chemotherapeutic agent such as a cytostatic drug, is administered shortly following administration of each dose of TTS. It has unexpectedly been discovered that such administration of a cytotoxic agent, for example, inhibits the generation of a B-cell/antibody response to the TTS molecule, while not inhibiting—and even enhancing—the T-cell immune response associated with TTS therapy.

FIG. 2 shows a schematic of an embodiment of the present invention. For example, one or more treatments of TTS are followed directly by one or more treatments of a chemotherapeutic agent, such as a cytostatic agent. In the present invention it has, for example, been unexpectedly discovered that administration, such as systemic administration, of a chemotherapeutic agent, such as a cytotoxic or cytostatic agent, for example shortly following administration of TTS enhances, for example synergistically, the anti-tumor effect of the TTS and chemotherapeutic agent. For example, and as shown in FIG. 1B, the instant invention has shown that a preferred administration embodiment of the present invention is the administration of TTS in a four (4) day cycle followed by administration of a chemotherapeutic agent on day five (5). This round of combination treatment may be repeated more than once, for example and as shown in FIG. 2, by a second TTS administration on days 22-25 and administration of a chemotherapeutic agent on day 26. This cycling of coadministration may be continued. Still further, another example is shown in FIG. 1C and/or FIG. 1D in which the first TTS administration is either before or after the administration of a chemotherapeutic agent. If the chemotherapeutic agent is administered first or prior to the TTS, then the TTS is started after the effecitve concentration of the chemotherapeutic agent is reduced or has dropped in the subject below a functional inhibitory level. This time periord can be about 24 hours or less depending upon the chemotherapeutic agent. Thus, after this time period, TTS administration may be initiated. TTS can be administered systemically for a period of time to allow for sufficient production of effector cells, such time period can be about 1-2 days. After this period of time, then there can be a simultaneous administration of the chemotherapeutic agent and TTS as shown in FIG. 1C and FIG. 1D.

As discussed above, it has also been discovered in the present invention that such a combination of superantigen, such as TTS, and administration of a chemotherapeutic drug, such as a cytotoxic drug (for example at full dose, systemic administration), results in an unexpected inhibition in the generation of an antibody response to the superantigen (e.g., TTS), which, therefore, results in the unexpected ability to treat a patient, such as a human, with multiple rounds of superantigen (e.g., TTS) while having a reduced or eliminated possibility of the patient generating an antibody response to the superantigen (e.g., TTS). It is unexpected that, for example, superantigen (e.g., TTS) treatment in combination with a chemotherapeutic drug, such as a cytotoxic or cytostatic drug, would inhibit the B-cell/antibody-generating response while not inhibiting—and even enhancing—the T-cell/superantigen (TTS) anti-tumor response.

In illustrative examples, the TTS in FIGS. 1 and 2 may be, for example but not limited to, C215Fab-SEA (SEQ. ID. NO. 5) 5T4Fab-SEA/E-120 (SEQ. ID. NO. 7), or 5T4Fab-$SEA_{D227A}$ (SEQ. ID. NO. 6) administered systemically, for example by intravenous administration, the chemotherapeutic agent may be a cytotoxic or cytostatic agent, for example but not limited to, gemcitibine, docetaxel, cisplatin or pemetrexed, administered systemically, for example by intravenous administration, and at the "full" dose (i.e., the dose normally administered when the agent is administered alone), and the TTS and chemotherapeutic agent may be administered to an animal, such as a mammal, such as a human.

III. SUPERANTIGENS

Superantigens are bacterial proteins, viral proteins, and human-engineered molecules, capable of activating T lymphocytes, for example, at picomolar concentrations. Superantigens are characterized by their ability to activate large subsets of T lymphocytes. They bind to the major histocompatibility complex (MHC) without being processed. Superantigens bind to conserved regions outside the antigen-binding groove on MHC class II molecules, avoiding most of the polymorphism in the conventional peptide-binding site. Superantigens bind to the T-cell receptor (TCR) in the Vβ chain, instead of binding to the hypervariable loops of the T-cell receptor. Examples of bacterial superantigens include, but are not limited to, Staphylococcal enterotoxin (SE), *Streptococcus pyogenes* exotoxin (SPE), *Staphylococcus aureus* toxic shock-syndrome toxin (TSST-1), Streptococcal mitogenic exotoxin (SME), Streptococcal superantigen (SSA), Staphylococcal enterotoxin A (SEA), and Staphylococcal enterotoxin E (SEE).

The polynucleotide sequences encoding many superantigens have been isolated and cloned and superantigens expressed from these polynucleotide sequences have been used in anticancer therapy. Superantigens expressed by these polynucleotide sequences may be wild-type superantigens, modified superantigens, or wild-type or modified superantigens conjugated or fused with target-seeking moieties. Further, as explained in the following U.S. patents and patents applications, it is know in the art that superantigens may be administered to a mammal, such as a human, directly, for example by injection, or may be delivered, for example, by exposure of blood of a patient to the superantigen outside the body, or, for example, via placing a gene encoding a superantigen inside a mammal to be treated (e.g., via known gene therapy methods and vectors such as, for example, via cells containing, and capable of expressing, the gene) and expressing the gene within the mammal. Other routes of administration of superantigens are included within the scope of this invention.

Examples of superantigens and their administration to mammals may be found in the following U.S. patents and patent applications, each of which is hereby incorporated herein by reference in its entirety: U.S. Pat. Nos. 5,858,363, 6,197,299, 6,514,498, 6,713,284, 6,692,746, 6,632,640, 6,632,441, 6,447,777, 6,399,332, 6,340,461, 6,338,845, 6,251,385, 6,221,351, 6,180,097, 6,126,945, 6,042,837, 6,713,284, 6,632,640, 6,632,441, 5,859,207, 5,728,388, 5,545,716, 5,519,114, 6,926,694, 7,125,554, 7,226,595, 7,226,601, 7,094,603, 7,087,235, 6,835,818, 7,198,398, 6,774,218, 6,913,755, 6,969,616, and 6,713,284, U.S. Patent Application Nos. 20030157113, 20030124142, 20020177551, 20020141981, 20020115190, 20020051765, 60/378,988, 60/389,366, 60/406,697, 60/406,750, 60/415,310, 60/415,400, and 60/438,686 and PCT International Publication Number WO/03/094846. As defined herein, the term "superantigen(s)" includes wild-type and modified superantigens as well as targeted (e.g., conjugated or fused) superantigens. More preferably, the present invention concerns targeted (e.g., conjugated or fused) superantigens. The definition of the term "superantigen(s)" as used herein covers any molecule(s) capable of interacting with a TCR to activate a subset of T cells.

A. Modified Superantigens

Within the scope of this invention, superantigens may be modified from wild-type in virtually any number of ways. Examples of preferred embodiments include modifications that retain or enhance the ability of a superantigen to stimulate T lymphocytes, and may, for example, alter other aspects of the superantigen, such as, for example, its seroreactivity or immunogenicity. Modified supertantigens include synthetic molecules that have superantigen activity (i.e., the ability to activate subsets of T lymphocytes).

It is thus contemplated by the inventors that various changes may be made in the polynucleotide sequences encoding a superantigen without appreciable loss of its biological utility or activity, as discussed below. The activity being the induction of the T-cell response to result in cytotoxicity of the tumor cells. Yet further, the affinity of the superantigen for the MHC class II molecule can be decreased with minimal effects on the cytotoxicity of the superantigen. This, for example, helps to reduce toxicity that may otherwise occur if a superantigen retains its wild-type ability to bind MHC class II antigens (as in such a case, class II expressing cells, such as immune system cells, could also be affected by the response to the superantigen).

Techniques for modifying superantigens (e.g., polynucleotides and polypeptides), including for making synthetic superantigens, are well known in the art and include, for example PCR mutagenesis, alanine scanning mutagenesis, and site-specific mutagenesis (U.S. Pat. Nos. 5,220,007; 5,284,760; 5,354,670; 5,366,878; 5,389,514; 5,635,377; and 5,789,166, each of which is incorporated herein by reference).

In some embodiments, a superantigen may be modified such that its seroreactivity are reduced, compared to wild-type, but its ability to activate T cells is retained or enhanced relative to wild-type. One technique for making such modified superantigens is by substituting certain amino acids in certain regions from one superantigen to another. This is possible because many superantigens, for example but not limited to, SEA, SEE, SED share sequence homology in certain areas that have been linked to certain functions (Marrack and Kappler, 1990). For example, in certain embodiments of the present invention, a superantigen that has a desired T cell activation-inducing response, but a non-desired high seroreactivity, is modified such that the resulting superantigen retains its T cell activation ability, yet has reduced seroreactivity.

It is known and understood by those of skill in the art that the sera of humans normally contain various titers of antibodies against superantigens. For the staphylococcal superantigens, for instance, the relative titers are TSST-1>SEB>SEC-1>SE3>SEC2>SEA>SED>SEE. As can be seen, the seroreactivity of, for example, SEE (Staphylococcal enterotoxin E) is lower than that of, for example, SEA (Staphylococcal enterotoxin A). Based on this data, one skilled in the art would prefer to administer a low titer superantigen, such as, for example SEE, instead of a high titer superantigen, such as, for example, SEB (Staphylococcal enterotoxin B). However, as has also been discovered by the present inventors, different superantigens have differing T cell activation properties relative to one another, and for wild-type superantigens, the best T cell activating superantigens often also have undesirably high seroreactivity.

One skilled in the art also realizes that these relative titers indicate potential problems with seroreactivity, such as problems with neutralizing antibodies. Thus, the present invention contemplates using a low titer superantigen, such as SEA or SEE to avoid the seroreactivity of parenterally administered superantigens. A "low titer superantigen" has a low seroreactivity as measured, for example, by typical anti-superantigen antibodies in a general population. In some instances it may also have a low immunogenicity. Such low titer superantigens may be modified to retain its "low titer" as described herein.

The present inventors have discovered ways of modifying superantigens such that, for example, a modified superantigen may be created that has both the desired T cell activation properties and reduced seroreactivity, and in some instances also reduced immunogenicity. One way of accomplishing this is by the inventors' discovery that certain regions of homology between superantigens relate to seroreactivity. Using this information, it is within the skill of one in the art to engineer a recombinant superantigen that has a desired T cell activation and a desired seroreactivity and/or immunogenicity.

Yet further, it is clearly known and understood that the protein sequences and immunological cross-reactivity of the superantigens or staphylococcal enterotoxins are divided into two related groups. One group consists of SEA, SEE and SED. The second group is SPEA, SEC and SEB. Thus, the present invention also contemplates the use of low titer superantigens to decrease or eliminate the cross-reactivity of the present invention with high titer or endogenous antibodies against staphylococcal enterotoxins.

Regions the superantigens that have been identified as playing a role in seroreactivity include, for example, Region A, comprises amino acid residues 20, 21, 22, 23, 24, 25, 26, and 27; Region B comprises amino acid residues 34, 35, 36, 37, 38, 39, 40, 41, 42, 43, 44, 45, 46, 47, 48, and 49; Region C 74, 75, 76, 77, 78, 79, 80, 81, 82, 83, and 84; Region D comprises amino acid residues 187, 188, 189 and 190; and Region E comprise the amino acid residues, 217, 218, 219, 220, 221, 222, 223, 224, 225, 226, and 227 (U.S. Pat. No. 7,125,554), which are incorporated herein by reference in their entireties). Thus, it is contemplated that these identified regions are the regions in which one of skill in the art would mutate using, for example amino acid substitution, to produce a superantigen having altered seroreactivity.

Polypeptide or amino acid sequences for the above listed superantigens can be obtained from any sequence data bank, for example Protein Data Bank and/or GenBank. Exemplary GenBank accession numbers include, but are not limited to, SEE is P12993; SEA is P013163; SEB is P01552; SEC1 is P01553; SED is P20723; and SEH is AAA19777. Yet further, one skilled in the art can obtain the nucleic acid sequences of the above listed superantigens and other superantigens from GenBank.

In certain embodiments of the present invention, the wild-type SEE (SEQ. ID. NO. 1) or SEA sequence or (SEQ. ID. NO. 2) can be modified such that amino acids in any of the identified regions A-E are substituted with SEE amino acids. Such substitutions include for example, K79, K81, K83 and D227 or K79, K81, K83, K84 and D227, or, for example, K79E, K81E, K83S and D227S or K79E, K81E, K83S, K84S and D227A. More particularly, the superantigen is SEA/E-120 (SEQ. ID. NO. 3; see also U.S. Patent No. 7,125,554 which is incorporated herein by reference in its entirety) or SEAD227A (SEQ. ID. NO. 4; see also U.S. Pat. No. 7,226,601 which is incorporated herein by reference in its entirety).

1. Modified Polynucleotides and Polypeptides

The biological functional equivalent may comprise a polynucleotide that has been engineered to contain distinct sequences while at the same time retaining the capacity to encode the "wild-type" or standard protein. This can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide made be (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein and/or polynucleotide, is the concept that there is a limit to the number of changes that may be made within a defined portion of the molecule while retaining a molecule with an acceptable level of equivalent biological activity. Biologically functional equivalents are thus defined herein as those proteins (and polynucleotides) in selected amino acids (or codons) may be substituted. Functional activity being the induction of the T-cell response to result in cytotoxicity of the tumor cells. Yet further, the affinity of the superantigen for the MHC class II molecule is decreased with minimal effects on the cytotoxicity of the superantigen.

In general, the shorter the length of the molecule, the fewer changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, and/or the like. An analysis of the size, shape and/or type of the amino acid side-chain substituents reveals that arginine, lysine and/or histidine are all positively charged residues; that alanine, glycine and/or serine are all a similar size; and/or that phenylalanine, tryptophan and/or tyrosine all have a generally similar shape. Therefore, based upon these considerations, arginine, lysine and/or histidine; alanine, glycine and/or serine; and/or phenylalanine, tryptophan and/or tyrosine; are defined herein as biologically functional equivalents.

To effect more quantitative changes, the hydropathic index of amino acids may be considered. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index and/or score and/or still retain a similar biological activity. In making changes based upon the hydropathic index, the substitution of amino acids whose hydropathic indices are within ±2 is preferred, those which are within ±1 are particularly preferred, and/or those within ±0.5 are even more particularly preferred.

It also is understood in the art that the substitution of like amino acids can be made effectively on the basis of hydrophilicity, particularly where the biological functional equivalent protein and/or peptide thereby created is intended for use in immunological embodiments, as in certain embodiments of the present invention. U.S. Pat. No. 4,554,101, incorporated herein by reference, states that the greatest local average hydrophilicity of a protein, as governed by the hydrophilicity of its adjacent amino acids, correlates with its seroreactivity and/or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and/or those within +0.5 are even more particularly preferred.

2. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified and/or unusual amino acids. A table (Table 1) of exemplary, but not limiting, modified and/or unusual amino acids is provided herein below.

TABLE 1

Modified and/or Unusual Amino Acids

| Abbr. | Amino Acid |
|---|---|
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| Aile | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

3. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody and/or antigen. A peptide mimetic is thus designed to permit molecular interactions similar to the natural molecule.

Some successful applications of the peptide mimetic concept have focused on mimetics of β-turns within proteins, which are known to be highly antigenic. Likely β turn structure within a polypeptide can be predicted by computer-based algorithms, as discussed herein. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins Vita et al. (1995). A structural motif that appears to be evolutionarily conserved in certain toxins is small (30-40 amino acids), stable, and high permissive for mutation. This motif is composed of a beta sheet and an alpha helix bridged in the interior core by three disulfides.

Beta II turns have been mimicked successfully using cyclic L-pentapeptides and those with D-amino acids. Weisshoff et al. (1999). Also, Johannesson et al. (1999) report on bicyclic tripeptides with reverse turn inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

Other proteins and molecules that are within the scope of this invention include that that may vary in, for example, glycosylation, but retain the same function (e.g., so-called "biosimilar" or "bioequivalent" proteins).

4. Domain switching

Yet further, a modified superantigen can be created by substituting homologous regions of various proteins. This is known, in certain contexts, as "domain switching." Domain switching involves the generation of chimeric molecules using different but, in this case, related polypeptides. By comparing various superantigen proteins, one can make predictions as to the functionally significant regions of these molecules. It is possible, then, to switch related domains of these molecules in an effort to determine the criticality of these regions to superantigen function. These molecules may have additional value in that these "chimeras" can be distinguished from natural molecules, while possibly providing the same function.

B. Targeted Superantigens

In certain embodiments of the present invention, a targeting moiety, for example an antibody or antibody fragment, may be conjugated to a superantigen, providing a targeted superantigen. If the antibody, or antibody fragment recognizes a tumor-associated antigen, the targeted superantigen may be called a tumor-targeted superantigen ("TTS"). Targeted superantigens retain the ability to activate large number of T lymphocytes, and add the ability to direct the activated lymphocytes to cells bearing the target moiety. For example, TTS molecules active large numbers of T cells and direct them to tissues containing the tumor-associate antigen bound by the targeting moiety. In such situations, specific target cells are killed, leaving the rest of the body relatively unharmed. Such "magic bullet" therapy is quite desired in the art, as non-specific anticancer agents, such as cytostatic chemotherapeutic drugs, are nonspecific and kill large numbers of cells that are not associated with tumors to be treated. For example, studies with TTS have shown that inflammation by cytotoxic T lymphocytes (CTLs) into tumor tissue increases rapidly in response to the first injection of a targeted superantigen (Dohlsten et al., 1995). This inflammation with infiltration of CTLs into the tumor is one of the major effectors of the anti-tumor therapeutic of targeted superantigens.

As used in the present invention, tumor-targeted superantigens (TTS) represent an immunotherapy against cancer and are therapeutic fusion proteins containing a targeting moiety and a superantigen (Dohlsten et al., 1991; Dohlsten et al., 1994). These types of compounds are disclosed and thoroughly described in e.g., WO9201470, EP 610179, U.S. Pat. No. 5,858,363, U.S. Pat. No. 6,197,299, WO9601650, EP 766566, and WO03002143, each of which is incorporated herein by reference in its entirety. Examples of TTS that can be used in the present invention include C215Fab-SEA (SEQ. ID. NO. 5), 5T4Fab-SEA$_{D227A}$ (SEQ. ID. NO. 6) and 5T4Fab-SEA/E-120 (SEQ. ID. NO. 7).

The targeting moiety can in principle be any structure that is able to bind to a cell surface structure, preferably a disease specific structure. The structure against which the targeting moiety is directed is usually different from (a) the Vβ chain epitope to which Superantigen binds, and (b) the MHC class II epitopes to which superantigens bind. The target-seeking moiety is primarily selected among antibodies, including antigen binding fragments of antibodies and related entities, soluble T cell receptors, growth factors, interleukins (e.g., interleukin-2), hormones, etc. See for example U.S. Pat. Nos. 6,080,840, 6,514,498; 5,858,363; 6,197,299; U.S. Application No. U.S. 2004/0126379, U.S. 2003/0175212, U.S. 2003/0144474, U.S. 2002/0142389, U.S. 2002/119149 and International Publications WO2003020763, WO2004050705, WO2003002143, WO9960120 and WO9960119 each of which is incorporated herein by reference.

In certain embodiments, the targeting moiety is an antibody (e.g., Fab, F(ab)$_2$, Fv, single chain antibody, etc.). One of skill in the art is aware that antibodies are extremely versatile and useful cell-specific targeting moieties because they can be generated against any cell surface antigen of interest. Monoclonal antibodies have been generated against cell surface receptors, tumor-associated antigens, and leukocyte lineage-specific markers such as CD antigens. Antibody variable region genes can be readily isolated from hybridoma cells by methods well known in the art. Exemplary tumor associated antigens that can be used to produce a target moiety can include, but are not limited to gp100, Melan-A/MART, MAGE-A, MAGE (melanoma antigen E), MAGE-3, MAGE-4, MAGEA3, tyrosinase, TRP2, NY-ESO-1, CEA (carcinoembryonic antigen), PSA, p53, Mammaglobin-A, Survivin, Muc1 (mucin1)/DF3, metallopanstimulin-1 (MPS-1), Cytochrome P450 isoform 1B1, 90K/Mac-2 binding protein, Ep-CAM (MK-1), HSP-70, hTERT (TRT), LEA, LAGE-1/CAMEL, TAGE-1, GAGE, 5T4, gp70, SCP-1, c-myc, cyclin B1, MDM2, p62, Koc, IMP1, RCAS1, TA90, OA1, CT-7, HOM-MEL-40/SSX-2, SSX-1, SSX-4, HOM-TES-14/SCP-1, HOM-TES-85, HDAC5, MBD2, TRIP4, NY—CO-45, KNSL6, HIP1R, Seb4D, KIAA1416, IMP1, 90K/Mac-2 binding protein, MDM2, NY/ESO, and LMNA.

As used herein, exemplary cancer antibodies can include, but are not limited to anti-CD19, anti-CD20, anti-5T4, anti-Ep-CAM, anti-Her-2/neu, anti-EGFR, anti-CEA, anti-prostate specific membrane antigen (PSMA)/folate hydrolase 1 (FOLH1), anti-IGF-1R.

Still further, the superantigen of the present invention can be fused and/or conjugated to antibody active fragments such as C215Fab, 5T4Fab (WO8907947, which is incorporated herein by reference in its entirety) or C242Fab (Lindholm et al., WO9301303, which is incorporated herein by reference in its entirety).

Another type of targeting moiety includes a soluble T cell receptor (TCR). Some forms of soluble TCR may contain either only extracellular domains or extracellular and cytoplasmic domains. Other modifications of the TCR may also be envisioned to produce a soluble TCR in which the transmembrane domains have been deleted and/or altered such that the TCR is not membrane bound as described in U.S. Publication Application Nos. U.S. 2002/119149, U.S. 2002/0142389, U.S. 2003/0144474, and U.S. 2003/0175212, and International Publication Nos. WO2003020763; WO9960120 and WO9960119, each of which is incorporated herein in its entirety.

The targeting moiety can be added to the superantigen by using either recombinant techniques or chemically linking of the targeting moiety to the superantigen. These methods are well recognized for the ordinary skilled worker and comprise a large number of variants.

1. Recombinant Linkage

For recombinant superantigens, in the form of fusion proteins or in some cases as conjugates, the obtained substance will be uniform with respect to the linking position. Either the amino terminal of a modified superantigen is linked to the carboxy terminal of the targeting moiety or vice versa. For antibodies, either the light or the heavy chain may be utilized for fusion. For example, for Fab fragments the amino terminal of the modified superantigen is linked to the first constant domain of the heavy antibody chain (CH1). Yet further, the modified superantigen can also be linked to an Fab fragment by linking the light chain or to the VH1 and VL domain to the superantigen. Still further, a bridge or peptide linker can be used to fuse the to compositions together. Conjugation or fusion using a linker or bridge can be performed using recombinant techniques. In such cases oligopeptide bridges containing hydrophilic amino acid residues, such as Gln, Ser, Gly, Glu, Pro, His and Arg are preferred. Particularly preferred bridges are peptide bridges consisting of 1-10 amino acid residues, more particularly, for 3-7 amino acid residues. An exemplary bridge is the tripeptide GlyGlyPro.

2. Chemical Linkage

It is also envisioned that the modified superantigen may be linked to the targeting moiety via chemical linkage. Chemical linkage of the two compounds may require a linking or peptide bridge. The bridge is preferably hydrophilic and exhibits one or more structure(s) selected among amide, thioether, disulphide etc. (See U.S. Pat. Nos. 5,858,363, 6,197,299, and 6,514,498, which are incorporated herein by reference in their entireties).

Chemical linking of a modified superantigen to a targeting moiety often utilizes functional groups (e.g., primary amino groups or carboxy groups) that are present in many positions in the compounds. It follows that the final product will contain a mixture of conjugate molecules differing in linking positions, as well as hetero- and homo-conjugates.

C. Expression of the Superantigens

The present invention also involves the use of expression vectors and host cells. These expression vectors, which have been genetically engineered to contain the nucleic acid sequence of the superantigen, are introduced or transformed into host cells to produce the superantigen of the present invention (See Dohlsten et al., 1994, Forsberg et al., 1997, Erlandsson et al., 2003 and WO2003002143, each of which is incorporated herein by reference Host cells can be genetically engineered to incorporate nucleic acid sequences and express peptides of the present invention. Introduction of nucleic acid sequences into the host cell can be affected by calcium phosphate transfection, DEAE-dextran mediated transfection, transvection, microinjection, cationic lipid-mediated transfection, electroporation, transduction, scrape loading, ballistic introduction, infection or other methods. Such methods are described in many standard laboratory manuals, such as, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), each of which are incorporated herein by reference.

Representative examples of appropriate host cells include bacterial cells, such as streptococci, staphylococci, *E. coli*, *streptomyces* and *Bacillus subtilis* cells; fungal cells, such as yeast cells and *aspergillus* cells; insect cells such as *Drosophila* S2 and *Spodoptera* Sf9 cells; animal cells such as CHO, COS, HeLa, C127, 3T3, BHK, 293 and Bowes melanoma cells.

Examples of production systems for superantigens are found, for example, in U.S. Pat. No. 6,962,694, which is incorporated herein by reference in its entirety.

D. Purification of Proteins

It will be desirable to purify the superantigen or variants thereof. Protein purification techniques are well known to those of skill in the art. These techniques involve, at one level, the crude fractionation of the cellular milieu to peptide and non-peptide fractions. Having separated the protein from other proteins, the protein of interest may be further purified using chromatographic and electrophoretic techniques to achieve partial or complete purification (or purification to homogeneity). Analytical methods particularly suited to the preparation of a pure peptide are ion-exchange chromatography, size exclusion chromatography; affinity chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

IV. ANTICANCER AGENT AND/OR THERAPY

An "anticancer" agent and/or therapy is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

Tumor cell resistance to chemotherapy and radiotherapy agents represents a major problem in clinical oncology. One goal of current cancer research is to find ways to improve the efficacy of chemo- and radiotherapy by combining it with an immunotherapy, such as a superantigen. Thus, in the context of the present invention, it is contemplated that the superantigen therapy could be used in combination with chemotherapeutic agents and/or radiotherapeutic agents.

A. Chemotherapeutic Agents

Chemotherapeutic drugs or agents include cytotoxic and cytostatic drugs that alone or in combination that have an affect on a hyperproliferative disease or condition in a mammal, such as a human. These terms include, but are not limited to, chemical, biological, and physical agents that act directly on (e.g., affects) a hyperproliferative cell (e.g., cancer or tumor) or the vascularization of a hyperproliferation. In this context, the term "agent" includes, but is not limited to a drug. These include, but are not limited to cytostatic agents, cytotoxic (cytocidal) agents, and anti-angiogenesis agents, but do not include immune modulators (agents that act by modulating the immune system (other than by cytotoxic or cytostatic action) such as interleukin-2 (IL-2) and linomide.

In some embodiments, a chemotherapeutic agent is used to connote a compound or composition that is administered in the treatment of cancer. Such agents or drugs may be categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Cytostatic agents are defined as agents or drugs that prevent the growth and proliferation of cells. One of skill in the art understands that a cytostatic agent is a chemotherapeutic agent. More particularly, the cytostatic agents that may be used in combination with a superantigen include, but are not limited to, alkylating agents (e.g., cyclophosphamide, chlorambucil, melphalan); antimetabolites (e.g., mercaptopurine, cladribine, cytarabine, fluorouracil gemcitabine); anti-tumor antibiotics (e.g., doxorubicin, epirubicin, mitoxantrone, mitomycin); inhibitor of mitosis (e.g., vinblastine, vincristine, vinorelbine, paclitaxel, docetaxel, etoposide, topotecan, irinotecan); platinum based compounds (e.g., cisplatin, carboplatin), and corticosteroid hormones. It is also within the scope of the invention to combine cytocidal (cytotoxic) chemotherapeutic agents or drugs with superantigen administration, as well as to combine agents tht negatively affect the vascularization of tumors (anti-angiogenesis agents) with drugs with superantigen administration.

1. Corticosteroid Hormones

Corticosteroid hormones are useful in treating some types of cancer (lymphoma, leukemias, and multiple myeloma). Though these hormones have been used in the treatment of many non-cancer conditions, they are considered chemotherapy drugs when they are implemented to kill or slow the growth of cancer cells. Corticosteroid hormones can increase the effectiveness of other chemotherapy agents, and consequently, they are frequently used in combination treatments, including with superantigen therapy. Prednisone and dexamethasone are examples of corticosteroid hormones.

2. Alkylating agents

Alkylating agents are drugs that directly interact with genomic DNA to prevent the cancer cell from proliferating. This category of cytostatic drugs represents agents that affect all phases of the cell cycle, that is, they are not phase-specific. More specifically, alkylating agents, or their reactive intermediates, form covalent bonds with deoxyribonucleic acid (DNA), ribonucleic acid (RNA), and protein to form an adduct in which a methyl or ethyl group is added. DNA adducts are believed to play a major role in mutagenesis and clastogenesis, as well as in carcinogenesis. DNA adducts are formed at a number of reactive sites on nucleotide bases. Common locations include the N-7 and 0-6 of guanine which are shown to be associated with mutagenesis and carcinogenesis. In general, it seems that alkylating agents that are not particularly ionic in nature are localized more on the ring nitrogen atoms, whereas those that have greater ionic character show greater preferences for reaction at the oxygen atoms in DNA. Alkylating agents can be implemented to treat chronic leukemia, non-Hodgkin's lymphoma, Hodgkin's disease, multiple myeloma, and particular cancers of the breast, lung, and ovary. Exemplary alkylating agents include, Busulfan (Myleran), Chlorambucil, Cyclophosphamide (Cytoxan), Dacarbazine (DTIC-Dome), Estramustine Phosphate, Ifosphamide, Mechlorethamine (Nitrogen Mustard), Melphalan (Phenylalanine Mustard), Procarbazine, Thiotepa, and Uracil Mustard.

Yet further, nitrosoureas appear to function as alkylating agents, as well as through other mechanisms such as carbamoylation, which is a reaction occurring between an isocyanate and a reactant capable of losing a proton and involving the formation of a covalent bound between the isocyanate and its reactant. Alkylation is a reaction attributed to nucleic acid alkylation and carbamoylation is attributed to protein carbamoylation.

The nitrosoureas are converted non enzymatically into a carbonium ion and an isothiocyanate molecule. The carbonium ion acts as a typical alkylating agent and is probably responsible for the cytotoxic action of the nitrosoureas. The isothiocyanate may interact with proteins and account for some of the toxic effects of these drugs. Nitrosoureas are highly lipophilic, which allows them to readily cross lipophilic membranes such as those found in the central nervous system and skin. Exemplary nitrosoureas include, Carmustine (BCNU), Lomustine (CCNU), Semustine (methyl-CCNU), and Streptozocin A superantigen can be used to treat a cancer in combination with any one or more of these alkylating agents, some of which are discussed below.

a) Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride. The half-life of busulfan is about 2.5 hours. Busulfan is rapidly and probably completely absorbed from the GI tract, and measurable blood concentrations are obtained within 0.5-2 hours after oral administration of the drug. Busulfan is slowly excreted in urine, as metabolites. About 10-50% of a dose is excreted as metabolites within 24 hours.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

In practicing the present invention, one skilled in the art would know that superantigen therapy could be sequentially administered in combination with busulfan, for example, by first treating with busulfan. Once the effective cytostatic concentration of busulfan has dropped in the patient below a functional inhibitory level, the superantigen can be administered to the patient.

b) Chlorambucil

Chlorambucil (also known as leukeran) is a bifunctional alkylating agent of the nitrogen mustard type that has been found active against selected human neoplastic diseases. Chlorambucil is known chemically as 4-[bis(2-chlorethyl)amino] benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m2/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

In practicing the present invention, one skilled in the art would know that superantigen therapy could be sequentially administered in combination with chlorambucil, for example, by first treating with chlorambucil. Once the effective cytostatic concentration of chlorambucil has dropped in the patient below a functional inhibitory level, the superantigen can be administered to the patient.

c) Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)2N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain. Cyclophosphamide has a half-life of about 4-8 hours and is metabolized by the liver into its active components: acrolein, 4-aldophosphamide, 4-hydroperoxycyclophosphamide, and nor-nitrogen mustard.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

In practicing the present invention, one skilled in the art would know that superantigen therapy could be sequentially administered in combination with cyclophosphamide, for example, by first treating with cyclophosphamide. Once the effective cytostatic concentration of cyclophosphamide has dropped in the patient below a functional inhibitory level, the superantigen can be administered to the patient.

d) Melphalan

Melphalan, also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis (2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKal of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject.

Absorption of melphalan from the gastrointestinal tract is variable; the mean bioavailability is reported to be 56% but it may range from 25 to 89%. Absorption is reduced by the presence of food. Following absorption it is rapidly distributed throughout body water with a volume of distribution of about 0.5 liters per kg body-weight, and has been reported to be inactivated mainly by spontaneous hydrolysis. The terminal plasma half-life of melphalan has been reported to be of the order of 40 to 140 minutes. Melphalan is excreted in the urine, about 10% as unchanged drug. About 50 to 60% of an absorbed dose has been stated to be protein bound initially, increasing to 80 to 90% after 12 hours.

In practicing the present invention, one skilled in the art would know that superantigen therapy could be sequentially administered in combination with melphalan, for example, by first treating with melphalan. Once the effective cytostatic concentration of melphalan has dropped in the patient below a functional inhibitory level, the superantigen can be administered to the patient.

e) Carmustine

Carmustine (sterile carmustine) is one of the nitrosoureas used in the treatment of certain neoplastic diseases. It is 1,3bis(2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. The average terminal half-life is about 22 minutes.

When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

In practicing the present invention, one skilled in the art would know that superantigen therapy could be sequentially administered in combination with carmustine, for example, by first treating with carmustine. Once the effective cytostatic concentration of carmustine has dropped in the patient below a functional inhibitory level, the superantigen can be administered to the patient.

f) Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/M$^2$ as a single oral dose every 6 weeks. In individuals with compromised bone marrow function, the dose should be reduced to 100 mg/m$^2$ every 6 weeks. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

In practicing the present invention, one skilled in the art would know that superantigen therapy could be sequentially administered in combination with lomustine, for example, by first treating with omustine. Once the effective cytostatic concentration of lomustine has dropped in the patient below a functional inhibitory level, the superantigen can be administered to the patient.

3. Antimetabolites

Antimetabolites disrupt DNA and RNA synthesis. Unlike alkylating agents, antimetabolites specifically influence the cell cycle during S phase. Antimetabolites that are structural analogues of nucleotides are incorporated into cell components as if they were the essential pyrimidine or purine, and as a consequence, disrupt the synthesis of nucleic acids. Other antimetabolites disrupt essential enzymatic processes of metabolism. An example is the folate antagonist, 5-fluorouracil, which disrupts vital folic acid metabolism. Exemplary antimetoblites include, Cladribine, Cytarabine (Cytosine Arabinoside), Floxuridine (FUDR, 5-Fluorodeoxyuridine), Fludarabine, 5-Fluorouracil (5FU), Gemcitabine, Hydroxyurea, 6-Mercaptopurine (6 MP), Methotrexate (Amethopterin), 6-Thioguanine, Pentostatin, Pibobroman, Tegafur, Trimetrexate, Glucuronate.

Antimetabolites have used to combat chronic leukemias in addition to tumors of breast, ovary and the gastrointestinal tract. Superantigens can be used in combination with one or more of the antimetabolites described herein below.

a) 5-Fluorouracil And Related Compounds

5-Fluorouracil (5-FU) is the chemical name of 5-fluoro-2, 4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

The elimination half-life of 5-FU is 6 to 20 minutes and is dose-dependent. The metabolism of 5-FU occurs mainly in the liver and results in degradation products (e.g., carbon dioxide, urea, a-fluoro-b-alanine) which are inactive. Approximately 15% of the dose is excreted intact in the urine in 6 hours and over 90% of this is excreted in the first hour; 60 to 80% is excreted as respiratory carbon dioxide in 8 to 12 hours.

In practicing the present invention, one skilled in the art would know that superantigen therapy could be sequentially administered in combination with 5-FU, for example, by first treating with 5-FU. Once the effective cytostatic concentration of 5-FU has dropped in the patient below a functional inhibitory level, the superantigen can be administered to the patient.

Other compounds that are related to 5-FU are also included within the present invention (e.g., but not limited to capecitabine XELODA® (Roche)).

b) Gemcitabine

Gemcitabine is commonly used to for non-small cell lung carcinomas and pancreatic carcinoma. Gemcitabine dosages of 1000 or 1250 mg/m$^2$ are administered by 30-minute IV infusion once weekly for 3 weeks followed by 1 week of rest. Various dosage schedules have been studied for the combination of gemcitabine with cisplatin for the treatment of advanced non-small cell lung cancer; gemcitabine dosages of 1000 mg/m$^2$ administered once weekly for 3 weeks on a 4-week cycle or 1250 mg/m$^2$ administered once weekly for 2 weeks on a 3-week cycle have been used in large randomized trials. Other dosage schedules for gemcitabine (e.g., higher doses, lower doses administered over longer infusion periods) can also be used. For example, doses of 65 mg/kg may also be administered.

The half-life of gemcitabine depends upon the length of the infusion period, age and gender. For example, gemcitabine half-life for short infusions range from 32 to 94 minutes, and the value for long infusions vary from 245 to 638 minutes. The lower clearance in women and the elderly results in higher concentrations of gemcitabine for any given dose. In practicing the present invention, one skilled in the art would know that superantigen therapy could be sequentially administered in combination with gemcitabine, for example, by first treating with gemcitabine. Once the effective cytostatic concentration of gemcitabine has dropped in the patient below a functional inhibitory level, the superantigen can be administered to the patient.

c) Pemetrexed

Pemetrexed (Alimta®) is an antifolate agent. More specifically, pemetrexed and its polyglutamates inhibit at least four enzymes involved in folate metabolism and DNA synthesis; this multitargeted action is speculated to limit development of drug resistance. It is approved for the treatment of patients with malignant pleural mesothelioma who are not candidates for surgical resection. The drug has also shown anti-tumor activity in non-small-cell lung cancer, colorectal carcinoma, breast cancer, and several other malignancies.

Pemetrexed is administered intravenously (IV) at a dose of 500 milligrams/square meter (mg/m$^2$) over 10 minutes on day 1 of each 21-day cycle. After intravenous doses (ranging from 0.2 to 838 mg/m$^2$), pemetrexed has a volume of distribution of 16.1 liters, suggesting limited distribution in tissues, and a clearance of 91.8 milliliters/minute. Protein binding is about 81%. Metabolism appears minimal, and most of a dose is excreted unchanged in the urine. The half-life is about 3.5 hours.

In practicing the present invention, one skilled in the art would know that superantigen therapy could be sequentially administered in combination with pemetrexed, for example, by first treating with pemetrexed. Once the effective cytostatic concentration of pemetrexed has dropped in the patient below a functional inhibitory level, the superantigen can be administered to the patient.

4. Anti-tumor Antibiotics

Anti-tumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Most anti-tumor antibiotics intercalate between DNA base pairs and disturb the synthesis and/or function of nucleic acids. However, a different mechanism is ascribed to bleomycin. Bleomycin apparently binds to DNA and results in single-strand breaks and double-strand scissions, thereby disrupting DNA synthesis. Doxorubicin not only intercalates between base pairs, but also alkylates macromolecules. Daunorubicin, doxorubicin, and their derivatives, belong to a subclass of anti-tumor antibiotics called anthracyclines. Exemplary anti-tumor antibiotics include, Aclarubicin, Bleomycin, Dactinomycin (Actinomycin D), Daunorubicin, Doxorubicin (Adriamycin), Epirubicin, Idarubicin, Mitomycin C, Mitoxantrone, Plicamycin (Mithramycin). Superantigens can be used in combination with one or more of the anti-tumor antibiotics described herein below.

a) Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/M$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

In practicing the present invention, one skilled in the art would know that superantigen therapy could be sequentially administered in combination with doxorubicin, for example, by first treating with doxorubicin. Once the effective cytostatic concentration of doxorubicin has dropped in the patient below a functional inhibitory level, the superantigen can be administered to the patient.

b) Daunorubicin

Daunorubicin hydrochloride, 5,12-Naphthacenedione, (8S-cis)-8-acetyl-10-[(3-amino-2,3,6-trideoxy-a-L-lyxohexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/M$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

In practicing the present invention, one skilled in the art would know that superantigen therapy could be sequentially administered in combination with daunorubicin, for example, by first treating with daunorubicin. Once the effective cytostatic concentration of daunorubicin has dropped in the patient below a functional inhibitory level, the superantigen can be administered to the patient.

c) Mitomycin

Mitomycin (also known as mutamycin and/or mitomycin-C) is an antibiotic isolated from the broth of *Streptomyces caespitosus* which has been shown to have anti-tumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

In practicing the present invention, one skilled in the art would know that superantigen therapy could be sequentially administered in combination with mitomycin, for example, by first treating with mitomycin. Once the effective cytostatic concentration of mitomycin has dropped in the patient below a functional inhibitory level, the superantigen can be administered to the patient.

d) Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors that fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0.5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

In practicing the present invention, one skilled in the art would know that superantigen therapy could be sequentially administered in combination with actinomycin D, for example, by first treating with actinomycin D. Once the effective cytostatic concentration of actinomycin D has dropped in the patient below a functional inhibitory level, the superantigen can be administered to the patient.

e) Bleomycin

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin. Bleomycin may be given by the intramuscular, intravenous, or subcutaneous routes. It is freely soluble in water.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

In practicing the present invention, one skilled in the art would know that superantigen therapy could be sequentially administered in combination with bleomycin, for example, by first treating with bleomycin. Once the effective cytostatic concentration of bleomycin has dropped in the patient below a functional inhibitory level, the superantigen can be administered to the patient.

5. Mitotic Inhibitors

Mitotic inhibitors include plant alkaloids and other natural agents that can inhibit either protein synthesis required for cell division or mitosis. They operate during a specific phase during the cell cycle. Mitotic inhibitors include among others the vinca alkaloids (vincristine and vinblastine) which are mitotic spindle inhibitors and the epipodophyllotoxins (teniposide and etoposide) which are DNA topoisomerase II inhibitors. Mitotic spindle inhibitors bind to microtubular proteins and block their ability to polymerize or depolymerize, a process which halts nuclear division. DNA topoisomerase II inhibitors block religation of double strand DNA breaks (e.g., sister chromatid separation or cleaved DNA). Examples include Etoposide (VP-16, VePesid), Paclitaxel (TAXOL®), Docetaxel (Taxotere) Teniposide (VM-26, Vumon), Vinblastine, Vincristine, Vindesine, Topotecan, and Irinotecan. Superantigens can be used in combination with one or more of the mitotic inhibitors described herein below.

a) Paclitaxel

Paclitaxel (TAXOL®) is an experimental antimitotic agent, isolated from the bark of the ash tree, *Taxus brevifolia*. It binds to tubulin (at a site distinct from that used by the vinca alkaloids) and promotes the assembly of microtubules. Paclitaxel is known to have activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

In patients treated with doses of 135 and 175 mg/m$^2$ given as 3 and 24 hour infusions, half-life ranges from 3.0 to 52.7 hours, and total body clearance ranges from 11.6 to 24.0 L/h/m$^2$. Mean steady state volume of distribution following single dose infusion of 135 and 175 mg/m$^2$ ranges from 198 to 688 L/m$^2$, indicating extensive extravascular distribution and/or tissue binding. The volume of distribution is reduced in female subjects. Following 3 hour infusions of 175 mg/M$^2$, mean terminal half-life is estimated to be 9.9 hours; mean total body clearance is 12.4 L/h/m$^2$.

In practicing the present invention, one skilled in the art would know that superantigen therapy could be sequentially administered in combination with paclitaxel, for example, by first treating with paclitaxel. Once the effective cytostatic concentration of paclitaxel has dropped in the patient below a functional inhibitory level, the superantigen can be administered to the patient.

b) Docetaxel

Docetaxel (TAXOTERE®) is given as a treatment for some types of cancer. It is most commonly used to treat breast cancer and non-small cell lung cancer, but may be used for other types of cancer. Docetaxel is administered by IV infusion over a 1-hour period under ambient room temperature and lighting conditions. The dosage of docetaxel ranges from 20 mg/m$^2$ to 115 mg/m$^2$. The half-life is about 13.5+/−7.5 hours.

In practicing the present invention, one skilled in the art would know that superantigen therapy could be sequentially administered in combination with docetaxel, for example, by first treating with docetaxel. Once the effective cytostatic concentration of docetaxel has dropped in the patient below a functional inhibitory level, the superantigen can be administered to the patient.

c) Vinblastine

Vinblastine is another example of a plant aklyloid that can be used in combination with an superantigen for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation.

After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

In practicing the present invention, one skilled in the art would know that superantigen therapy could be sequentially administered in combination with vinblastine, for example, by first treating with vinblastine. Once the effective cytostatic concentration of vinblastine has dropped in the patient below a functional inhibitory level, the superantigen can be administered to the patient.

d) Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m2, 0.05 mg/m2, 0.06 mg/m2, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

In practicing the present invention, one skilled in the art would know that superantigen therapy could be sequentially administered in combination with vincristine, for example, by first treating with vincristine. Once the effective cytostatic concentration of vincristine has dropped in the patient below a functional inhibitory level, the superantigen can be administered to the patient.

e) Etoposide (VP16)

VP16 is also known as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/M$^2$, routinely 35 mg/M$^2$, daily for 4 days, to 50 mg/M$^2$, daily for 5 days have also been used. When given orally, the dose should be doubled. Hence the doses for small cell lung carcinoma may be as high as 200-250 mg/m$^2$. The intravenous dose for testicular cancer (in combination therapy) is 50 to 100 mg/m$^2$ daily for 5 days, or 100 mg/m² on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

On intravenous administration, the disposition of VP16 is best described as a biphasic process with a distribution half-life of about 1.5 hours and terminal elimination half-life ranging from 4 to 11 hours. Total body clearance values range from 33 to 48 mL/min or 16 to 36 mL/min/m² and, like the terminal elimination half-life, are independent of dose over a range 100-600 mg/M².

In practicing the present invention, one skilled in the art would know that superantigen therapy could be sequentially administered in combination with VP16, for example, by first treating with VP16. Once the effective cytostatic concentration of VP16 has dropped in the patient below a functional inhibitory level, the superantigen can be administered to the patient.

6. Platinum Based Compounds

Platinum-based compounds are among the most active chemotherapeutic agents available. They are effective against a multitude of cancers. Platinum-containing antineoplastic agents, such as carboplatin and cisplatin, appear to exert their effects by binding to DNA, thereby inhibiting DNA synthesis. The drugs are cycle-phase nonspecific. Carboplatin and cisplatin appear to act on tumor cells by the same general molecular mechanisms and, once bound to DNA, have virtually the same action. Although the principal mechanism of action of the drugs appears to be inhibition of DNA synthesis, other mechanisms also are involved in their antineoplastic activity. Superantigens can be used in combination with one or more of the platinum-based compounds described herein below.

a) Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m² for 5 days every three weeks for a total of three courses. Exemplary doses may be 0.50 mg/m², 1.0 mg/m², 1.50 mg/m², 1.75 mg/m², 2.0 mg/m², 3.0 mg/M², 4.0 mg/M², 5.0 mg/M², 10 mg/m². Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

Plasma concentrations of cisplatin decay monoexponentially with a half-life of about 20 to 30 minutes following bolus administration of. 50 or 100 mg/m² doses. Monoexponential decay and plasma half-lives of about 0.5 hour are also seen following two hour or seven hour infusions of 100 mg/m².

Following cisplatin doses of 20 to 120 mg/m², the concentrations of platinum are highest in liver, prostate, and kidney, somewhat lower in bladder, muscle, testicle, pancreas, and spleen and lowest in bowel, adrenal, heart, lung, cerebrum, and cerebellum. Platinum is present in tissues for as long as 180 days after the last administration. Maximum red blood cell concentrations of platinum are reached within 90 to 150 minutes after a 100 mg/m² dose of cisplatin and decline in a biphasic manner with a half-life of 36 to 47 days.

In practicing the present invention, one skilled in the art would know that superantigen therapy could be sequentially administered in combination with cisplatin, for example, by first treating with cisplatin. Once the effective cytostatic concentration of cisplatin has dropped in the patient below a functional inhibitory level, the superantigen can be administered to the patient.

b) Carboplatin

Carboplatin and cisplatin are associated with different toxicity profiles and carboplatin may be effective in patients with platinum-responsive tumors who are unable to tolerate cisplatin because of renal impairment, refractory nausea, hearing impairment, or neuropathy. It has been suggested that while carboplatin may be preferred in patients with renal failure or patients at high risk for ototoxicity or neurotoxicity, cisplatin may be preferred in patients who have decreased bone marrow reserve, a high risk of sepsis, or require anticoagulation therapy.

Dosage of carboplatin is based on the clinical, renal, and hematologic response and tolerance of the patient in order to obtain optimum therapeutic response with minimum adverse effects. While initial carboplatin dosage are based on body surface area, dosage may be more accurately calculated using formula dosing methods based on the patient's renal function.

Carboplatin decays in a biphasic manner after a 30-minute intravenous infusion of 300 to 500 mg/m 2. The initial plasma half-life (alpha) was found to be 1.1 to 2 hours (N=6), and the postdistribution plasma half-life (beta) was found to be 2.6 to 5.9 hours (N=6). The total body clearance, apparent volume of distribution and mean residence time for carboplatin are 4.4 L/hour, 16 L and 3.5 hours, respectively. Platinum from carboplatin becomes irreversibly bound to plasma proteins and is slowly eliminated with a minimum half-life of 5 days.

In practicing the present invention, one skilled in the art would know that superantigen therapy could be sequentially administered in combination with carboplatin, for example, by first treating with carboplatin. Once the effective cytostatic concentration of carboplatin has dropped in the patient below a functional inhibitory level, the superantigen can be administered to the patient.

c) Oxaliplatin

Oxaliplatin (Eloxatin®) organoplatinum complex in which the platinum atom is complexed with 1,2-diaminocyclohexane (DACH) and with an oxalate ligand as a leaving group (Scheeff E D, Briggs J M, Howell S B. Molecular modeling of the intrastrand guanine-guanine DNA adducts produced by cisplatin and oxaliplatin. Mol Pharmacol. 1999; 56:633-643).

Oxaliplatin is administered by infusion into a vein over at least 2 hours by a health care professional. It is typically given as one dose (85 mg/m2) every 2 weeks, along with other drugs (e.g., 5-fluorouracil and leucovorin). This cycle is repeated every 2 weeks. The dose and frequency is based on the blood count and response to previous doses of the subject. The terminal half life is about 273±19 h.

In practicing the present invention, one skilled in the art would know that superantigen therapy could be sequentially administered in combination with oxaliplatin, for example, by first treating with oxaliplatin. Once the effective cytostatic concentration of oxaliplatin has dropped in the patient below a functional inhibitory level, the superantigen can be administered to the patient.

B. Radiotherapy

In further embodiments, it is envisioned that the superantigen therapy of the present invention can be used in combination with radiotherapy. X-rays, γ-rays, and/or the directed delivery of radioisotopes to tumor cells have been commonly used to treat hyperproliferative disease, more specifically cancer. It is known that these factors cause DNA damage.

Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Thus, in further embodiments, it is envisioned that the superantigen therapy of the present invention can be used in combination with surgery to treat a cancer.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anticancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

D. Targeted Molecules Including Antibodies

In further embodiments, it is envisioned that the supeantigen therapy of the present invention can be used in combination with targeted molecules including, but not limited to, antibodies. For example, an antibody specific for some marker on the surface of a tumor cell. For example, the antibody alone may serve as an effector of therapy or it may recruit other cells to actually effect cell killing. The antibody also may be conjugated to a drug or toxin (e.g., a chemotherapeutic, a radionuclide, a ricin A chain, a cholera toxin, a pertussis toxin, etc.) and serve merely as a targeting agent. Such antibody conjugates are called immunotoxins, and are well known in the art (see U.S. Pat. No. 5,686,072, U.S. Pat. No. 5,578,706, U.S. Pat. No. 4,792,447, U.S. Pat. No. 5,045, 451, U.S. Pat. No. 4,664,911, and U.S. Pat. No. 5,767,072, each incorporated herein by reference).

Preferably, human monoclonal antibodies are employed in passive immunotherapy, as they produce few or no side effects in the patient. For example, such antibodies have been developed by ImClone Systems Incorporated. Antibodies to growth factors include, IMC-11F8 (similar to ERBITUX™), C225 (ERBITUX™), Panitumumab, HERCEPTIN®, IMC-A12 (targets insulin-like growth factor-1 receptor (IGF-1R)), IMC-18F1 (targets vascular endothelial growth factor receptor-1(VEGFR-1 or flt-1)). Antibodies to angiogensis inhibitors include IMC-1121b (targets vascular endothelial growth factor receptor-2 (VEGFR-2) or Avastin. Antibodies to other cell surface structures include Rituximab (targets CD20).

In another aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

E. Genetic Therapy Agents

A tumor cell resistance to agents, such as chemotherapeutic and radiotherapeutic agents, represents a major problem in clinical oncology. One goal of current cancer research is to find ways to improve the efficacy of one or more anti-cancer agents by combining such an agent with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that gene therapy could be used similarly in conjunction with the superantigen therapy.

F. Other Anticancer agents

It is contemplated that other agents may be used in combination with the superantigens to improve the therapeutic efficacy of treatment. These additional agents include immunomodulatory agents, agents that affect the upregulation of cell surface receptors and GAP junctions, cytostatic and differentiation agents, inhibitors of tyrosine kinases including epidermal growth factor receptor inhibitors, inhibitors of cell adehesion, or agents that increase the sensitivity of the hyperproliferative cells to apoptotic inducers. Immunomodulatory agents include tumor necrosis factor; interferon alpha, beta, and gamma; IL-2, linomide, and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases intercellular signaling by elevating the number of GAP junctions would increase the anti-hyperproliferative effects on the neighboring hyperproliferative cell population.

In other embodiments, cytostatic or differentiation agents can be used in combination with the present invention to improve the anti-hyerproliferative efficacy of the treatments. Inhibitors of tyrosine kinases include small molecules that act as inhibitors of epidermal growth factor receptor (EGFR) tyrosine kinase, such as ZD1839 (IRESSA®), OSI-774 (TARCEVA™) and passive antibodies (also discussed above as immune therapy) such as EGFR-blocking antibodies C225 (ERBITUX™) ABR-EGF, IMC-11F8, and HERCEPTIN®, split kinase inhibitors, such as PTK787/ZK 222584, SU11248, CP 549,632, and AG013736, and other inhibitors of tyrosine kinase, such as Imatinib (GLEEVEC®), MLN-518, CEP-701, PKC-412 (see Laird & Cherrington (2003), which is incorporated herein by reference in its entirety). Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy. Other agents include OSI-7904, Lapatinib, VELCADE®, and Sorafenib.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment can be used in in combination with the superantigen therapy of the present invention to reduce the risk of metastases.

V. COMBINATION HYPERPROLIFERATIVE DISEASE THERAPY

The present invention describes the treatment of a hyperproliferative disease, the reduction of a neoplasm or tumor, and/or the reduction of a metastatic tumor by administering to a subject in need a superantigen in combination with at least one anticancer agent, more preferable a chemotherapeutic agent.

A. Types of Hyperproliferative Diseases

The invention may be used in the treatment and prevention of hyperproliferative diseases including, but not limited to, cancer. A hyperproliferative disease is any disease or condition which has, as part of its pathology, an abnormal increase in cell number. Included in such diseases are benign conditions such as benign prostatic hypertrophy and ovarian cysts. Also included are premalignant lesions, such as squamous hyperplasia. At the other end of the spectrum of hyperproliferative diseases are cancers. A hyperproliferative disease can involve cells of any cell type. The hyperproliferative disease may or may not be associated with an increase in size of individual cells compared to normal cells.

Another type of hyperproliferative disease is a hyperproliferative lesion, a lesion characterized by an abnormal increase in the number of cells. This increase in the number of cells may or may not be associated with an increase in size of the lesion. Examples of hyperproliferative lesions that are contemplated for treatment include benign tumors and premalignant lesions. Examples include, but are not limited to, squamous cell hyperplastic lesions, premalignant epithelial lesions, psoriatic lesions, cutaneous warts, periungual warts, anogenital warts, epidermdysplasia verruciformis, intraepithelial neoplastic lesions, focal epithelial hyperplasia, conjunctival papilloma, conjunctival carcinoma, or squamous carcinoma lesion. The lesion can involve cells of any cell type. Examples include keratinocytes, epithelial cells, skin cells, and mucosal cells.

Preneoplastic or hyperplastic states which may be treated or prevented using the combination treatment of the present invention include but are not limited to preneoplastic or hyperplastic states such as colon polyps, Crohn's disease, ulcerative colitis, breast lesions and the like.

Cancers which may be treated using the pharmaceutical composition of the present invention include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like. Still further, the cancer that may be treated by administering a targetted-superantigen and chemotherapeutic agent can be defined based upon the body location and/or system, for example, but not limited to bone (e.g., Ewing's Family of tumors, osteosarcoma); brain (e.g., adult brain tumor, (e.g., adult brain tumor, brain stem glioma (childhood), cerebellar astrocytoma (childhood), cerebral astrocytoma/malignant glioma (childhood), ependymoma (childhood). Medulloblastoma (childhood), supratentorial primitive neuroectodermal tumors and pineoblastoma (childhood), visual pathway and hypothalamic glioma (childhood) and childhood brain tumor (other)); breast (e.g., breast cancer, breast cancer and pregnancy, male breast cancer); digestive/gastrointestinal (e.g., anal cancer, bile duct cancer (extrahepatic), carcinoid tumor (gastrointestinal), colon cancer, esophageal cancer, gallbladder cancer, liver cancer (adult primary), liver cancer (childhood), pancreatic cancer, small intestine cancer, stomach (gastric) cancer); endocrine (e.g., adrenocortical carcinoma, carcinoid tumor (gastrointestinal), islet cell carcinoma (endocrine pancreas), parathyroid cancer, pheochromocytoma, pituitary tumor, thyroid cancer); eye (e.g., melanoma (intraocular), retinoblastoma); genitourinary (e.g., bladder cancer, kidney (renal cell) cancer, penile cancer, prostate cancer, renal plvis and ureter cancer (transitional cell), testicular cancer, urethral cancer, Wilms' Tumor and other childhood kidney tumors); germ cell (e.g., extracranial germ cell tumor (childhood), extrgonadal germ cell tumor, ovarian germ cell tumor, testicular cancer); gynecologic (e.g., cervical cancer, endometrial cancer, gestational trophoblastic tumor, ovarian epithelial cancer, ovarian germ cell tumor, ovarian low malignant potential tumor, uterine sarcoma, vaginal cancer, vulvar cancer); head and neck (e.g., hypopharyngeal cancer, laryngeal cancer, lip and oral cavity cancer, metastatic squamous neck cancer with occult primary, nasopharyngeal cancer, oropharyngeal cancer, paranasal sinus and nasal cavity cancer, parathyorid cancer, salivary gland cancer): lung (e.g., non-small cell lung cancer, small cell lung cancer); lymphoma (e.g., AIDS-Related Lymphoma, cutaneous T-cell lymphoma, Hodgkin's Lymphoma (adult), Hodgkin's Lymphoma (childhood), Hodgkin's Lymphoma during pregnancy, mycosis fungoides, Non-Hodgkin's Lymphoma (adult), Non-Hodgkin's Lymphoma (childhood), Non-Hodgkin's Lymphoma during pregnancy, primary central nervous system lymphoma, Sezary Syndrome, T-cell lymphoma (cutaneous), Waldenström's Macroglobulinemia); musculoskeletal (e.g., Ewing's Family of tumors, osteosarcoma/malignant fibrous histiocytoma of bone, rhabdomyosarcoma (childhood), soft tissue sarcoma (adult), soft tissue sarcoma (childhood), uterine sarcoma); neurologic (e.g., adult brain tumor, childhood brain tumor (e.g., brain stem glioma, cerebellar astrocytoma, cerebral astrocytoma/malignant glioma, ependymoma, medulloblastoma, supratentorial primitive neuroectodermal tumors and pineoblastoma, visual pathway and hypothalamic glioma, other brain tumors), neuroblastoma, pituitary tumor primary central nervous system lymphoma); pregnancy and cancer (e.g., breast cancer and pregnancy, Hodgkin's lymphoma during pregnancy, Non-Hodgkin's lymphoma during pregnancy); respiratory/thoracic (e.g., non-small cell lung cancer, small cell lung cancer, malignant mesothelioma, thymoma and thymic carcinoma); and skin (e.g., cutaneous T-cell lymphoma, Kaposi's sarcoma, melanoma, merkel cell carcinoma, skin cancer).

Cancers that may be treated using the combination of the present invention (targeted-superantigen and a chemotherapeutic agent) may also be defined based upon the chemotherapeutic agent that is known to treat the cancer, for example, but not limited to alkylating agents (e.g., Hodgkin's disease, lymphomas, and certain carcinomas of the lung, breast, prostate and ovary cancer); nitrosoureas (e.g., brain tumors, lymphomas, multiple myeloma, and malignant melanoma); antimetabolites (e.g., choriocarcinoma, and some tumors of the gastrointestinal tract, breast, lung, kidney and ovary); antitumor antibiotics (e.g., lymphomas, breast, ovarian, endometrium, prostate and gastrointestinal); mitotic inhibitors (e.g., certain gastro-intestinal cancers, Hodgkin's and non-Hodgkin's lymphomas, neuroblastomas, Wilms' tumor, and cancers of the lung, breast, prostate and testes); platinum based compounds (e.g. cancer of the lung, breast, ovary, bladder, head and neck and certain gastrointestinal) and targeted/other therapies (renal, prostate, gastrointestinal, lymphomas, non-hodgkin-lymphoma, breast, lung, myeloma).

Yet further, the cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a renal cancer cell, an ovarian cancer cell, a lymphatic cancer cell, a skin cancer cell, a brain cancer cell, a bone cancer cell, or a soft tissue cancer cell.

Other hyperproliferative diseases that may be treated using the combination treatment of the present invention include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In a preferred embodiment of the present invention, the combination of the tumor-targeted superantigen and at least one anticancer agent, for example a cystostatic agent or a radiotherapeutic agent, are administered in an effective amount to decrease, reduce, inhibit or abrogate the growth of a solid tumor. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Yet further, cancers that are most likely to be treated in the present invention are those that metastasize. It is understood by those in the art that metastasis is the spread of cells from a primary tumor to a noncontiguous site, usually via the bloodstream or lymphatics, which results in the establishment of a secondary tumor growth. Examples cancers contemplated for treatment include, but are not limited to melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, bone, testicular, ovarian, mesothelioma, cervical, gastrointestinal lymphoma, brain, or colon cancer and any other tumors or neoplasms that may be treated by administering in combination a tumor-targeted superantigen and at least one cytostatic agent.

Still further, the present invention can also be used to treat tumors in sheaths ("theca") encasing organs. Examples include (1) pleural effusion due to fluid in the pleural sheath surrounding the lung, (2) ascites originating from fluid accumulating in the peritoneal membrane and (3) cerebral edema due to metastatic carcinomatosis of the meninges. Such effusions and fluid accumulations generally develop at an advanced stage of the disease. Malignant pleural effusion ("MPE") is the prototype of this condition.

B. Therapeutic Amounts

As used herein the terms "effective amount" or "dose" or "therapeutic dose" are defined as an amount of the agent that will decrease, reduce, inhibit or otherwise abrogate the growth or proliferation of a cancer cell, induce apoptosis, inhibit angiogenesis of a tumor cell, inhibit metastasis, or induce cytotoxicity in cells. The effective amount of active compound(s) used to practice the present invention for therapeutic treatment of neoplasms (e.g., cancer) varies depending upon the manner of administration, the age, body weight, and general health of the subject. It is within the skill in the art for an attending physician or veterinarian to determine the appropriate amount and dosage regimen. Such amounts may be referred to as an "effective" amounts. These terms include synergistic situations such as those presented and described in the instant invention wherein a single agent alone, such as a superantigen or an anticancer agent such as a cytostatic agent, may act weakly or not at all, but when combined with each other, for example, but not limited to, via sequential dosage, the two or more agents act to produce a synergistic result.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, for example, but not limited to, TTS administration, the effective amount or dose of the superantigen that is administered is an amount in the range of 0.01 to 500 μg/kg body weight of the subject, preferably 0.1-500 μg/kg body weight of the subject, and most preferably 1-100 μg/kg body weight of the subject. In certain embodiments where wild-type superantigens and/or unconjugated/fused and/or unmodified superantigens are used, the effective amount or does of the superantigen that is to be administered is in an amount in the range of 0.001 to 500 μg/kg body weight of the subject.

It is envisioned that the effective amount or dose of the anticancer agent (e.g., a cytostatic agent and/or radiotherapeutic agent) that is administered in combination with the superantigen is a dose that results in a synergistic anti-tumor effect and does not interfere or inhibit the enhancement of the immune system or T-cell activation. Thus, one of skill in the art is aware that the dose and/or timing of the dose may be altered depending upon the therapeutic regimen. For example, the dose of the anticancer agent (e.g., cytostatic agent and/or radiotherapeutic agent) may be considered a high dose or "anti-proliferative dose" and is administered prior to and/or subsequent to the superantigen administration. This type of regiment considers the half-life of the anticancer agent. If the anticancer agent is administered simultaneously with the superantigen, then the anticancer agent may be administered in a low dose such that it does not interfere with the mechanism of action of the superantigen.

C. Treatment Regimens

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician may often be best suited to make such decisions based on his or her skill in the art and the known efficacy and toxicity (if any) of the therapeutic formulations.

Preferably, patients to be treated will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

To kill cells, inhibit cell growth, inhibit metastasis, decrease tumor or tissue size and otherwise reverse or reduce the malignant phenotype of tumor cells, using the methods and compositions of the present invention, one would generally contact a tumor cell or neoplasm or cancer cell with a combination of a superantigen and at least one anticancer agent, such as a cytostatic agent and/or a radiotherapeutic agent. The routes of administration will vary, naturally, with the location and nature of the lesion, and include, e.g., intradermal, transdermal, parenteral, intravenous, intrathecal, intramuscular, intranasal, subcutaneous, percutaneous, intratracheal, intraperitoneal, intratumoral, perfusion, lavage, direct injection, and oral administration and formulation.

In one aspect of the present invention, the tumor cell or neoplasm or cancer cell must bear some marker that is amenable to targeting, e.g., is not present on the majority of other cells. Many tumor markers exist and any of these may be suitable for targeting in the context of the present invention. The selection of a suitable marker is will within the skill of one in the art and skill in the related art. Specific targeting agents of the present invention include, e.g., antibodies. The antibodies that are contemplated in the present invention include, but are not limited to the Fab fragment. Examples of the Fab fragment include C215Fab or 5T4Fab. In addition to Fab, other common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In certain embodiments, the treatment regimen of the present invention may involve contacting the neoplasm or tumor cells with the superantigen and the cytostatic agent at the same time. This may be achieved by contacting the cell with a single composition or pharmacological formulation that includes both agents, or by contacting the cell with two distinct compositions or formulations, at the same time, wherein one composition includes the superantigen and the other includes the anticancer agent, such as a cytostatic agent.

Alternatively, the superantigen of the present invention may precede or follow the anticancer agent by intervals ranging from minutes, days to weeks. In embodiments where the other anticancer agent and the superantigen are applied separately to the cell, one would generally ensure that a significant period of time did not expire between the time of each delivery, such that the superantigen and anticancer agent would still be able to exert an advantageously combined effect on the cell. In such instances, it is contemplated that one may contact the cell with both modalities within about 12-72 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the superantigen is "A" and the anticancer agent, is "B":

A/B/A B/A/B B/B/A A/A/B A/B/B B/A/A A/B/B/B;
B/A/B/B B/B/B/A B/B/A/B A/A/B/B A/B/A/B A/B/B/A;
B/B/A/A B/A/B/A B/A/A/B A/A/A/B B/A/A/A A/B/A/A; and
A/A/B/A.

The terms "contacted" and "exposed," as used herein means when applied to a cell, are used herein to describe the process by which the superantigen and a cytostatic agent or a radiotherapeutic agent are delivered to a target cell or are placed in direct juxtaposition with the target cell. To achieve cell killing or stasis, both agents are delivered to a cell in a combined amount effective to kill the cell or prevent it from dividing. This delivery may be sequentially timed as described herein.

Timing of the therapeutic regimen may be related to the half-live of the anticancer agent, such as a cytostatic agent. Half-life of a cytostatic agent can be determined using the below equation $$\text{Half-Life} = (0.693 \times V_d)/CL$$

CL is defined as the clearance of the agent or drug clearance, which is the volume of plasma cleared of drug per unit time. $V_d$ is defined as the volume of distribution, which is the amount or concentration of the agent in the plasma or blood to the total amount in the body. The half-life can be used to determine the timing for sequential administration of a cytostatic agent followed by superantigen therapy. Thus, in practicing the present invention, one skilled in the art would know that superantigen therapy could be sequentially administered in combination with a cytostatic, for example, by first treating with the cytostatic agent. Once the effective cytostatic concentration of agent has dropped in the patient below a functional inhibitory level based upon the half-life of the agent, the superantigen can be administered to the patient.

It is further envisioned that the present invention can be used in combination with surgical intervention. In the case of surgical intervention, the present invention may be used preoperatively, e.g., to render an inoperable tumor subject to resection. Alternatively, the present invention may be used at the time of surgery, and/or thereafter, to treat residual or metastatic disease. For example, a resected tumor bed may be injected or perfused with a formulation comprising the tumor-targeted superantigen and/or the anticancer agent (e.g., a cytostatic agent or a radiotherapeutic agent). The perfusion may be continued post-resection, for example, by leaving a catheter implanted at the site of the surgery. Periodic post-surgical treatment also is envisioned. Any combination of the invention therapy with surgery is within the scope of the invention.

Continuous administration also may be applied where appropriate, for example, where a tumor is excised and the tumor bed is treated to eliminate residual, microscopic disease. Delivery via syringe or cauterization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

In certain embodiments, the tumor being treated may not, at least initially, be resectable. Treatments with superantigen in combination with at least one anticancer agent may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, may involve multiple doses. Typical primary tumor treatment may involve a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

As used in the present invention, a combination treatment regimen consists of administering a superantigen and at least one anticancer agent, for example a cytostatic drug or a radiotherapeutic agent. Yet further, it may be desirable to combine the combination treatment regimen with other agents effective in the treatment of neoplastic diseases or cancers, such as other anticancer agents, such as other include biological agents (biotherapy) and/or hormonal therapy, etc.

Included within the scope of the present invention is the systemic (e.g., via intravenous (iv) administration) of superantigens, for example TTS, and/or anti-cancer agents, for example chemotherapeutic drugs, for example cytostatic drugs. Also included is the local administration (e.g., via direct administration of the agent to the tumor, for example by intrathecal administration) of superantigens, for example TTS, and/or anti-cancer agents, for example chemotherapeutic drugs, for example cytostatic drugs. Also included is the combination of local and systemic administration of superantigens, for example TTS, and/or anti-cancer agents, for example chemotherapeutic drugs, for example cytostatic drugs (for example, systemic administration of superantigens (e.g., TTS) combined with local administration of an anticancer agent (e.g., a chemotherapeutic drug) and vice versa).

VI. COMBINED THERAPY

As used herein, the term "sequential dosage" and related terminology refers to the administration of at least one superantigen, with at least one anticancer agent, for example, but not limited to a chemotherapeutic agent, such as but not limited to a chemotherapeutic drug, such as but not limited to cytostatic chemotherapeutic drug. This definition includes staggered doses of these agents and variations in dosage amounts. This includes one agent being administered before, overlapping with (partially or totally), after, or totally separate from another agent. This term generally considers the best administration scheme to achieve a synergistic combination of at least one superantigen and at least one anticancer agent and/or to achieve administration of at least one superantigen while limiting or eliminating the generation of an antibody response to the superantigen. Determining sequential dosage administration plans is within the skill of one in the art, from the background skill and teaching in the art and the teaching of this application. For example, one of skill in the art, e.g., based on known drug half-lifes, is able to determine when an anticancer agent or cytostatic agent is below a functional inhibitory level. A functional inhibitory level of the anti-cancer agent is determined based upon the agent's half-life. Thus, a skilled artisan would know that in order for the superantigen therapy to be effective it must be administered after the cytostatic agent is below a functional inhibitory level.

Typically, one of skill in the art considers chemotherapy and radiotherapy to have anti-proliferative properties, and therefore would generally be expected to interfere with immune stimulating agents such as tumor vaccines, biological response modifiers and superantigens. The present invention utilizes the combination of these known anti-proliferative therapies in combination with a known immune stimulatory or proliferative agent.

It is well documented that certain drugs may also have immune-stimulatory properties when administered at low (sub-toxic) doses (reviewed by Zagozdzon and Golab, 2001; Mitchell, 2003). However, the inventors of the present invention have provided an intergrated high dose cytostatic agent/immunotherapy treatment. The prerequisites of an integrated high dose cytostatic drug/immunotherapy treatment relate to distinct time frames for the activity of the agents. The cytostatic agent should act within a certain time frame and the same is necessary for the immunotherapy.

Most cytostatic drugs act during a short period of high drug exposure, and elimination of the drug generally occurs within 24 hours after administration. Typically, serum half-lifes of the commonly used drugs gemcitabine and docetaxel are 42-94 minutes and 11.1 hours respectively. Other half-lifes and half-live determinations are discussed above, which is incorporated herein.

The immunotherapy though is generally dependent on a long period of immune activation with unpredicted phases of lymphocyte proliferation. Thus, the initiation of an antigen specific immune response, e.g., during vaccination, depends on a number of time limiting processes, such as targeting of antigen to lymphoid organs, uptake and presentation on antigen presenting cells etc. Also, the duration of the response may vary considerably, depending on the persistency of antigen in the circulation.

The immunotherapy of superantigens results in rapid (within hours) and powerful polyclonal activation of T lymphocytes. A superantigen treatment cycle commonly includes 4 to 5 daily intravenous superantigen drug injections. Such treatment cycles can be given in e.g., 4 to 6 weeks intervals. Non-clinical studies show a nearly instant T lymphocyte activation and proliferation and rapid inflammation by cytotoxic T lymphocytes (CTLs) into tumor tissue as a response to the first injection of the superantigen drug (Dohlsten et al, 1995). The inflammation with infiltration of CTLs into the tumor is one of the major effectors of the anti-tumor therapeutic superantigens. After a short period of massive activation and differentiation of CTLs, the T-cell response declines rapidly (within 4-5 days) back to base line levels. Thus, the period of lymphocyte proliferation, during which cytostatic drugs may interfere with superantigen treatment is short and well-defined. Only with the superantigen/anti-cancer agent therapy of the instant invention is such a distinct time frame for activity plausible, thereby allowing the novel integrated high dose cytostatic agent/immunotherapy treatment.

The cytostatic drugs and the immunotherapy superantigens represent types of anti-tumor therapies with distinct mechanisms of action potentially not possible to timely integrate and should therefore not be additive. Surprisingly though, by combining high dose cytostatic drugs with superantigens in integrated treatment schedules synergistic anti-tumor effects are obtained. Thus, in a general combination therapy schedule superantigen treatment may be integrated with one or more standard chemotherapy (at well established standard doses) in such a way that superantigen is given shortly (e.g., within 0-3 days or, e.g., 0-6 days) before or after administration of the cytostatic drug.

Administration of the immunotherapy of the present invention to a patient will follow general protocols for the administration of chemotherapeutics. It is expected that the treatment cycles would be repeated as necessary. It also is contemplated that various standard therapies, as well as surgical intervention, may be applied in combination with the described neoplastic cell therapy.

In addition to the combination of the superantigen and cytostatic agent having a synergistic anti-tumor effect, the cystostatic agent modulates or inhibits production of antibodies to superantigens The superantigen fusion proteins are immunogenic and antibodies are produced. These bind to the superantigen protein and are an obstacle for superantigen activity. Primary antibody responses are not productive until after about one week post stimulation. Secondary antibody responses usually have their maximal B cell proliferative phase approximately 5-7 days after stimulation.

Antibodies interfering with the superantigen proteins compromise anti-tumor therapeutic effects. Therefore the instant combination treatment that results in no, or fewer anti-superantigen antibodies in a patient makes multi-cycle superantigen treatment possible.

VII. KITS

Embodiments of the present invention include kits comprising, for example, a first container having a tumor-targeted superantigen and a second container having at least one anti-cancer agent, such as a chemotherapeutic agent, such as a cytostatic agent.

Any of the compositions described herein may be comprised in a kit. In a non-limiting example, a kit may comprise a superantigen (for example, a TTS) and a cytostatic agent. Such a kit may also contain additional agents such as, for example, a lipid component.

The kits may comprise a suitably aliquoted a superantigen and/or a cytostatic agent, and optionally, lipid and/or additional agent compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in one or more vials. The kits of the present invention also will typically include a means for containing the a superantigen and/or a cytostatic agent, lipid, additional agent, and any other reagent containers in close confinement for commercial sale. Such containers may include injection or blow molded plastic containers into which the desired vials are retained.

Therapeutic kits of the present invention will generally contain, in suitable container means, a pharmaceutically acceptable formulation of a superantigen and an anti-cancer agent in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The a superantigen and an anti-cancer agent may also be formulated into a syringeable composition. In which case, the container means may itself be a syringe, pipette, and/or other such like apparatus, from which the formulation may be applied to a specific area of the body, injected into an animal, and/or applied and/or mixed with the other components of the kit.

The components of the kit may be provided as dried powder(s). When reagents and/or components are provided as a dry powder, the powder can be reconstituted by the addition of a suitable solvent. It is envisioned that the solvent may also be provided in another container means.

The container will generally include at least one vial, test tube, flask, bottle, syringe and/or other type for holding a sample, into which the a superantigen, and/or an anti-cancer agent are placed, e.g., suitably allocated. The kits may also comprise another container for containing a sterile, pharmaceutically acceptable buffer and/or other diluent.

The kits of the invention may also comprise, and/or be packaged with, an instrument for assisting with the injection/administration and/or placement of the ultimate therapeutic composition, e.g., a superantigen and a cytostatic agent, within the body of an animal. Such an instrument may be a syringe, pipette, forceps, and/or any such medically approved delivery vehicle.

VIII. PHARMACEUTICAL COMPOSITIONS

The combined superantigen and anti-cancer agents of the present invention may be employed alone or in conjunction with other compounds, such as carriers or other therapeutic compounds.

Pharmaceutical compositions of the present invention comprise an effective amount of one or more superantigens and one or more anti-cancer agents, for example a chemotherapeutic agent, such as a cytostatic agent, and may also contain additional agents, dissolved or dispersed in a pharmaceutically acceptable carrier. The phrases "pharmaceutical or pharmacologically acceptable" refer to substances, e.g., compositions, that do not produce an adverse, allergic or other untoward reaction when administered to a mammal, such as, for example, a human. The preparation of a pharmaceutical composition that contains at least one superantigen and an anti-cancer agent will be known to those of skill in the art in light of the present disclosure, and as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes, e.g., solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The superantigens and anti-cancer agents may comprise different types of carriers depending on whether they are to be administered in solid, liquid or aerosol form, and whether it need to be sterile for such routes of administration as injection. The present invention may possibly be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The superantigens and anti-cancer agent may be formulated into a composition in a free base, neutral or salt form. Pharmaceutically acceptable salts include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, e.g., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various anti-bacterial and antifungal agents, including but not limited to parabens (e.g., methylparabens, propylparabens), chlorobutanol, phenol, sorbic acid, thimerosal or combinations thereof.

In accordance with the present invention, the composition is combined e.g., a carrier in any convenient and practical manner, e.g., by solution, suspension, emulsification, admixture, encapsulation, absorption and the like. Such procedures are routine for those skilled in the art.

In a specific embodiment of the present invention, the composition is combined and/or mixed thoroughly with a semi-solid or solid carrier. The mixing can be carried out in any convenient manner such as grinding. Stabilizing agents can be also added in the mixing process in order to protect the composition from loss of therapeutic activity, e.g., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include may superantigens and/or an anti-cancer agent, as well as, one or more lipids, and an aqueous solvent. As used herein, the term "lipid" will be defined to include any of a broad range of substances that are characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (e.g., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

Those of ordinary skill in the art are familiar with the range of techniques that can be employed for dispersing a composition in a lipid vehicle. For example, the superantigens and/or a anti-cancer agents may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can routinely be determined by one of skill in the art by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject. Such determinations are known and used by those of skill in the art.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. Such determinations are known and used by those of skill in the art.

A. Alimentary Compositions and Formulations

In some embodiments of the present invention, the superantigens and/or an anti-cancer agent such as a chemotherapeutic agent, such as a cytostatic drug may be formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, superantigens and/or an anti-cancer agent (e.g., a chemotherapeutic agent, such as a cytostatic drug) may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, intratumorally, subcutaneous, or intraperitoneally U.S. Pat. Nos. 6,613,308, 5,466,468, 5,543, 158; 5,641,515; 5,399,363 and International Publication WO03094846 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other embodiments of the invention, superantigens and/or an anti-cancer agent (e.g, a chemotherapeutic agent, such as a cytostatic drug) may be formulated for administration via various miscellaneous routes, for example, topical (e.g., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch." For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Tumor Targeted Superantigens

The fusion protein C215Fab-SEA (SEQ. ID. NO. 5) (sometimes referred to herein as "ABR-214720"), consisting of Staphylococcal Enterotoxin A genetically fused to the Fab moiety of an antibody (C215) recognizing an epitope of the human tumor associated antigen EpCAM/GA733-2, was expressed in E. coli (Dohlsten et. al., 1994) and purified as described by Forsberg et al., 1997. Other fusion proteins that may be used include 5T4Fab-SEA/E-120 (SEQ. ID. NO. 7) (sometimes referred to herein as "ABR-217620"), and 5T4Fab-SEA$_{D227A}$ (SEQ. ID. NO. 6), which are produced as described by Forsberg et al., 1997.

Example 2

TTS-Chemotherapeutic (e.g., Gemcitabine, Docetaxel, Cisplatin) Agent Combination Therapy: In vitro Anti-Tumor The effect of superantigen (TTS) treatment (5T4Fab-SEA/E-120) in combination with cytostatics on tumor growth was assessed in vitro.

Cell Lines and Media

The human cancer cell line Colo 205 was cultured in RPMI 1640+10% FBS (R10 medium). The cells were prepared by detachment with cell dissociation solution, washed with PBS and resuspended in R10 medium. Peripheral blood mononuclear cells (PBMC) were obtained from blood donors. The PBMC were isolated by density centrifugation on Ficoll-Paque. The cells were then cultured in R10 medium and stimulated with TTS to obtain effector T-cell lines.

Inhibition of Tumor Growth

Tumor growth inhibition by TTS in combination with gemcitabine (GEMZAR®), docetaxel (TAXOTERE®), and cisplatin was measured by a tumor cell proliferation assay. The proliferation assay measures DNA synthesis of the tumor cells by incorporation of $^3$H-thymidine. The effector T cells were prevented from proliferating by pre-treatment of Mitomycin C. Tumor cells were first incubated with TTS and effector T cells for 4 hours in vitro. Cytostatics were then added for a total incubation time of 48 hours, followed by measurements of incorporated radioactive thymidine by liquid scintillation. The background level of incorporated radioactivity from wells of Mitomycin C-treated T cells alone ($\leqq$1% of the levels in cultures of untreated tumor cells) was subtracted.

$$\% \text{ of control} = \frac{\text{experimental value} - \text{background}}{\text{untreated tumor cells} - \text{background}} \times 100$$

Results

Treatment of the human Colo 205 tumor cells with activated T cells and ABR-217620 in the combination with gemcitabine (GEMZAR®), docetaxel (TAXOTERE®) or cisplatin as applied subsequent to the SADCC (Superantigen Antibody Dependent Cell mediated cytotoxicity) resulted in enhanced inhibition of tumor cell growth. Tables 2-4 depict proliferation of tumor cells as % of untreated control. Treatment with gemcitabine (GEMZAR®), docetaxel (TAXOTERE®) or cisplatin showed enhanced tumor growth inhibition in the combination with ABR-217620.

TABLE 2

Gemcitabine (GEMZAR ®) enhances tumor growth inhibition in the combination with ABR-217620.

| SADCC, 4 h | Chemo, 48 h | Effect on human tumor cell (Colo 205) proliferation, Percent of control |
|---|---|---|
| Vehicle | Vehicle | 100 |
| ABR-217620, 1 pM | Vehicle | 47 |
| Vehicle | Gemcitabine, 10 ng/ml | 16 |
| ABR-217620, 1 pM | Gemcitabine, 10 ng/ml | 7 |

TABLE 3

Docetaxel (TAXOTERE ®) enhances tumor growth inhibition in the combination with ABR-217620.

| SADCC, 4 h | Chemo, 48 h | Effect on human tumor cell (Colo 205) proliferation, Percent of control |
|---|---|---|
| Vehicle | Vehicle | 100 |
| ABR-217620, 1 pM | Vehicle | 47 |
| Vehicle | Docetaxel, 1 ng/ml | 46 |
| ABR-217620, 1 pM | Docetaxel, 1 ng/ml | 28 |

TABLE 4

Cisplatin enhances tumor growth inhibition in the combination with ABR-217620.

| SADCC, 4 h | Chemo, 48 h | Effect on human tumor cell (Colo 205) proliferation, Percent of control |
|---|---|---|
| Vehicle | Vehicle | 100 |
| ABR-217620, 1 pM | Vehicle | 47 |
| Vehicle | Cisplatin, 1 µg/ml | 25 |
| ABR-217620, 1 pM | Cisplatin, 1 µg/ml | 10 |

The above results showed that the combination of the chemotherapeutic agents gemcitabine (GEMZAR®), docetaxel (TAXOTERE®) or cisplatin with TTS enhanced the tumor growth inhibition induced by TTS.

Example 3

TTS-Chemotherapeutic Agent (e.g., Pemetrexed) Combination Therapy: In vitro Anti-Tumor The effect of superantigen (TTS) treatment (5T4Fab-SEA/E-120) in combination with cytostatics on tumor growth was assessed in vitro.

Cell Lines and Media

The human cancer cell line Colo 205 was cultured in RPMI 1640+10% FBS (R10 medium). The cells were prepared by detachment with cell dissociation solution, washed with PBS and resuspended in R10 medium. Peripheral blood mononuclear cells (PBMC) were obtained from blood donors. The PBMC were isolated by density centrifugation on Ficoll-Paque. The cells were then cultured in R10 medium and stimulated with TTS to obtain effector T-cell lines.

Inhibition of Tumor Growth

Tumor growth inhibition by TTS and pemetrexed (ALIMTA®) and the combination was measured by a cell viability test. The cell viability test measured the amount of ATP in the tumor cells using a luciferase-based assay. Tumor cells were first incubated with TTS and effector T cells for 4 hours in vitro. Pemetrexed was then added for a total incubation time of 48 hours, followed by measurements of the ATP content in the tumor cell cultures. The background level of ATP from wells of Mitomycin C-treated T cells alone ($\leqq$1% of the levels in cultures of untreated tumor cells) was subtracted.

$$\% \text{ of control} = \frac{\text{experimental value} - \text{background}}{\text{untreated tumor cells} - \text{background}} \times 100$$

Results

Treatment of the human Colo 205 tumor cells with activated T cells and ABR-217620 in the combination with pemetrexed (ALIMTA®) as applied subsequent to the SADCC (Superantigen Antibody Dependent Cell-mediated Cytotoxicity) resulted in enhanced inhibition of tumor cell growth. Table 5 depicts viability of tumor cells as % of untreated control. Treatment with pemetrexed (ALIMTA®) showed enhanced tumor growth inhibition in the combination with ABR-217620.

TABLE 5

Pemetrexed (ALIMTA ®) enhances tumor growth inhibition in the combination with ABR-217620.

| SADCC, 4 h | Chemo, 48 h | Effect on human tumor cell (Colo 205) viability, Percent of control |
|---|---|---|
| Vehicle | Vehicle | 100 |
| ABR-217620, 1 pM | Vehicle | 79 |
| Vehicle | Pemetrexed, 40 ng/ml | 78 |
| ABR-217620, 1 pM | Pemetrexed, 40 ng/ml | 60 |

The above results showed that the combination of the chemotherapeutic agent pemetrexed (ALIMTA®) with TTS enhanced the tumor growth inhibition induced by TTS.

Example 4

TTS-Chemotherapeutic Agent (e.g., Docetaxel) Combination Therapy: In vitro Anti-Tumor The effect of superantigen (TTS) treatment (5T4Fab-SEA/E-120) in combination with cytostatics on tumor cell killing was assessed in vitro.

Cell Lines and Media

The human cancer cell line Colo 205 was cultured in RPMI 1640+10% FBS (R10 medium). The cells were prepared by detachment with cell dissociation solution, washed with PBS and resuspended in R10 medium. Peripheral blood mononuclear cells (PBMC) were obtained from blood donors. The PBMC were isolated by density centrifugation on Ficoll-Paque. The cells were then cultured in R10 medium and stimulated with TTS to obtain effector T-cell lines.

Tumor Cell Killing by Superantigen Antibody Dependent Cell-mediated Cytotoxicity; SADCC To analyze anti-tumor activity of combinations of TTS (ABR-217620) and docetaxel (TAXOTERE®) in vitro a chromium-release assay was applied. The target cells in the cytotoxicity assay, human Colo 205 tumor cells, were first pre-treated with various concentrations of docetaxel for 16 hours, washed in medium and then labeled with $(Na)_2{}^{51}CrO_4$. The anti-tumor cytotoxicity (Superantigen Antibody Dependent Cell-mediated Cytotoxicity; SADCC) was then measured in the presence TTS and human activated effector T cells in a standard chromium release assay using 96-well plates. The percentage specific lysis was calculated according to the formula:

$$\% \text{ specific lysis} = \frac{\text{experimental release} - \text{spontaneous release}}{\text{total release} - \text{spontaneous release}} \times 100$$

Results

Figure 4:
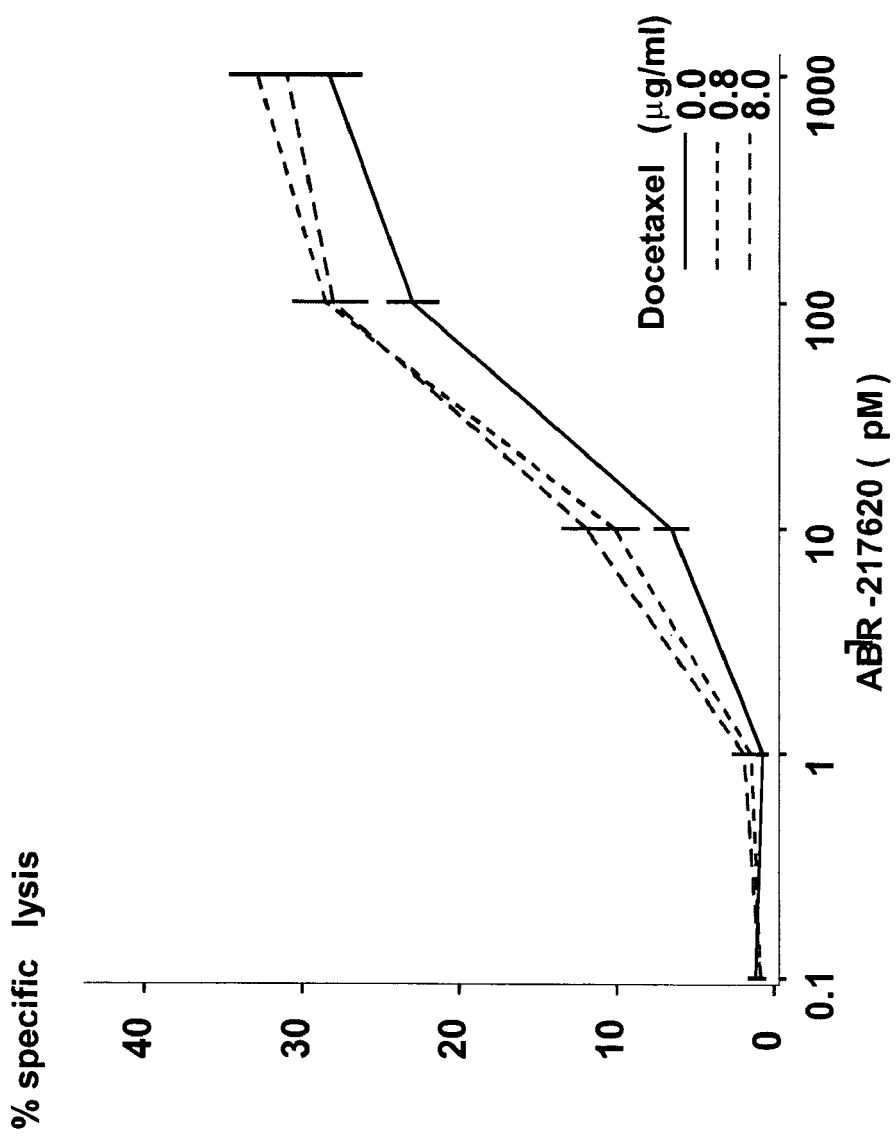
FIG. 4 shows that pre-treatment with docetaxel (TAXOTERE®) enhances tumor cell sensitivity for ABR-217620 induced SADCC.

Pre-treatment of the human Colo 205 tumor cells with docetaxel (TAXOTERE®) induced enhanced sensitivity for activated T cells and ABR-217620, Superantigen Antibody Dependent Cell-mediated Cytotoxicity; SADCC. FIG. 4 depicts killing of tumor cells as % specific lysis with various concentrations of ABR-217620 and activated T cells. Pre-treatment with docetaxel (TAXOTERE®) showed enhanced tumor cell killing as compared to control tumor cells.

The results showed that the combination of the chemotherapeutic agent docetaxel (TAXOTERE®) as sequential pre-treatment together with TTS enhanced the tumor cell killing induced by TTS.

Example 5

TTS-Chemotherapeutic (e.g., Gemcitabine) Combination Therapy: In vivo Examples of Systemic Immune Activation in Mice The systemic immune response was evaluated in C57B1/6 mice following treatment with C215Fab-SEA in combination with the chemotherapeutic agent gemcitabine.

Animals

Female C57B1/6 mice were used. The mice were routinely used at the age of 8 to 12 weeks and received food and water ad libitum.

Cell Lines and Media

The murine B-cell lymphoma cell line A20 (ATCC, TIB-208) was maintained in RPMI 1640 with ultraglutamine supplemented with 10% FCS, 1 mM sodium pyruvate, 50 μM β-mercaptoethanol and 0.1 mg/ml gentamicin.

Treatment of Mice

C215Fab-SEA treatment was given as daily i.v. injections (10 μg/mouse, in 0.2 ml PBS containing 1% mouse serum) for 3 consecutive days. For combination studies, four doses of gemcitabine were injected i.p. with three days interval before C215Fab-SEA therapy. Three mice were included in each experimental group. 48 hours after the last C215Fab-SEA injection mice were sacrificed and the spleens were removed for analysis of cell dynamics and cytotoxic activity.

Flow Cytometry

Single cell suspensions of splenocytes from mice injected with indicated substances were prepared. Erythrocytes were removed by hypotonic shock using Gey's solution. The remaining lymphocytes were stained for cell surface antigen expression for 30 min on ice after blocking of Fc-receptors by CD32/CD16 antibodies. Where biotinylated mAbs were used, cells were stained with streptavidin-tricolor. Cells were washed twice in PBS+1% BSA after each staining step. The samples were analysed in a FACSort flow cytometer.

Cytotoxicity Assays

Mice treated with indicated substances were sacrificed 48 h after the last injection and the spleens were removed. Cytotoxicity of bulk splenocytes was measured against SEA coated (1 μg/ml) A20 cells using a standard $^{51}Cr$ release assay (Dohlsten et al., 1990; Hedlund et al, 1993). The effector to target cell ratio was 100:1. Calculations were carried out according to the formula:

$$\% \text{ specific lysis} = \frac{\text{experimental release} - \text{spontaneous release}}{\text{total release} - \text{spontaneous release}} \times 100$$

Results

Figure 5:
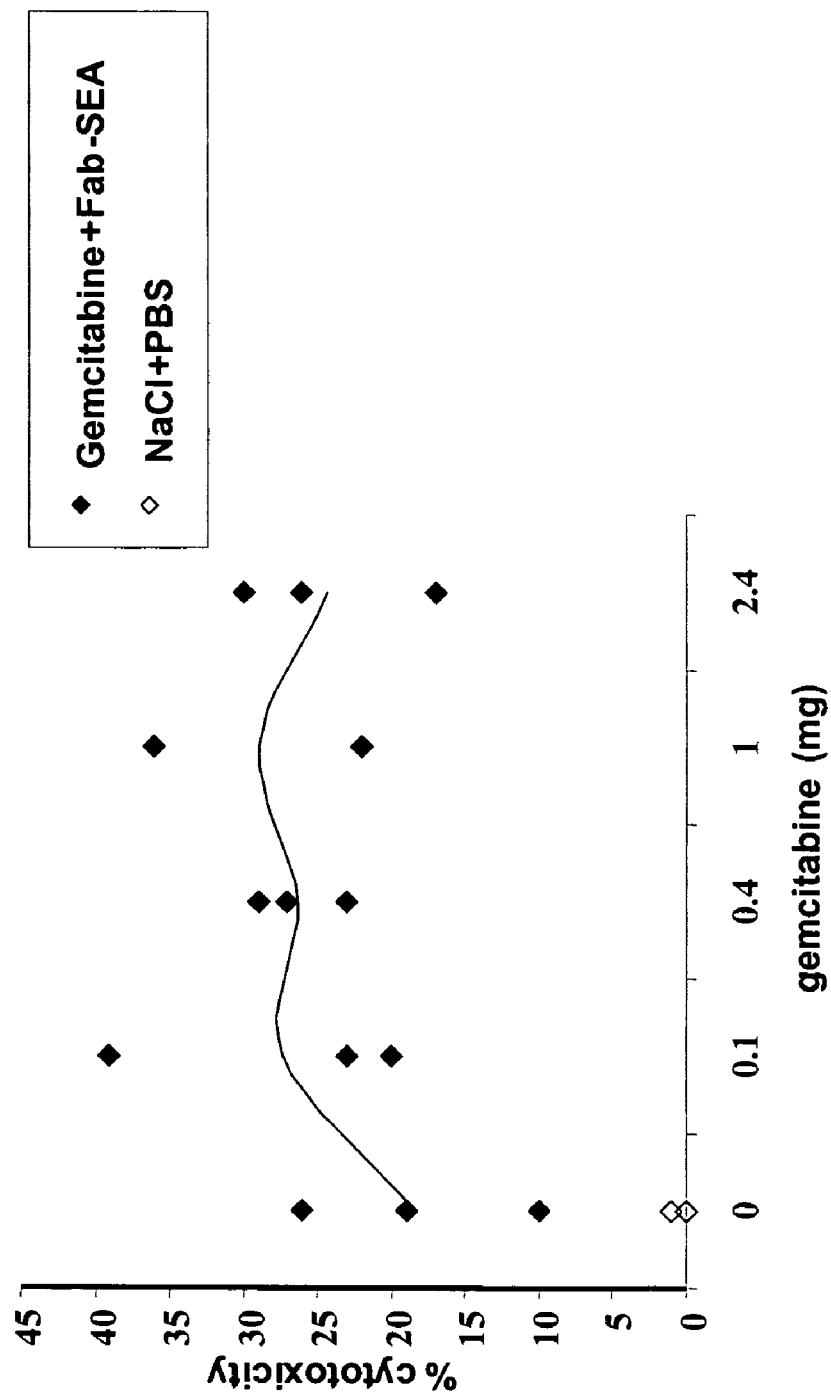
FIG. 5 shows CTL activity in bulk splenocytes from mice treated sequentially with gemcitabine at various doses and then Fab-SEA. Mice (3 mice/group) were given four injections of gemcitabine at indicated doses every third day (days 1, 4, 7 and 10) followed by treatment with three daily injections of C215Fab-SEA (10 µg/animal), starting at day 16. 48 hours after the last injection, spleens were removed and cytotoxic function (SDCC) against SEA coated A20 cells, was measured in a standard $^{51}$Cr release assay. The effector to target cell ratio was 100:1. Data points representing results from individual mice, as well as trend lines representing average values from 3 individual mice.
Figure 6:
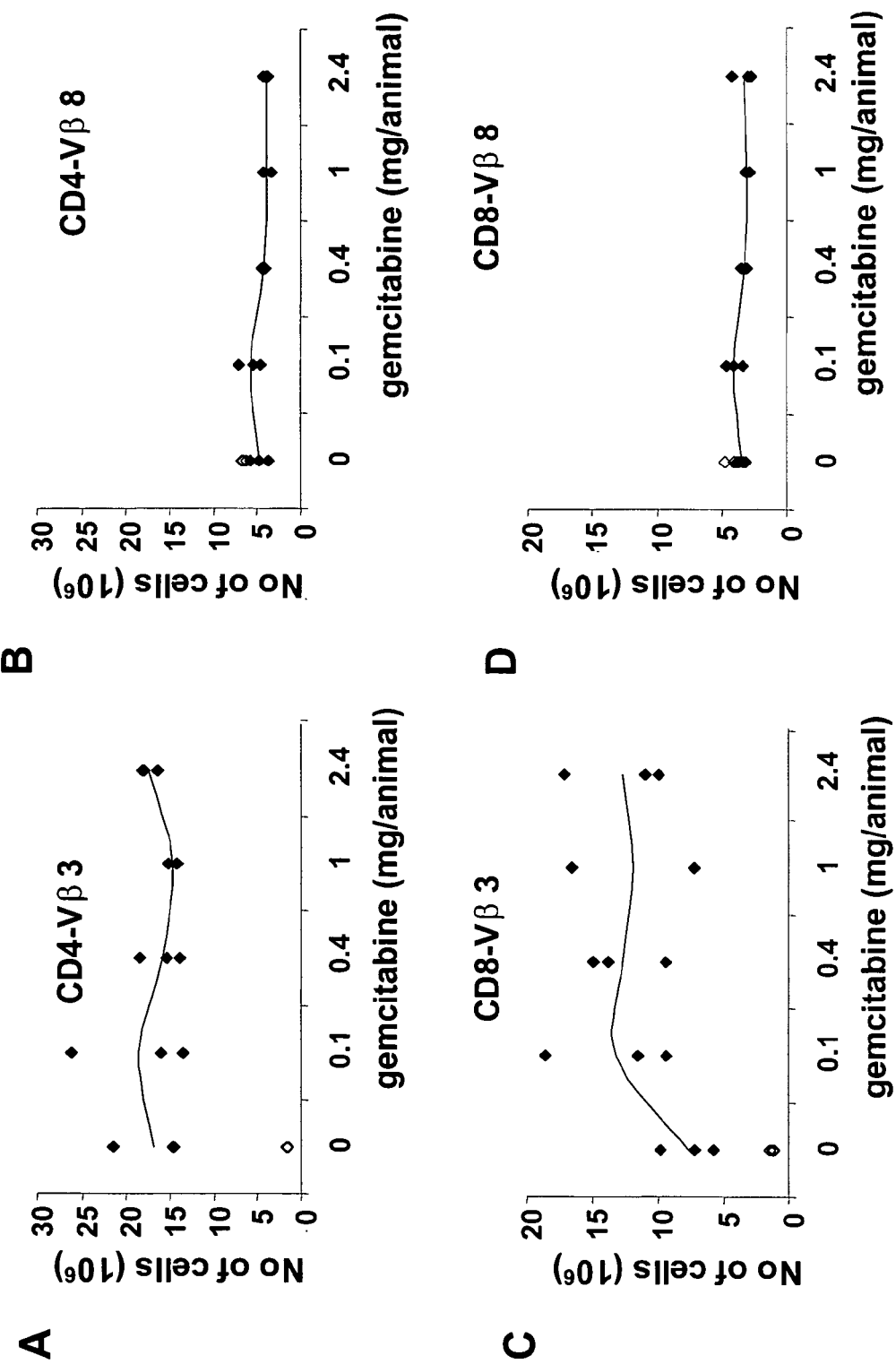
FIGS. 6A-6D show T-cell dynamics of splenocytes of mice treated sequentially with gemcitabine at various doses and then Fab-SEA. Mice (3 animals/group) were given four injections of gemcitabine at indicated doses every third day (days 1, 4, 7 and 10) followed by treatment with three daily injections of C215Fab-SEA (10 µg/animal), starting at day 16. 48 hours after the last injection, spleens were removed and $V_\beta 3$ specific expansion of $CD4^+$ and $CD8^{+c}$ells was measured. Data points representing results from individual mice, as well as trend lines representing average values from 3 individual.

Pre-Treatment with Chemotherapeutic (Gemcitabine) Does Not Negatively Interfere With SEA Induced T-Cell Activation Standard treatment of tumor free C57B1/6 mice with gemcitabine (four doses with three days interval) at various doses was followed by 3 daily injections of C215Fab-SEA starting 6 days after the last gemcitabine injection. Splenocytes were prepared 48 hours after the last injection and superantigen dependent cellular cytotoxicity (SDCC) was measured against SEA coated A20 cells in a standard $^{51}$Cr release assay. Substantial cytotoxic activity was detected in all Fab-SEA treated groups irrespective of prior gemcitabine therapy (FIG. 5). Flow cytometric analysis showed that SEA induced CD8-$V_\beta 3$ T-cell expansion increased by gemcitabine treatment (FIG. 6C). No significant T-cell activation or SDCC was found in mice treated with gemcitabine alone at any dose (FIG. 6).

Figure 7:
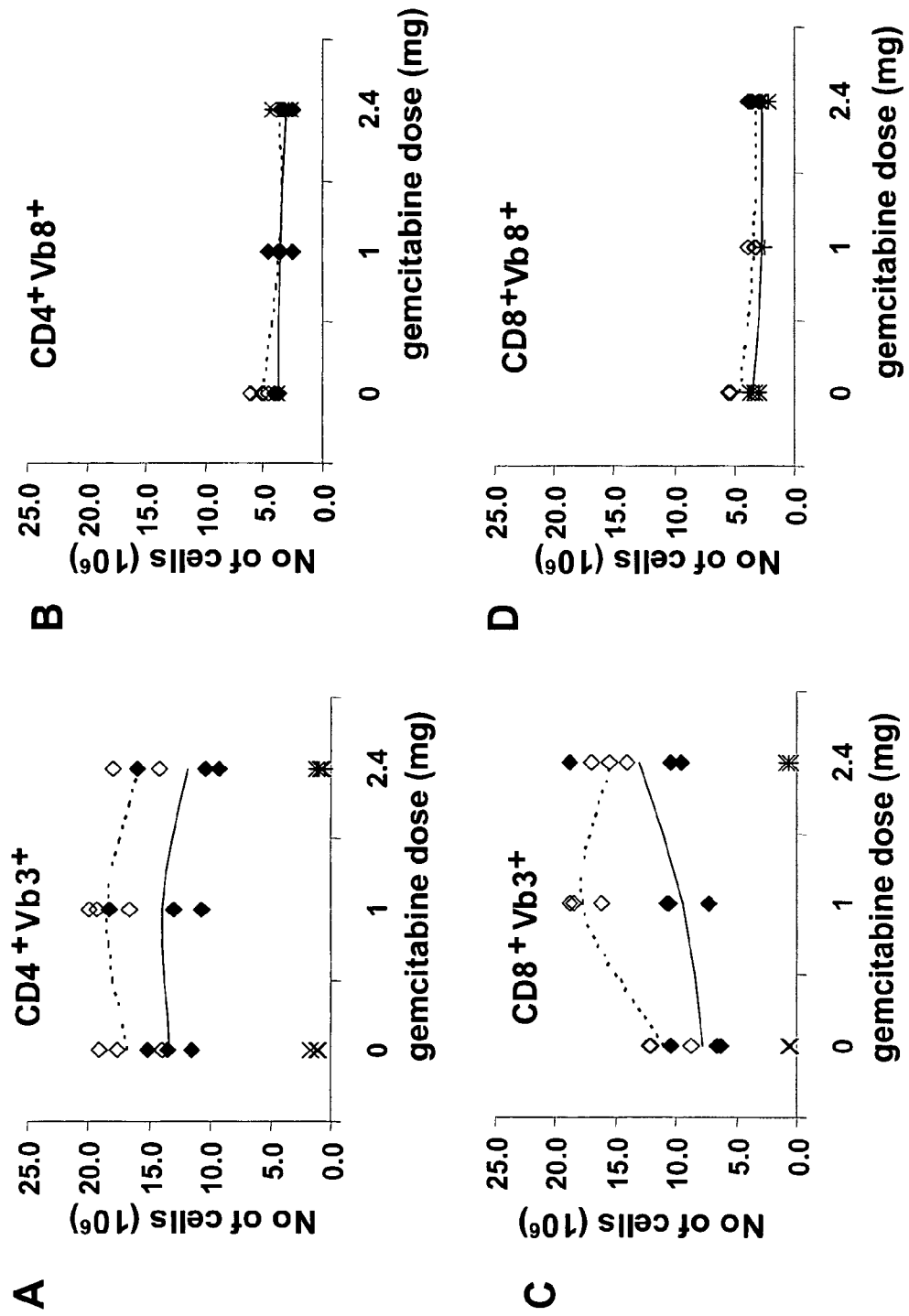
FIGS. 7A-7B show T-cell dynamics of splenocytes from mice treated sequentially with gemcitabine and then Fab-SEA. Mice (3 mice/group) were injected with gemcitabine (0, 1, 2.4 mg/mouse) every third day for four (filled diamonds) or seven doses (open diamonds), followed by treatment with three daily injections of C215Fab-SEA (10 µg/animal), starting 6 days after the last gemcitabine injection. 48 hours after the last injection, spleens were removed and $V_\beta 3$ specific expansion of CD4 and CD8 cells was measured. Data points representing results from individual mice, as well as trend lines representing average values from 3 individual mice.
FIG. 7C shows the number of CD8+ $V_\beta 3$ T cells (SEA reactive) using various concentrations and dosing schedules of gemcitabine.
FIG. 7D shows the number of CD8+ $V_\beta 8$ T cells (control) using various concentrations and dosing schedules of gemcitabine.
Figure 8:
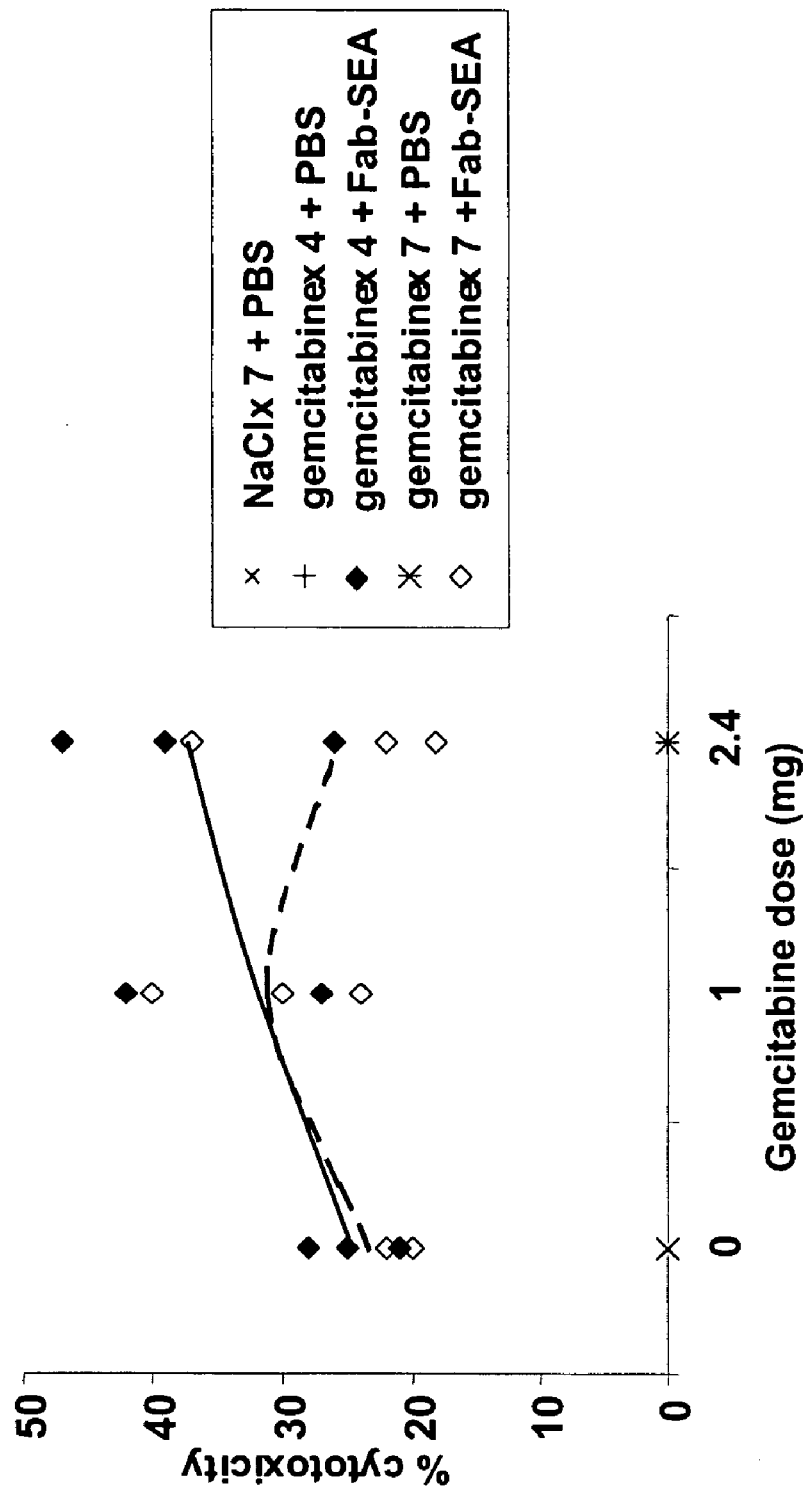
FIG. 8 shows CTL activity in bulk splenocytes from mice treated sequentially with 4 or 7 doses of gemcitabine and then Fab-SEA. Mice (3 animals/group) were injected with gemcitabine (0, 1, 2.4 mg/mouse) every third day for four (filled diamonds) or seven doses (open diamonds), followed by treatment with three daily injections of C215Fab-SEA (10 µg/animal), starting 6 days after the last gemcitabine injection. 48 hours after the last injection, spleens were removed and cytotoxic function (SDCC) against SEA coated A20 cells was measured in a standard $^{51}$Cr release assay. The effector to target cell ratio was 100:1. Data points representing results from individual mice, as well as trend lines representing average values from 3 individual mice.

To investigate the effect of prolonged gemcitabine treatment on SEA induced immune activation, mice were given 7 injections of gemcitabine with 3 days interval, followed by C215Fab-SEA treatment starting 6 days after the last gemcitabine injection. As shown in FIGS. 7 and 8, this prolonged treatment schedule did not significantly alter the responsiveness to SEA.

Figure 9:
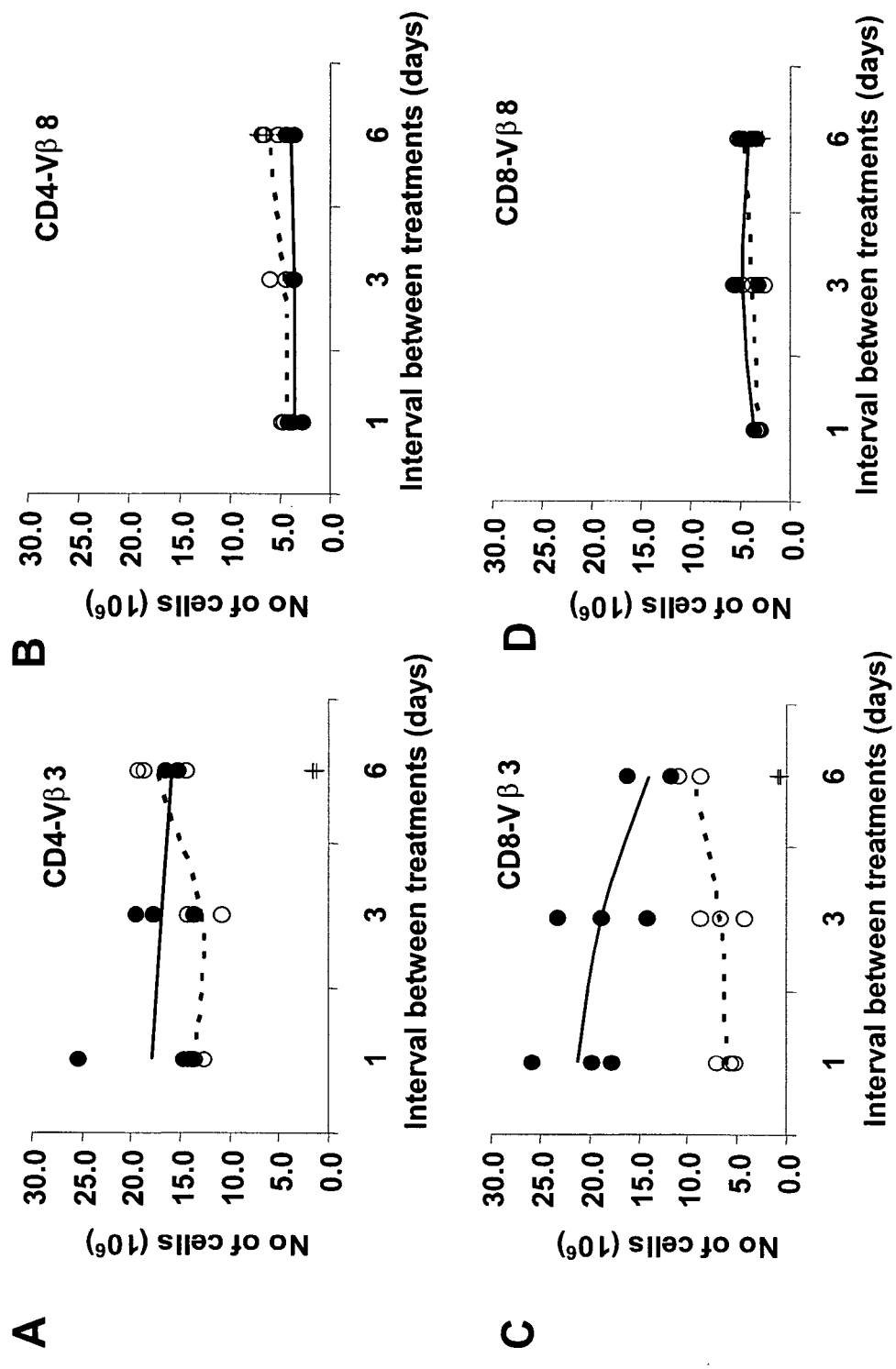
FIG. 9 shows the number of CD4+ $V_\beta 3$ T cells (SEA reactive) using various concentrations of gemcitabine.
Figure 10:
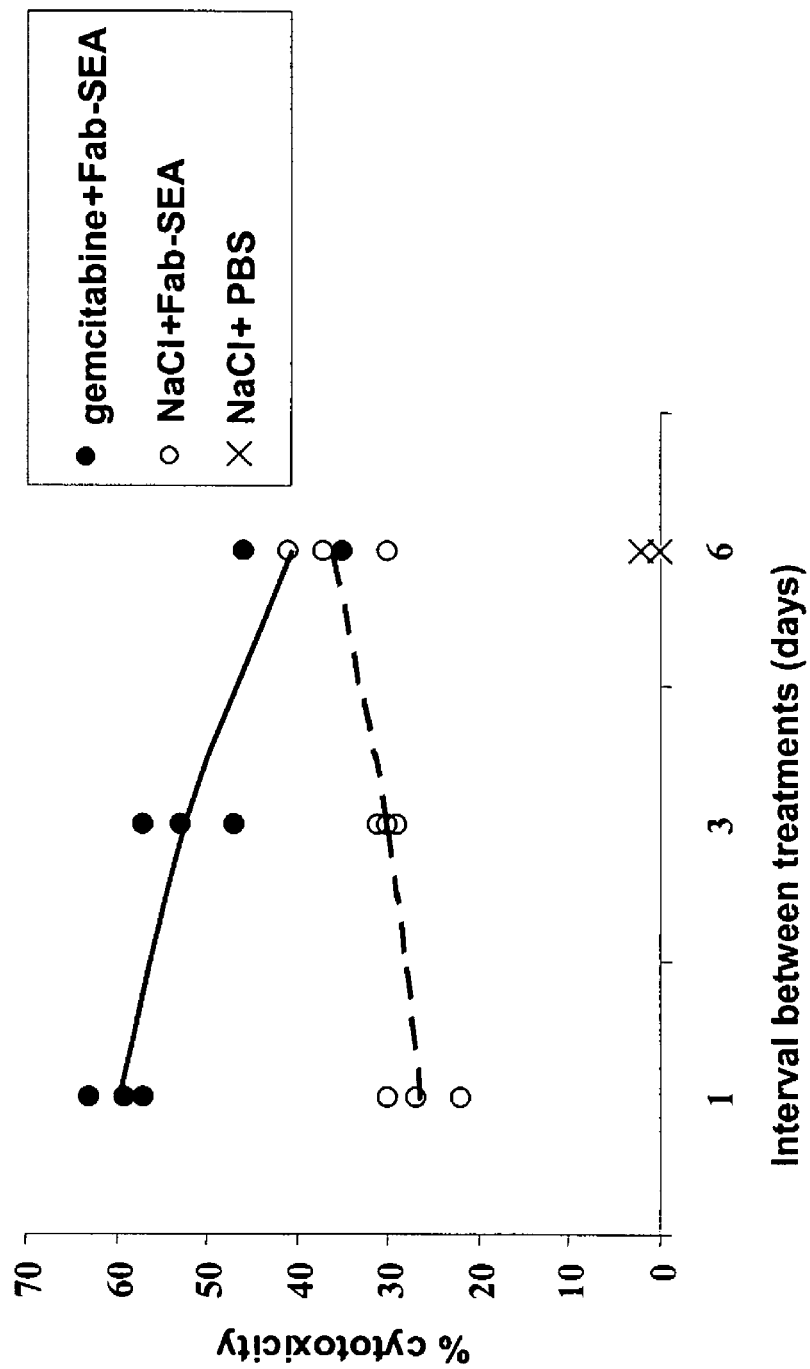
FIG. 10 shows CTL activity in bulk splenocytes from mice treated sequentially with gemcitabine and then Fab-SEA. Mice (3 mice/group) were injected with gemcitabine (2.4 mg/mouse) every third day for four doses (days 1, 4, 7 and 10), followed by treatment with three daily injections of C215Fab-SEA (10 µg/animal), starting at different time intervals after the last gemcitabine injection. 48 hours after the last injection, spleens were removed and cytotoxic function (SDCC) against SEA coated A20 cells was measured in a standard $^{51}$Cr release assay. The effector to target cell ratio was 100:1. Data points representing results from individual mice, as well as trend lines representing average values from 3 individual mice.

Next, the impact of the length of the treatment free period between gemcitabine therapy and TTS treatment on SEA induced T-cell activation was evaulated. Following standard therapy with gemcitabine at 2.4 mg/mouse, three daily injections of C215Fab-SEA were given, starting 1, 3, or 6 days after the last gemcitabine administration. Spleens were removed 48 hours post treatment and splenocytes were analysed for T-cell activation and effector functions (SDCC). Interestingly, shortening of the rest period between treatments resulted in potentiation of $V_\beta 3$ specific T-cell expansion characteristic of a SEA induced immune response (FIG. 9). This was accompanied by enhanced CTL activity of splenocytes against SEA coated A20 cells (FIG. 10).

These results indicated that pre-treatment with gemcitabine did not interfere with TTS therapy and may even act to improve SEA induced effector functions.

Example 6

TTS-Chemotherapeutic (e.g., Docetaxel) Combination Therapy: In vivo, Systemic Immune Activation in Mice The systemic immune response was evaluated in C57B1/6 mice following treatment with C215Fab-SEA in combination with the cytostatic agent docetaxel.

Animals

Female C57B1/6 mice were used. The mice were routinely used at the age of 8 to 12 weeks and received food and water ad libitum.

Cell Lines and Media

The murine B-cell lymphoma cell line A20 (ATCC, TIB-208) was maintained in RPMI 1640 with ultraglutamine supplemented with 10% FCS, 1 mM sodium pyruvate, 50 μM β-mercaptoethanol and 0.1 mg/ml gentamicin.

Treatment of Mice

C215Fab-SEA treatment was given as daily i.v. injections (10 μg/mouse, in 0.2 ml PBS containing 1% mouse serum) for 3 consecutive days. In combination studies, one i.p. injection of docetaxel was given (in 0.2 ml buffer solution containing polysorbate (0,1-10,9%), ethanol (0,1-10,1%) and NaCl (0.45-0.9%)) either before or simultaneously with C215Fab-SEA therapy. Three mice were included in each experimental group. 48 hours after the last C215Fab-SEA injection, mice were sacrificed and the spleens were removed for analysis of T-cell dynamics and cytotoxic activity.

Flow Cytometry

Single cell suspensions of splenocytes from mice injected with indicated substances were prepared. Erythrocytes were removed by hypotonic shock using Gey's solution. The remaining lymphocytes were stained for cell surface antigen expression for 30 min on ice after blocking of Fc-receptors by CD32/CD16 antibodies. Where biotinylated mAbs were used, cells were stained with streptavidin-tricolor. Cells were washed twice in PBS+1% BSA after each staining step. The samples were analysed in a FACSort flow cytometer.

Cytotoxicity Assays

Mice treated with indicated substances were sacrificed 48 h after the last injection and the spleens were removed. Cytotoxicity of bulk splenocytes was measured against SEA coated (1 μg/ml) A20 cells using a standard $^{51}$Cr release assay (Dohlsten et al., 1990; Hedlund et al, 1993). The effector to target cell ratio was 100:1. Calculations were carried out according to the formula:

$$\% \text{ specific lysis} = \frac{\text{experimental release} - \text{spontaneous release}}{\text{total release} - \text{spontaneous release}} \times 100$$

Results

Figure 11:
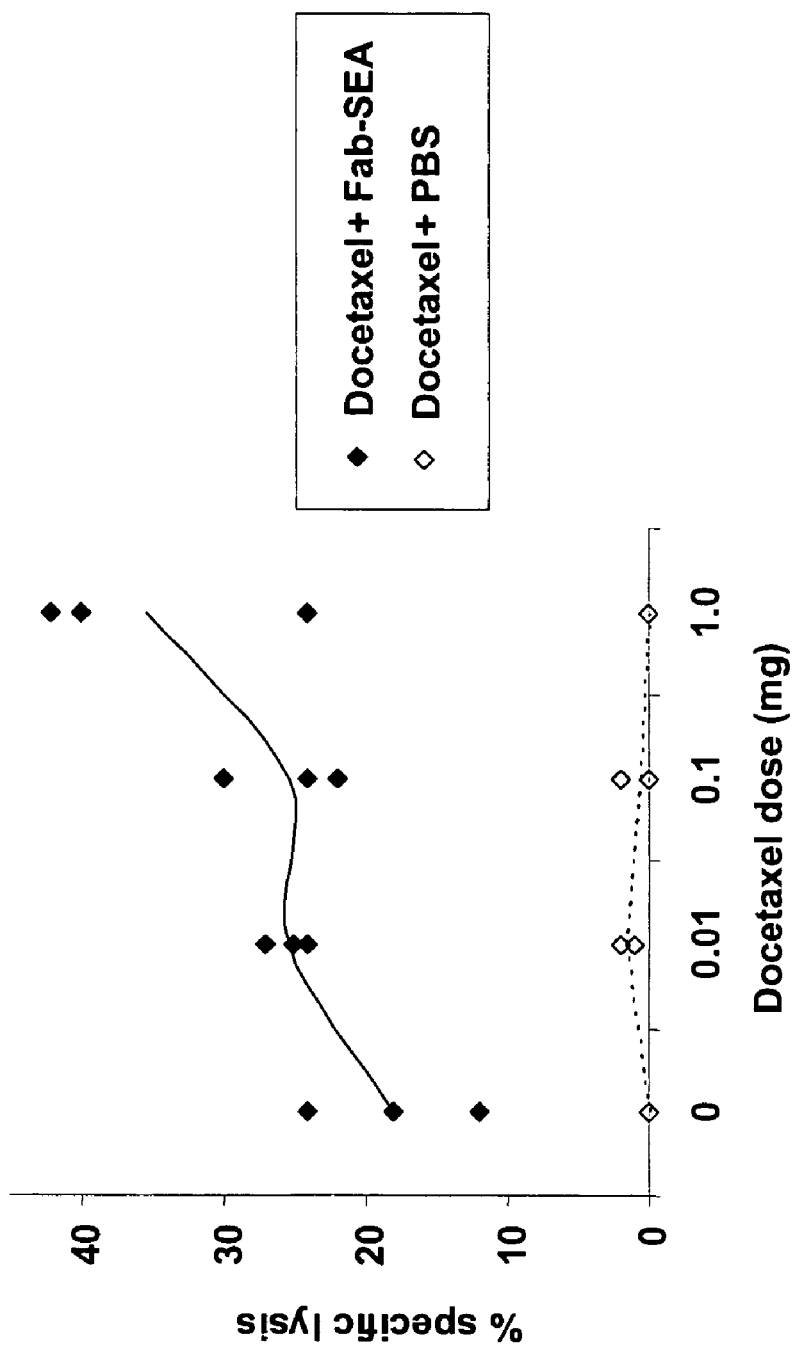
FIG. 11 shows CTL activity in bulk splenocytes from mice treated sequentially with docetaxel at various doses and then Fab-SEA. Mice (3 animals/group) were given one i.p. injection of docetaxel at indicated doses followed by treatment with three daily injections of C215Fab-SEA (10 µg/animal), starting 1 day after cytostatic treatment. 48 hours after the last Fab-SEA injection, spleens were removed and cytotoxic function (SDCC) against SEA coated A20 cells was measured in a standard $^{51}$Cr release assay. The effector to target ratio was 100:1. Data points representing results from individual mice, as well as trend lines representing average values from 3 individual mice.
Figure 12:
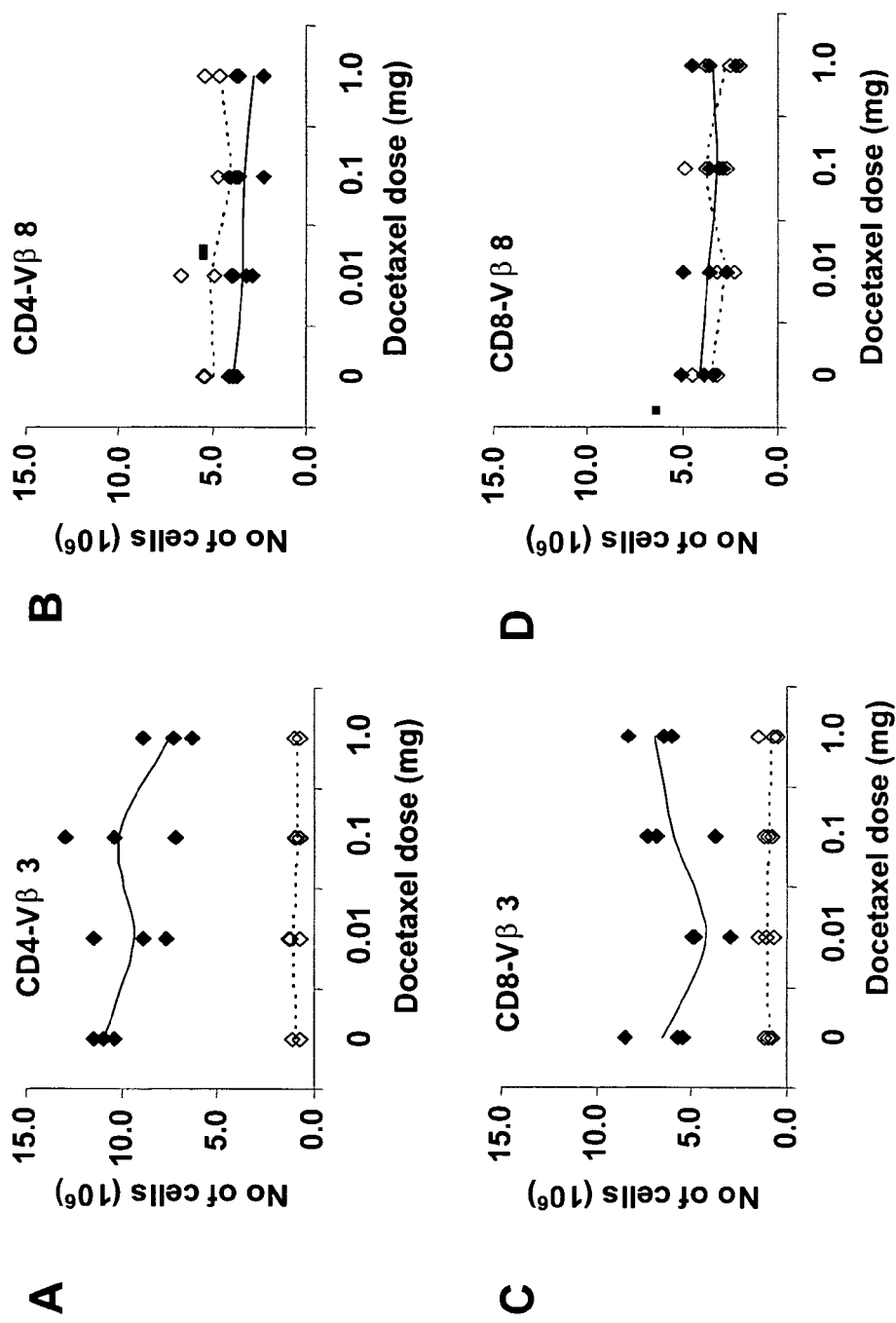
FIGS. 12A-12D show T-cell dynamics of splenocytes of mice treated sequentially with docetaxel at various doses and then Fab-SEA. Mice (3 animals/group) were given one i.p. injection of docetaxel at indicated doses followed by treatment with three daily injections of C215Fab-SEA (10 µg/animal), starting 1 day after cytostatic treatment. 48 hours after the last Fab-SEA injection, spleens were removed and $V_\beta 3$ specific expansion of CD4 and CD8 cells was measured. Data points representing results from individual mice, as well as trend lines representing average values from 3 individual mice.

Pre-Treatment With Chemotherapeutic (Docetaxel) Does Not Negatively Interfere With SEA-Induced T-Cell Activation Treatment of C57B1/6 mice with various doses of docetaxel on day 1 was followed by 3 daily injections of C215Fab-SEA starting at day 2. Splenocytes were prepared 48 hours after the last injection and superantigen dependent cellular cytotoxicity (SDCC) was measured against SEA coated A20 cells in a standard $^{51}$Cr release assay. Substantial cytotoxic activity (FIG. 11) and $V_\beta 3$ specific T-cell expansion (FIG. 12) were detected in all Fab-SEA treated groups irrespective of prior docetaxel therapy. Thus, cytostatic treatment before TTS therapy apparently did not interfere with SEA mediated immune activation. Rather, administration of therapeutic doses of docetaxel (1 mg/animal) shortly before TTS treatment resulted in potentiation of SEA induced T-cell activation as measured by SDCC (FIG. 11). No significant T-cell activation or SDCC was recorded in mice treated with docetaxel alone at any dose. The highest docetaxel dose used in this experiment (1 mg) was sufficient to induce significant anti-tumor effects in tumor bearing animals when administered alone and to augment of TTS therapy the effect when combined with C215Fab-SEA.

Example 7

TTS-Chemotherapeutic (e.g., Gemcitabine) Combination Therapy: In vivo-Synergistic Effects In Mice C215Fab-SEA (ABR-214720) in combination with gemcitabine was investigated with regard to tumor therapy efficacy in C57B1/6 mice. Mice were inoculated i.v. with B16C215 melanoma cells to induce lung tumors in the therapy studies. Gemcitabine was administered after the first C215Fab-SEA therapy cycle.

Cells

The murine B16 melanoma cell line (obtained from ATCC) transfected with the human antigen C215 was cultured in cell growth medium. The cell line was prepared by detachment of cells grown in vitro with cell dissociation solution, resuspended in PBS, counted and diluted in PBS with 1% C57B1/6 mouse serum.

Animals

Female C57B1/6 mice were used. The mice were routinely used at the age of 8 to 12 weeks and received food and water ad libitum.

Tumor Therapy In C57B1/6 Mice: Number of Lung Tumors

Groups of eight C57B1/6 mice were inoculated i.v. with $1.75 \times 10^5$ B16 melanoma cells transfected with the C215 human tumor antigen (Dohlsten, M. et al., 1994) into the tail vein, in 0.2 ml vehicle, to induce lung tumors. The chemotherapeutic agent was injected i.p. on various days in 0.2 ml vehicle. For each treatment cycle ABR-214720 was injected i.v. with four daily injections in 0.2 ml vehicle. Three to 6 weeks later the mice were sacrificed and the lungs were removed. After fixation in Bouins solution for at least 24 h, the numbers of lung tumors were counted.

Treatment Regimens

Ten μg/mouse of ABR-214720 was given days 3-6 and 18-21 and 2.4 mg/mouse of gemcitabine was given days 2, 5, 8 and 11 (only mono-therapy) or days 8, 11, 14 and 17 as mono-therapies or in combination, respectively.

Results

As shown in Table 6, administration of 2.4 mg gemcitabine per animal on days 2, 5, 8 and 11 was active as a single agent in this model, demonstrating the in vivo sensitivity of B16 tumor cells to gemcitabine.

TABLE 6

Therapy of tumor metastases: Number of lung tumors per animal after treatment with gemcitabine.

| Treatment | Mean number of lung metastases day 21 |
|---|---|
| Control* | 147 |
| Gemcitabine 2.4 mg/mouse | 49.5 |

*non-treated tumor inoculated animals

As illustrated in Table 7, combination therapy was superior and synergistic as compared to treatment with single treatment gemcitabine or TTS, in reducing the number of lung metastases. Single treatment TTS resulted in significant anti-tumor effect. Gemcitabine was administered from day 8 after tumor inoculation at a dosage shown to be tumor growth inhibitory in mice with less pronounced disease, but did not exert any anti-tumor effect per se on this rapidly growing tumor at this stage. TTS and gemcitabine doses were selected to exert maximal anti-tumor effects.

TABLE 7

Therapy of tumor metastases: Number of lung tumors per animal after treatment with the drugs alone or in combination

| Treatment | Mean number of lung metastases Day 28 | Mean number of lung metastases Day 40 |
|---|---|---|
| Control* | 117 | All animals dead |
| TTS | 23 | 21 |
| Gemcitabine | 141 | All animals dead |
| TTS + gemcitabine | 11 | 10 |

*non-treated tumor inoculated animals

Thus, the combination of TTS with chemotherapeutic agents for example gemcitabine resulted in synergistic anti-tumor effects when used in sequence and starting with TTS.

Example 8

TTS-Chemotherapeutic (e.g., Docetaxel) Combination Therapy: In vivo-Synergistic Effects In Mice C215Fab-SEA (ABR-214720) in combination with docetaxel was investigated with regard to tumor therapy efficacy in C57B1/6 mice. Mice were inoculated i.v. with B16C215 melanoma cells to induce lung tumors in the therapy studies. Docetaxel was administered before and after as well as during the C215Fab-SEA therapy cycle.

Cells

The murine B16 melanoma cell line (obtained from ATCC) transfected with the human antigen C215 was cultured in cell growth medium. The cell line was prepared by detachment of cells grown in vitro with cell dissociation solution, resuspended in PBS, counted and diluted in PBS with 1% C57B1/6 mouse serum.

Animals

Female C57B1/6 mice were used. The mice were routinely used at the age of 8 to 12 weeks and received food and water ad libitum.

Tumor Therapy In C57B1/6 Mice: Number of Lung Tumors

Groups of eight C57B1/6 mice were inoculated i.v. with $1.75 \times 10^5$ B16 melanoma cells transfected with the C215 human tumor antigen (Dohlsten, M. et al., 1994) into the tail vein, in 0.2 ml vehicle, to induce lung tumors. The chemotherapeutic agent was injected i.p. on various days in 0.2 ml vehicle. For each treatment cycle ABR-214720 was injected i.v. with four daily injections in 0.2 ml vehicle. Three to 6 weeks later the mice were sacrificed and the lungs were removed. After fixation in Bouins solution for at least 24 h, the numbers of lung tumors were counted.

Treatment Regimens

Ten μg/mouse of ABR-214720 was given days 3-6 and 1.0 mg/mouse of docetaxel was given days 2 and 9 or day 5 as mono-therapies or in combination, respectively.

Results

As can be seen from Table 8, the combination therapy was superior and synergistic as compared to treatment with docetaxel (days 2 and 9) or TTS only, in reducing the number of lung metastases. Treatment with TTS or docetaxel alone resulted in significant anti-tumor effects. However, treatment with TTS in combination with docetaxel exerted maximal anti-tumor effects.

TABLE 8

Therapy of tumor metastases: Number of lung tumors per animal after treatment with the drugs alone or in combination.

| Treatment | Mean number of lung metastases day 21 |
|---|---|
| Control* | 137 |
| TTS | 19 |
| Docetaxel | 48 |
| TTS + Docetaxel | 1 |

*non-treated tumor inoculated animals

As can be seen from Table 9, the combination therapy was superior and synergistic as compared to treatment with docetaxel (day 5) or TTS only, in reducing the number of lung metastases. Treatment with TTS alone resulted in significant anti-tumor effects. However, treatment with TTS in combination with docetaxel exerted maximal anti-tumor effects.

TABLE 9

Therapy of tumor metastases: Number of lung tumors per animal after treatment with the drugs alone or in combination.

| Treatment | Mean number of lung metastases day 21 |
|---|---|
| Control* | 73 |
| TTS | 14 |
| Docetaxel | 93 |
| TTS + Docetaxel | 6 |

*non-treated tumor inoculated animals

Thus, the combination of TTS with chemotherapeutic agents for example docetaxel resulted in synergistic anti-tumor effects when used in sequence with TTS as well as integrated on the third day of the TTS cycle.

Example 9

TTS-Chemotherapeutic (e.g., Docetaxel) Combination Therapy: In vivo-Synergistic Effects In Mice C215Fab-SEA (ABR-214720) in combination with docetaxel was investigated with regard to tumor therapy efficacy in C57B1/6 mice as measured by survival. Mice were inoculated i.v. with B16C215 melanoma cells to induce lung tumors in the therapy studies. Docetaxel was administered before or before and after the C215Fab-SEA therapy cycle.

Cells

The murine B16 melanoma cell line (obtained from ATCC) transfected with the human antigen C215 was cultured in cell growth medium. The cell line was prepared by detachment of cells grown in vitro with cell dissociation solution, resuspended in PBS, counted and diluted in PBS with 1% C57B1/6 mouse serum.

Animals

Female C57B1/6 mice were used. The mice were routinely used at the age of 8 to 12 weeks and received food and water ad libitum.

Tumor Therapy In C57B1/6 Mice: Survival

Groups of 8 to 20 C57B1/6 mice were inoculated i.v. with $1.75 \times 10^5$ B16 melanoma cells transfected with the C215 human tumor antigen (Dohlsten, M., et al. 1994) into the tail vein, in 0.2 ml vehicle, to induce lung tumors. The chemotherapeutic agent was injected i.p. on various days in 0.2 ml vehicle. For each treatment cycle ABR-214720 was injected i.v. with four daily injections in 0.2 ml vehicle. When the mice showed signs of morbidity or on day 90 or 120, they were sacrificed and an autopsy was carried out.

Treatment Regimens

Ten μg/mouse of ABR-214720 was given days 3-6 and 1.0 mg/mouse of docetaxel was given day 2 or days 2 and 9 as mono-therapies or in combination, respectively.

Results

As illustrated in Table 10, combination therapy was superior and synergistic as compared to treatment with single treatment docetaxel or TTS, in increasing longevity. Single treatment TTS or docetaxel resulted in significant anti-tumor effects. TTS and docetaxel doses were selected to exert maximal anti-tumor effects.

TABLE 10

Therapy of tumor metastases: Median survival time of mice with lung tumor metastasis after treatment with the drugs alone or in combination.

| Treatment | Median survival time (Days) |
|---|---|
| Control* | 33 |
| TTS | 41.5 |
| Docetaxel (Day 2) | 38 |
| Docetaxel (Days 2 and 9) | 37.5 |
| TTS + Docetaxel (Day 2) | 66 |
| TTS + Docetaxel (Days 2 and 9) | >90 |

*non-treated tumor inoculated animals

Thus, the combination of TTS with chemotherapeutic agents for example docetaxel resulted in synergistic anti-tumor effects when used in sequence and starting with the chemotherapeutic agent.

Example 10

TTS-Chemotherapeutic (e.g., Docetaxel) Combination Therapy: In vivo-Synergistic Effects In Mice C215Fab-SEA (ABR-214720) in combination with docetaxel was investigated with regard to tumor therapy efficacy in C57B1/6 mice as measured by survival. Mice were inoculated i.v. with B16C215 melanoma cells to induce lung tumors in the therapy studies. Docetaxel was administered after the C215Fab-SEA therapy cycles.

Cells

The murine B16 melanoma cell line (obtained from ATCC) transfected with the human antigen C215 was cultured in cell growth medium. The cell line was prepared by detachment of cells grown in vitro with cell dissociation solution, resuspended in PBS, counted and diluted in PBS with 1% C57B1/6 mouse serum.

Animals

Female C57B1/6 mice were used. The mice were routinely used at the age of 8 to 12 weeks and received food and water ad libitum.

Tumor Therapy In C57B1/6 Mice: Survival

Groups of 8 to 20 C57B1/6 mice were inoculated i.v. with $1.75 \times 10^5$ B16 melanoma cells transfected with the C215 human tumor antigen (Dohlsten, M., et al. 1994) into the tail vein, in 0.2 ml vehicle, to induce lung tumors. The chemotherapeutic agent was injected i.p. on various days in 0.2 ml vehicle. For each treatment cycle ABR-214720 was injected i.v. with four daily injections in 0.2 ml vehicle. When the mice showed signs of morbidity or on day 90 or 120, they were sacrificed and an autopsy was carried out.

Treatment Regimens

Ten µg/mouse of ABR-214720 was given days 3-6 and 31-34 and 2.0 mg/mouse of docetaxel was given days 8, 22, 36 and 50 as mono-therapies or in combination, respectively.

Results

As illustrated in Table 11, combination therapy was superior and synergistic as compared to treatment with single treatment docetaxel or TTS, in increasing longevity. Single treatment TTS or docetaxel resulted in significant anti-tumor effects. TTS and docetaxel doses were selected to exert maximal anti-tumor effects.

TABLE 11

Therapy of tumor metastases: Median survival time of mice with lung tumor metastasis after treatment with the drugs alone or in combination.

| Treatment | Median survival time (Days) |
| --- | --- |
| Control* | 31.5 |
| TTS | 48 |
| Docetaxel | 50 |
| TTS + Docetaxel | 75 |

*non-treated tumor inoculated animals

Thus, the combination of TTS with chemotherapeutic agents for example docetaxel resulted in synergistic anti-tumor effects when used in sequence and starting with TTS.

Example 11

TTS-Chemotherapeutic (e.g., Docetaxel) Combination Therapy: In vivo-Synergistic Effects In Mice C215Fab-SEA (ABR-214720) in combination with docetaxel was investigated with regard to tumor therapy efficacy in C57B1/6 mice as measured by survival. Mice were inoculated i.v. with B16C215 melanoma cells to induce lung tumors in the therapy studies. Docetaxel was administered the day immediately after the last day of the C215Fab-SEA therapy cycles.

Cells

The murine B16 melanoma cell line (obtained from ATCC) transfected with the human antigen C215 was cultured in cell growth medium. The cell line was prepared by detachment of cells grown in vitro with cell dissociation solution, resuspended in PBS, counted and diluted in PBS with 1% C57B1/6 mouse serum.

Animals

Female C57B1/6 mice were used. The mice were routinely used at the age of 8 to 12 weeks and received food and water ad libitum.

Tumor Therapy In C57B1/6 Mice: Survival

Groups of 8 to 20 C57B1/6 mice were inoculated i.v. with $1.75 \times 10^5$ B16 melanoma cells transfected with the C215 human tumor antigen (Dohlsten, M., et al. 1994) into the tail vein, in 0.2 ml vehicle, to induce lung tumors. The chemotherapeutic agent was injected i.p. on various days in 0.2 ml vehicle. For each treatment cycle ABR-214720 was injected i.v. with four daily injections in 0.2 ml vehicle. When the mice showed signs of morbidity or on day 90 or 120, they were sacrificed and an autopsy was carried out.

Treatment Regimens

Ten µg/mouse of ABR-214720 was given days 3-6, 17-20, 45-48 and 59-62 and 2.0 mg/mouse of docetaxel was given days 7, 21, 35, 49, 63 and 77 as mono-therapies or in combination, respectively.

Results

As illustrated in Table 12, combination therapy was superior and synergistic as compared to treatment with single treatment docetaxel or TTS, in increasing longevity. Single treatment TTS or docetaxel resulted in significant anti-tumor effects. TTS and docetaxel doses were selected to exert maximal anti-tumor effects.

TABLE 12

Therapy of tumor metastases: Median survival time of mice with lung tumor metastasis after treatment with the drugs alone or in combination.

| Treatment | Median survival time (Days) |
| --- | --- |
| Control* | 35 |
| TTS | 75 |
| Docetaxel | 61 |
| TTS + Docetaxel | >120 |

*non-treated tumor inoculated animals

Thus, the combination of TTS with chemotherapeutic agents for example docetaxel resulted in synergistic anti-tumor effects when used in sequence and starting with TTS and giving the chemotherapeutic agent the day immediately after the last day of the TTS treatment cycles.

Example 12

TTS-Chemotherapeutic (e.g., Gemcitabine) Combination Therapy: In vivo-Humanized SCID Mice Model The effect of TTS treatment (5T4Fab-SEA/E-120, ABR-217620) in combination with the chemotherapeutic agent gemcitabine on tumor growth was assessed in an experimental human tumor model. Severe Combined Immunodeficient (SCID) mice were transplanted with human lymphocytes and human tumor cells growing intraperitoneally as solid tumors. ABR-217620 is a TTS developed for human use and therefore tested in the humanized SCID model. The anti-tumor TTS effects are dependent of activated human lymphocytes.

Cells

The human tumor cell line Colo 205 (obtained from ATCC) was cultured in cell growth medium. The cell line was prepared by detachment of cells grown in vitro with cell dissociation solution, resuspended in PBS, counted and diluted in PBS with 1% SCID mouse serum. Peripheral blood mononuclear cells (PBMC) were obtained from blood donors at the University Hospital of Lund. The PBMC were isolated by density centrifugation on Ficoll-Paque. The cells were then cultured in R10 medium and stimulated with TTS to obtain activated effector T lymphocytes. The T lymphocytes were prepared by detachment of cells grown in vitro, resuspended in PBS, counted and diluted in PBS with 1% SCID mouse serum.

Animals

Female SCID mice were used. The mice were routinely used at the age of 8 to 12 weeks and received sterile pelleted rodent diet and sterile water ad libitum.

Tumor Therapy In SCID Mice: Intraperitoneal Tumor Mass

Seven to 8 SCID mice per treatment group were injected intraperitoneally with human tumor cells in 0.2 ml vehicle. The mice received an intraperitoneal injection with activated lymphocytes in 0.2 ml vehicle, and additionally they received 4-5 daily intravenous injections with TTS test substance in 0.2 ml vehicle, the first injection at the same time as the activated lymphocytes were given. The TTS treatment was combined with intraperitoneal (i.p.) or intravenous (i.v.) injections of the chemotherapeutic agent. After 3-10 weeks the mice were sacrificed by neck dislocation and the tumor mass was determined.

Treatment Regimens

Fifty μg/mouse of ABR-217620 was given days 2-6 after tumor injection and 2.0 mg/mouse of docetaxel was given i.v. days 3, 5 and 8 as mono-therapies or in combination, respectively.

Results

As can be seen from Table 13, the combination therapy was superior and synergistic as compared to treatment with gemcitabine or TTS only, in reducing the tumor mass. Treatment with TTS alone resulted in significant anti-tumor effects. However, treatment with TTS in combination with gemcitabine exerted maximal anti-tumor effects.

TABLE 13

Therapy of human tumors: Tumor mass per animal after treatment with the drugs alone or in combination.

| Treatment | Mean/Median Tumor Mass (mg) |
| --- | --- |
| Control* | 403/362 |
| TTS | 133/79 |
| Gemcitabine | 303/300 |
| TTS + Gemcitabine | 60/43 |

*non-treated tumor inoculated animals

Thus, the combination of TTS with chemotherapeutic agents for example gemcitabine resulted in synergistic anti-tumor effects when used integrated, starting closely before the TTS cycle.

Example 13

TTS-Chemotherapeutic (e.g., Docetaxel) Combination Therapy: In vivo-Humanized SCID Mice Model The effect of TTS treatment (5T4Fab-SEA/E-120, ABR-217620) in combination with the chemotherapeutic agent docetaxel on tumor growth was assessed in an experimental human tumor model. Severe Combined Immunodeficient (SCID) mice were transplanted with human lymphocytes and human tumor cells growing intraperitoneally as solid tumors. ABR-217620 is a TTS developed for human use and therefore tested in the humanized SCID model. The anti-tumor TTS effects are dependent of activated human lymphocytes.

Cells

The human tumor cell line Colo 205 (obtained from ATCC) was cultured in cell growth medium. The cell line was prepared by detachment of cells grown in vitro with cell dissociation solution, resuspended in PBS, counted and diluted in PBS with 1% SCID mouse serum. Peripheral blood mononuclear cells (PBMC) were obtained from blood donors at the University Hospital of Lund. The PBMC were isolated by density centrifugation on Ficoll-Paque. The cells were then cultured in R10 medium and stimulated with TTS to obtain activated effector T lymphocytes. The T lymphocytes were prepared by detachment of cells grown in vitro, resuspended in PBS, counted and diluted in PBS with 1% SCID mouse serum.

Animals

Female SCID mice were used. The mice were routinely used at the age of 8 to 12 weeks and received sterile pelleted rodent diet and sterile water ad libitum.

Tumor Therapy In SCID Mice: Intraperitoneal Tumor Mass

Seven to 8 SCID mice per treatment group were injected intraperitoneally with human tumor cells in 0.2 ml vehicle. The mice received an intraperitoneal injection with activated lymphocytes in 0.2 ml vehicle, and additionally they received 4-5 daily intravenous injections with TTS test substance in 0.2 ml vehicle, the first injection at the same time as the activated lymphocytes were given. The TTS treatment was combined with intraperitoneal (i.p.) or intravenous (i.v.) injections of the chemotherapeutic agent. After 3-10 weeks the mice were sacrifised by neck dislocation and the tumor mass was determined.

Treatment Regimens

Fifty μg/mouse of ABR-217620 was given days 6-10 after tumor injection and 0.2 mg/mouse of docetaxel was given i.p. day 4 as mono-therapies or in combination, respectively.

Results

As can be seen from Table 14, the combination therapy was superior and synergistic as compared to treatment with docetaxel or TTS only, in reducing the tumor mass. Treatment with docetaxel alone resulted in significant anti-tumor effects. However, treatment with TTS in combination with gemcitabine exerted maximal anti-tumor effects.

TABLE 14

Therapy of human tumors: Tumor mass per animal after treatment with the drugs alone or in combination.

| Treatment | Mean/Median Tumor Mass (mg) |
| --- | --- |
| Control* | 321/282 |
| TTS | 315/316 |
| Docetaxel | 176/103 |
| TTS + Docetaxel | 52/46 |

*non-treated tumor inoculated animals

Thus, the combination of TTS with chemotherapeutic agents for example docetaxel resulted in synergistic anti-tumor effects when the chemotherapeutic agent is used closely before the TTS cycle.

Example 14

TTS-Chemotherapeutic (e.g., Docetaxel) Combination Therapy: In vivo-Humanized SCID Mice Model The effect of TTS treatment (5T4Fab-SEA/E-120, ABR-217620) in combination with the chemotherapeutic agent docetaxel on tumor growth was assessed in an experimental human tumor model. Severe Combined Immunodeficient (SCID) mice were transplanted with human lymphocytes and human tumor cells growing intraperitoneally as solid tumors. ABR-217620 is a TTS developed for human use and therefore tested in the humanized SCID model. The anti-tumor TTS effects are dependent of activated human lymphocytes.

Cells

The human tumor cell line Calu-1 (obtained from ATCC) was cultured in cell growth medium. The cell line was prepared by detachment of cells grown in vitro with cell dissociation solution, resuspended in PBS, counted and diluted in PBS with 1% SCID mouse serum. Peripheral blood mononuclear cells (PBMC) were obtained from blood donors at the University Hospital of Lund. The PBMC were isolated by density centrifugation on Ficoll-Paque. The cells were then cultured in R10 medium and stimulated with TTS to obtain activated effector T lymphocytes. The T lymphocytes were prepared by detachment of cells grown in vitro, resuspended in PBS, counted and diluted in PBS with 1% SCID mouse serum.

Animals

Female SCID mice were used. The mice were routinely used at the age of 8 to 12 weeks and received sterile pelleted rodent diet and sterile water ad libitum.

Tumor Therapy In SCID Mice: Intraperitoneal Tumor Mass

Seven to 8 SCID mice per treatment group were injected intraperitoneally with human tumor cells in 0.2 ml vehicle. The mice received an intraperitoneal injection with activated lymphocytes in 0.2 ml vehicle, and additionally they received 4-5 daily intravenous injections with TTS test substance in 0.2 ml vehicle, the first injection at the same time as the activated lymphocytes were given. The TTS treatment was combined with intraperitoneal (i.p.) or intravenous (i.v.) injections of the chemotherapeutic agent. After 3-10 weeks the mice were sacrificed by neck dislocation and the tumor mass was determined.

Treatment Regimens

Fifty μg/mouse of ABR-217620 was given days 2-6 after tumor injection and 0.2 mg/mouse of docetaxel was given i.p. day 7 as mono-therapies or in combination, respectively.

Results and Discussion

As can be seen from Table 15, the combination therapy was superior and synergistic as compared to treatment with docetaxel or TTS only, in reducing the tumor mass. Treatment with docetaxel alone resulted in significant anti-tumor effects. However, treatment with TTS in combination with gemcitabine exerted maximal anti-tumor effects.

TABLE 15

Therapy of human tumors: Tumor mass per animal after treatment with the drugs alone or in combination.

| Treatment | Mean/Median Tumor Mass (mg) |
|---|---|
| Control* | 156/39 |
| TTS | 221/79 |
| Docetaxel | 31/29 |
| TTS + Docetaxel | 9/5 |

*non-treated tumor inoculated animals

Thus, the combination of TTS with chemotherapeutic agents for example docetaxel resulted in synergistic anti-tumor effects when the chemotherapeutic agent is used closely after the TTS cycle.

Example 15

TTS-Chemotherapeutic Combination Therapy: In vivo-Inhibition of Anti-TTS Antibody Formation It is of vital importance that high titer antibodies do not develop and neutralize the TTS drug. C215Fab-SEA (ABR-214720) in combination with gemcitabine was investigated with regard to modulation of the anti-SEA antibody response in C57Bl/6 mice. Primary anti-SEA antibody response was induced by immunization with SEA. ABR-214720 treatment was given as 4 daily i.v. injections. For combination studies, gemcitabine was injected four times at three days intervals starting either before completing TTS therapy or shortly after the last ABR-214720 injection.

Animals

Female C57Bl/6 mice were used. The mice were routinely used at the age of 8 to 12 weeks and received food and water ad libitum.

Determination of Mouse Anti-SEA Antibodies

The concentration of anti-SEA antibodies in the mouse plasma samples was determined by ELISA technique. The assay was performed with reagent addition, incubation and washing in a sequential manner. In the first step the microtiter plate wells were coated with 1 μg/mL (200 ng/well) of recombinant SEA in 50 mM $NaHCO_3$, pH 9.6. The wells were blocked with 1% (w/v) bovine serum albumin (BSA) in 10 mM PBS, pH 7.4, 0.05% (w/v) Tween 20 (PBST). Samples and standards of affinity purified mouse anti-SEA antibodies were added, diluted in 1% BSA in PBST. A goat anti-mouse IgG antibody, was used as secondary antibody. Next, a biotinylated rabbit anti-goat IgG antibody was added. Thereafter, streptavidin conjugated with horseradish peroxidase was allowed to bind to the biotin groups of the tertiary antibody. The final step was addition of an enzyme substrate. The enzyme reaction was stopped by 1N $H_2SO_4$ and then the absorbance was monitored at 450 nm, with 650 nm as a reference wavelength in an ELISA spectrophotometer. A four-parameter function was adjusted to the obtained concentration/absorbance values of the standards and the unknown concentration of anti-SEA antibodies in samples determined from standard curve. The measuring range was estimated to 0.40-50 ng/mL. The sample dilution was at least 1:100, i.e. the limit of quantification (LOQ) in plasma was 40 ng/mL.

Induction of Anti-SEA Antibodies and Treatment with Chemotherapeutic Agents in C57Bl/6 Mice For induction of a primary anti-SEA response, mice were given 4 intravenous injections of unconjugated SEA (3

μg/mouse/injection, in 0.2 ml PBS containing 1% mouse serum) on days 1, 5, 9 and 13. Starting on day 29 after priming, ABR-214720 treatment was given as daily i.v. injections (10 μg/mouse/injection, in 0.2 ml PBS containing 1% mouse serum) on 4 consecutive days. Gemcitabine was injected (2.4 mg/mouse/injection i.p. in 0.2 ml 0.15M NaCl) four times at three days interval, starting at indicated time points during or after completion of ABR-214720 treatment. At indicated time points blood samples were drained by vena saphena or vena cava for preparation of plasma. Eight mice were included in each experimental group.

Results

As illustrated in Table 16, combination therapy was superior as compared to treatment with single treatment TTS, in maintaining a low anti-SEA antibody titer. Single treatment TTS resulted in significant anti-SEA antibody titers. Gemcitabine was administered beginning during or after the TTS treatment cycle. It was clearly shown that the combination treatment starting both during as well as after the TTS cycle resulted in much lower secondary response anti-SEA antibody titers as compared to the TTS treatment alone (groups 4-7 as compared to group 3).

Determination of Mouse Anti-SEA Antibodies

The concentration of anti-SEA antibodies in the mouse plasma samples was determined by ELISA technique. The assay was performed with reagent addition, incubation and washing in a sequential manner. In the first step the microtiter plate wells were coated with 1 μg/mL (200 ng/well) of recombinant SEA in 50 mM $NaHCO_3$, pH 9.6. The wells were blocked with 1% (w/v) bovine serum albumin (BSA) in 10 mM PBS, pH 7.4, 0.05% (w/v) Tween 20 (PBST). Samples and standards of affinity purified mouse anti-SEA antibodies were added, diluted in 1% BSA in PBST. A goat anti-mouse IgG antibody, was used as secondary antibody. Next, a biotinylated rabbit anti-goat IgG antibody was added. Thereafter, streptavidin conjugated with horseradish peroxidase was allowed to bind to the biotin groups of the tertiary antibody. The final step was addition of an enzyme substrate. The enzyme reaction was stopped by 1N $H_2SO_4$ and then the absorbance was monitored at 450 nm, with 650 nm as a reference wavelength in an ELISA spectrophotometer. A four-parameter function was adjusted to the obtained concentration/absorbance values of the standards and the unknown concentration of anti-SEA antibodies in samples determined from standard curve. The measuring range was estimated to 0.40-50 ng/mL. The sample dilution was at least 1:100, i.e. the limit of quantification (LOQ) in plasma was 40 ng/mL.

TABLE 16

Inhibition of anti-SEA antibodies by combination with chemotherapy.

| Group No | SEA (i.v.) Days 1, 5, 9, 13 | C215Fab-SEA (i.v.) Days 29, 30, 31, 32 | Gemcitabine (i.p) Start day | Anti-SEA day 28 (ng/ml) Primary response | Anti-SEA day 46 (ng/ml) Secondary response | Ratio Secondary/primary response |
|---|---|---|---|---|---|---|
| 1 | Vehicle | Vehicle | Vehicle, d 34 | 59 | 97 | 1.6 |
| 2 | SEA | Vehicle | Vehicle, d 34 | 1073 | 337 | 0.3 |
| 3 | SEA | C215Fab-SEA | Vehicle, d 34 | 333 | 6648 | 20.0 |
| 4 | SEA | C215Fab-SEA | Gemcitabine d 30 | 749 | 166 | 0.2 |
| 5 | SEA | C215Fab-SEA | Gemcitabine d 32 | 353 | 197 | 0.5 |
| 6 | SEA | C215Fab-SEA | Gemcitabine d 33 | 797 | 747 | 0.9 |
| 7 | SEA | C215Fab-SEA | Gemcitabine d 34 | 1139 | 4084 | 3.6 |

Starting gemcitabine treatment before integrated TTS injections as well as after TTS injections resulted in a much lower secondary response anti-SEA antibody titers as compared to the TTS treatment alone. Thus, the combination of TTS with chemotherapeutic agents for example gemcitabine resulted in lowered levels of anti-Superantigen (anti-Sag) antibodies after TTS treatment cycles. Additional TTS treatment cycles can therefore be given without interference from neutralizing high titer anti-Sag antibodies.

Example 16

TTS-Chemotherapeutic Combination Therapy: In vivo-Inhibition of Anti-TTS Antibody Formation It is of vital importance that high titer antibodies do not develop and neutralize the TTS drug. C215Fab-SEA (ABR-214720) in combination with docetaxel was investigated with regard to modulation of the anti-SEA antibody response in C57B1/6 mice. Primary anti-SEA antibody response was induced by immunization with SEA. ABR-214720 treatment was given as 4 daily i.v. injections. For combination studies, docetaxel was injected before completing TTS therapy or shortly after the last ABR-214720 injection.

Animals

Female C57B1/6 mice were used The mice were routinely used at the age of 2 weeks and received food and water ad libitum.

Induction of Anti-SEA Antibodies and Treatment with Chemotherapeutic Agents in C57B1/6 Mice For induction of a primary anti-SEA response, mice were given 4 intravenous injections of unconjugated SEA (3 μg/mouse/injection, in 0.2 ml PBS containing 1% mouse serum) on days 1, 5, 9 and 13. Starting on day 29 after priming, ABR-214720 treatment was given as daily i.v. injections (10 μg/mouse/injection, in 0.2 ml PBS containing 1% mouse serum) on 4 consecutive days. Docetaxel was injected (1 or 2 mg/mouse/injection i.p. in 0.2 ml 10.9-21.7% polysorbate 80, 5.1-10.2% ethanol and 0-0.45% NaCl) once during ABR-214720 treatment or after completion of ABR-214720 treatment. At indicated time points blood samples were drained by vena saphena (day 26) and by vena cava aspiration (day 46) for preparation of plasma. Eleven to seventeen mice were included in each experimental group.

Results

As illustrated in table 17, combination therapy was superior as compared to treatment with single treatment TTS, in maintaining a low anti-SEA antibody titer. Single treatment TTS resulted in significant anti-SEA antibody titers. Docetaxel was administered during or after the TTS treatment cycle. It is clearly shown that the combination treatment both during as well as after the TTS cycle resulted in much lower secondary response anti-SEA antibody titers as compared to the TTS treatment alone (groups 2-7 as compared to group 1).

TABLE 17

Inhibition of anti-SEA antibodies by combination with chemotherapy.

| Group No | SEA (i.v.) Days 1, 5, 9, 13 | C215Fab-SEA (i.v.) Days 29, 30, 31, 32 | Docetaxel 1 or 2 mg (i.p.) Day | Anti-SEA day 26 (ng/ml) Primary response | Anti-SEA day 46 (ng/ml) Secondary response | Ratio Secondary/primary response |
|---|---|---|---|---|---|---|
| 1 | SEA | C215Fab-SEA | Vehicle, d 30 | 1290 | 27700 | 21.5 |
| 2 | SEA | C215Fab-SEA | Docetaxel, d 29 (1 mg) | 572 | 7350 | 12

TABLE 19-continued

Anti-SEA antibody levels in plasma sampled from Cynomolgus monkeys after administration of 5T4Fab-SEA$_{D227A}$ (Days 1-5, Days 29-33) alone or in sequential combination with gemcitabine (Days 8, 15, 22).

| | Administration | | | Anti-SEA antibody levels (mg/L) | | | |
|---|---|---|---|---|---|---|---|
| Group No. | 5T4Fab-SEA$_{D227A}$ | Gemcitabine | Animal No. and sex | Day 1 | Day 14 | Day 21 | Day 29 |
| 2 | — | 65 mg/kg | 757M | <LOQ | <LOQ | <LOQ | <LOQ |
| | | | 762F | <LOQ | <LOQ | 0.87 | <LOQ |
| 3 | 6 µg/kg | 65 mg/kg | 759M | <LOQ | <LOQ | <LOQ | <LOQ |
| | | | 764F | <LOQ | 22.0 | 8.04 | 6.86 |
| 4 | 18 µg/kg | 65 mg/kg | 755M | <LOQ | <LOQ | <LOQ | <LOQ |
| | | | 760F | 2.05 | 14.2 | 7.80 | 5.94 |

Determination of the Concentration of TTS after Combination Treatment Regimen

Blood samples were collected from a suitable vein (different from that used for dosing) into tubes containing lithium heparin and immediately placed in an ice-water bath or Cryo-rack. The blood samples were used to determine concentration of 5T4Fab-SEA$_{D227A}$.

An ELISA method was used to determine the concentration of 5T4Fab-SEA$_{D227A}$ in plasma samples. The method was based on the fact that one part of 5T4Fab-SEA$_{D227A}$ is the Fab fragment of a monoclonal mouse antibody and the other part is the staphylococcal superantigen SEA.

Microtiter plates were coated with a goat anti-mouse kappa antibody in 50 mM NaHCO$_3$, pH 9.6. The plates were washed in phosphate buffered saline containing Tween 20 between every incubation step. After blocking of the wells with bovine serum albumin, the diluted samples, and standards in the range of 0.024-6.25 ng/mL, were added. The next step was addition f a biotinylated rabbit anti-SEA antibody. In the subsequent step, horseradish peroxidase and streptavidin conjugated to a dextran backbone was added. The final step was the addition of substrate, TMB Peroxidase EIA substrate kit. The enzyme reaction was stopped by addition of 1 N H$_2$SO$_4$, and then the absorbance at 450 nm was monitored by an ELISA spectrophotometer. The samples were quantified from the standard curve of 5T4Fab-SEA$_{D227A}$.

The results from the bioanalysis of 5T4FAB-SEA$_{D227A}$ concentration in presented in Table 20.

TABLE 20

Concentrations of 5T4Fab-SEA$_{D227A}$ in plasma sampled from Cynomolgus monkeys after administration of 5T4Fab-SEA$_{D227A}$ (Days 1-5, Days 29-33) alone or in sequential combination with gemcitabine (Days 8, 15, 22).

| | | 5T4Fab-SEA$_{D227A}$ | | | | | | | |
|---|---|---|---|---|---|---|---|---|---|
| | | 18 µg/kg | | 0 µg/kg | | 6 µg/kg | | 18 µg/kg | |
| | | | | Gemcitabine | | | | | |
| | | 0 mg/kg | | 65 mg/kg | | 65 mg/kg | | 65 mg/kg | |
| | | | | | Group | | | | |
| | | 1 | | 2 | | 3 | | 4 | |
| | | | | | Animal no. and sex | | | | |
| Day | Time (h) | 761M | 766F | 757M | 762F | 759M | 764F | 755M | 760F |
| | | Concentration of 5T4Fab-SEA$_{D227A}$ (µg/L) in plasma | | | | | | | |
| 1 | 0 | <LOQ | <LOQ | <LOQ | <LOQ | <LOQ | <LOQ | <LOQ | <LOQ |
| | 0.083 | 385 | 399 | <LOQ | <LOQ | 159 | 158 | 392 | 255 |
| | 1 | 284 | 309 | n.a. | n.a. | 110 | 123 | 293 | 244 |
| | 3 | 239 | 276 | n.a. | n.a. | 70.6 | 89.0 | 204 | 231 |
| | 8 | 97.0 | 74.9 | n.a. | n.a. | 25.7 | 46.6 | 71.5 | 200 |
| 5 | 0 | 21.2 | 10.2 | <LOQ | <LOQ | 3.42 | 32.2 | 10.7 | 255 |
| | 0.083 | 418 | 399 | <LOQ | <LOQ | 156 | 165 | 436 | 590 |
| | 1 | 314 | 266 | n.a. | n.a. | 118 | 142 | 293 | 501 |
| | 3 | 269 | 154 | n.a. | n.a. | 73.2 | 112 | 213 | 434 |
| | 8 | 94.8 | 57.6 | n.a. | n.a. | 24.7 | 70.4 | 64.9 | 398 |
| 29 | 0 | <LOQ | <LOQ | <LOQ | <LOQ | <LOQ | <LOQ | <LOQ | <LOQ |
| | 0.083 | 0.82 | <LOQ | <LOQ | <LOQ | 144 | 84.8 | 433 | 236 |
| | 1 | <LOQ | <LOQ | n.a. | n.a. | 107 | 70.8 | 275 | 215 |
| | 3 | <LOQ | <LOQ | n.a. | n.a. | 72.0 | 50.8 | 224 | 179 |
| | 8 | <LOQ | <LOQ | n.a. | n.a. | 24.9 | 30.1 | 70.8 | 126 |
| 33 | 0 | <LOQ | <LOQ | <LOQ | <LOQ | 1.98 | 4.10 | 14.3 | 57.4 |
| | 0.083 | <LOQ | <LOQ | <LOQ | <LOQ | 97.1 | 48.3 | 449 | 542 |
| | 1 | <LOQ | <LOQ | n.a. | n.a. | 60.7 | 22.1 | 312 | 499 |
| | 3 | <LOQ | <LOQ | n.a. | n.a. | 24.7 | 10.8 | 252 | 464 |
| | 8 | <LOQ | <LOQ | n.a. | n.a. | 6.23 | 5.09 | 77.7 | 352 | n.a. not analyzed

On Days 1 and 5 similar levels of 5T4Fab-SEA$_{D227A}$ were achieved in all animals that received 5T4Fab-SEA$_{D227A}$ (Groups 1, 3 and 4). On Days 29 and 33, 5T4Fab-SEA$_{D227A}$ was below LOQ (limit of quantification, which is 0.5 μg/L) in the animals that received 5T4Fab-SEA$_{D227A}$ alone (Group 1). However on Days 29 and 33, the 5T4Fab-SEA$_{D227A}$ levels in the animals belonging to Groups 3 and 4 were similar to the 5T4Fab-SEA$_{D227A}$ levels found on Days 1 and 5.

Thus, the combination of TTS with chemotherapeutic agents for example gemcitabine resulted in lowered levels of anti-Superantigen (anti-Sag) antibodies after TTS treatment cycles. Additional TTS treatment cycles can therefore be given without interference from neutralizing high titer anti-Sag antibodies.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,554,101
U.S. Pat. No. 5,220,007
U.S. Pat. No. 5,284,760
U.S. Pat. No. 5,284,760
U.S. Pat. No. 5,354,670
U.S. Pat. No. 5,366,878
U.S. Pat. No. 5,389,514
U.S. Pat. No. 5,399,363
U.S. Pat. No. 5,440,013
U.S. Pat. No. 5,446,128
U.S. Pat. No. 5,466,468
U.S. Pat. No. 5,475,085
U.S. Pat. No. 5,519,114
U.S. Pat. No. 5,543,158
U.S. Pat. No. 5,545,716
U.S. Pat. No. 5,629,001
U.S. Pat. No. 5,561,515
U.S. Pat. No. 5,618,914
U.S. Pat. No. 5,635,377
U.S. Pat. No. 5,641,515
U.S. Pat. No. 5,670,155
U.S. Pat. No. 5,672,681
U.S. Pat. No. 5,674,976
U.S. Pat. No. 5,710,245
U.S. Pat. No. 5,725,871
U.S. Pat. No. 5,728,388
U.S. Pat. No. 5,756,353
U.S. Pat. No. 5,780,045
U.S. Pat. No. 5,792,451
U.S. Pat. No. 5,580,579
U.S. Pat. No. 5,804,212
U.S. Pat. No. 5,840,833
U.S. Pat. No. 5,858,363
U.S. Pat. No. 5,859,184
U.S. Pat. No. 5,859,207
U.S. Pat. No. 5,929,237
U.S. Pat. No. 6,042,837
U.S. Pat. No. 6,126,945
U.S. Pat. No. 6,180,097
U.S. Pat. No. 6,197,299
U.S. Pat. No. 6,221,351
U.S. Pat. No. 6,251,385
U.S. Pat. No. 6,338,845
U.S. Pat. No. 6,340,461
U.S. Pat. No. 6,399,332
U.S. Pat. No. 6,447,777
U.S. Pat. No. 6,514,498
U.S. Pat. No. 6,623,308
U.S. Pat. No. 6,632,640
U.S. Pat. No. 6,632,441
U.S. Pat. No. 6,692,746
U.S. Pat. No. 6,713,284
U.S. Patent Application Publication No. 20040126379
U.S. Patent Application Publication No. 20040142464
U.S. Patent Application Publication No. 20030092894
U.S. Patent Application Publication No. 20030039655
U.S. Patent Application Publication No. 20030124142
U.S. Patent Application Publication No. 20030157113
U.S. Patent Application Publication No. 20030175212
U.S. Patent Application Publication No. 20030144474
U.S. Patent Application Publication No. 20030036644
U.S. Patent Application Publication No. 20030009015
U.S. Patent Application Publication No. 20020142389
U.S. Patent Application Publication No. 2002119149
U.S. Patent Application Publication No. 20020177551
U.S. Patent Application Publication No. 20020141981
U.S. Patent Application Publication No. 20020115190
U.S. Patent Application Publication No. 20020086813
U.S. Patent Application Publication No. 20020058032
U.S. Patent Application Publication No. 20020051765
U.S. Patent Application Publication No. 20020039585
U.S. Patent Application Publication No. 20020028211
U.S. Patent Application Publication No. 20020018781
U.S. Patent Application Publication No. 20010046501
International Publication No. WO9201470
International Publication No. WO9601650
International Publication No. WO03002143
International Publication No. WO03020763
International Publication No. WO04050705
International Publication No. WO03002143
International Publication No. WO9960120
International Publication No. WO9960119
International Publication No. WO9301303
International Publication No. WO8907947
European Application No. 610179
European Application No. 766566
Abrahmsén L., et al. EMBO J. 14:2978-86, 1995.
Alpaugh R. K., et al. Clin Cancer Res. 4:1903-14, 1998.
Antonsson P., et al. J Immunol 158:4245-51, 1997.
Bangham et al., J. Mol. Biol., 13:238-252, 1965.
Bird et al., Science. 1988 Oct. 21; 242(4877):423-6.
Bird et al., Science. 242:423-6,1988.
Braisted et al, Proc Natl Acad Sci USA. 93(12):5688-92, 1996.
Burks et al., Proc Natl Acad Sci USA. 94(2):412-7, 1997.
Capaldi et al., Biochem. Biophys. Res. Comm., 76:425, 1977.
Cavallin A., et al. J Biol. Chem. 275:1665-72, 2000.
Chan, O. T. M. and Yang, L.-X. (2000) Cancer Immunol. Immunother. 49:181-185.
Chen (2003) Expert Opin. Ther. Patents. 13:1787-1799.
Cunningham et al., Science. 244(4908):1081-5, 1989.
Davis et al., Basic Methods in Molecular Biology, 1986
Dohlsten, M., et al., (1991) Proc. Natl. Acad. Sci. USA 88:9287-91.
Dohlsten, M., et al., (1994) Proc. Natl. Acad. Sci. USA 91:8495-8949.
Dohlsten, M., et al., (1995) Proc. Natl. Acad. Sci. USA 92:9791-5.
DRUG CARRIERS IN BIOLOGY AND MEDICINE, G. Gregoriadis ed. (1979) pp. 287-341.
Erlandsson et al., (2003) J Mol. Biol. 333:893-905.

Forsberg, G., et al., (1997) J. Biol. Chem. 272:12430-12436.
Gibbs, T. (2005) Scientific American, August 2005, 79-83.
Gomez, G. G., et al., (2001) Cancer Treat. Rev. 27:375-402.
Hakansson, M. et al. J Mol. Biol. 302:527-37, 2000.
Harlow, et al. Antibodies: A Laboratory Manual, 1988.
Johannesson et al., J. Med. Chem. 42:601-608, 1999.
Johannesson et al., J Med. Chem. 1999 Feb. 25; 42(4):601-8.
Johnson et al., Annu Rev Biochem. 1993; 62:685-713.
Kaneda et al., J Biol. Chem., 264(21):12126-12129, 1989.
Kato et al., J Biol. Chem., 266(6):3361-3364, 1991.
Laird & Cherrington, (2003) Expert Opin. Investig. Drugs 12(1):51-64.
Le Poole et al., (2003) Expert Opin. Investig. Drugs. 12:971-981.
Maguire, H. C. J. and Ettore, V. L. (1967) J. Invest. Dermatol 48:39-43.
Marrack and Kappler, Science. 1990 Jun. 1; 248(4959):1066.
Mitchell, M. S: (2003) Cancer Immunol. Immunother. 52:686-692.
Nicolau et al., Methods Enzymol., 149:157-176, 1987.
Papageorgiou A. C. et al. Trends in Microbiology 8: 369-375, 2000.
Remington's Pharmaceutical Sciences, 15th Edition, Chapter 61, pages 1035-1038 and 1570-1580.
Sambrook et. al., In: Molecular Cloning: A Laboratory Manual, 2d Ed., 1989.
Schad E. M., et al. EMBO J. 14:3292-3301, 1995.
Short et al., J Biol. Chem. 270(48):28541-50, 1995.
Smith and Rutledge, Natl Cancer Inst Monogr. 1975 October; 42:169-72.
Sundström M, et al. EMBO J. 15:6832-40, 1996.
Sundström M., et al. J Biol Chem 271:32212-16, 1996.
Szoka and Papahadjopoulos, Proc. Natl. Acad. Sci., 75:4194-4198, 1978.
Tester and Mora, Expert Opin Investig Drugs. 2001 June; 10(6):1021-32.
Ujhazy, P., et al., (2003) Cancer Immunol. Immunother. 52:463-472.
Vita et al., Biopolymers 47:93-100, 1998.
Vita et al., Proc Natl Acad Sci USA. 1995 Jul. 3; 92(14):6404-8.
Warren et al, Biochemistry 35(27):8855-62, 1996.
Weisshoff et al., Eur J. Biochem. 1999 February; 259(3):776-88.
Weisshoff et al., Eur. J. Biochem. 259:776-788, 1999.
Wells et al., Methods. 10(1): 126-34, 1996.
Wong et al., Gene, 10:87-94, 1980.
Yelton et al., J Immunol. 155(4):1994-2004, 1995.
Young et al., N Engl J. Med. 1978 Dec. 7;299(23):1261-6.
Zagozdzon, R. and Golab, J. (2001) Int. J. Oncol. 18:417-424.

Although the present invention and its advantages have been described in detail, it should be understood that various changes, substitutions and alterations can be made herein without departing from the invention as defined by the appended sentences and descriptions. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended statements are intended to include within their scope such processes, machines, manufacture, compositions of matter, means, methods, or steps.

What is claimed is:

1. A method of reducing an antibody response to a tumor-targeted superantigen in a human, while enhancing a T cell response to a tumor-targeted superantigen in a human and increasing the anti-tumor effect of a chemotherapeutic agent in a human, comprising the steps of:

reducing an antibody response to a tumor-targeted superantigen when administered to a human, which antibody response is reduced compared with the antibody response to a tumor-targeted superantigen when administered to a human without a chemotherapeutic agent, while enhancing a T cell response to a tumor-targeted superantigen when administered to a human, which T cell response is enhanced compared with the T cell response to a tumor-targeted superantigen when administered without a chemotherapeutic agent, and increasing the anti-tumor effect of a chemotherapeutic agent when administered to a human, which anti-tumor effect is increased compared with the anti-tumor effect of a chemotherapeutic agent when administered to a human without a tumor-targeted superantigen, by administering non-localized via the circulatory system to the human a tumor-targeted superantigen having the amino acid sequence of SEQ. ID. NO. 7, and not also administering intratumorally or intrathecally to said human said tumor-targeted superantigen, and administering a chemotherapeutic agent.

2. The method of claim 1, wherein the chemotherapeutic agent is a cytostatic drug.

3. The method of claim 2, wherein the cytostatic drug is selected from the group consisting of alkylating agents, antimetabolites, inhibitors of mitosis, anti-tumor antibiotics, and platinum based compounds.

4. The method of claim 2, wherein the cytostatic drug is an alkylating agent selected from the group consisting of busulfan, chlorambucil, cyclophosphamide, melphalan, carmustine, and lomustine.

5. The method of claim 2, wherein the cytostatic drug is an antimetabolite selected from the group consisting of 5-fluorouracil, gemcitabine, and pemetrexed.

6. The method of claim 2, wherein the cytostatic drug is an antitumor antibiotic selected from the group consisting of doxorubicin, daunorubicin, mitomycin, actinomycin D, and bleomycin.

7. The method of claim 2, wherein the cytostatic drug is a mitotic inhibitor selected from the group consisting of paclitaxel, docetaxel, vinblastine, vincristine, and etoposide.

8. The method of claim 2, wherein the cytostatic drug is a platimun based compound selected from the group consisting of cisplatin, carboplatin, and oxaliplatin.

9. The method of claim 1, wherein the human has a cancer selected from the group consisting of lung, breast, colon, kidney, pancreatic, ovarian, stomach, cervix and prostate cancer.

10. A method of reducing an antibody response to a tumor-targeted superantigen in a human, and enhancing a T cell response to a tumor-targeted superantigen in a human, comprising the steps of:
reducing an antibody response to a tumor-targeted superantigen when administered to a human, which antibody response is reduced compared with the antibody response to a tumor-targeted superantigen when administered to a human without a chemotherapeutic agent, and enhancing a T cell response to a tumor-targeted superantigen when administered to a human, which T cell response is enhanced compared with the T cell response to a tumor-targeted superantigen when administered without a chemotherapeutic agent by administering non-localized via the circulatory system to the human a tumor-targeted superantigen having the amino acid sequence of SEQ. ID. NO. 7, and not also administering intratumorally or intrathecally to said human said tumor-targeted superantigen, and administering a chemotherapeutic agent.

11. A method of reducing an antibody response to a tumor-targeted superantigen in a human, and increasing the anti-tumor effect of a chemotherapeutic agent in a human, comprising the steps of:
reducing an antibody response to a tumor-targeted superantigen when administered to a human, which antibody response is reduced compared with the antibody response to a tumor-targeted superantigen when administered to a human without a chemotherapeutic agent, and increasing the anti-tumor effect of a chemotherapeutic agent when administered to a human, which anti-tumor effect is increased compared with the anti-tumor effect of a chemotherapeutic agent when administered to a human without a tumor-targeted superantigen by administering non-localized via the circulatory system to the human a tumor-targeted superantigen having the amino acid sequence of SEQ. ID. NO. 7, and not also administering intratumorally or intrathecally to said human said tumor-targeted superantigen, and administering a chemotherapeutic agent.

12. The method of claim 1, wherein the tumor-targeted superantigen is administered prior to the administration of the chemotherapeutic agent.

13. The method of claim 1, wherein the tumor-targeted superantigen is administered after the administration of the chemotherapeutic agent.

14. The method of claim 1, wherein the tumor-targeted superantigen is administered during the administration of the chemotherapeutic agent.

15. The method of claim 1, wherein the tumor-targeted superantigen is administered between administration of the chemotherapeutic agent.

16. The method of claim 2, wherein the cytostatic drug is docetaxel.

17. The method of claim 2, wherein the cytostatic drug is gemcitabine.

18. The method of claim 2, wherein the cytostatic drug is cisplatin.

19. The method of claim 2, wherein the cytostatic drug is pemetrexed.

20. The method of claim 9, wherein the cancer is lung cancer.

21. The method of claim 9, wherein the cancer is colon cancer.

22. The method of claim 10, wherein the chemotherapeutic agent is a cytostatic drug.

23. The method of claim 22, wherein the cytostatic drug is selected from the group consisting of alkylating agents, antimetabolites, inhibitors of mitosis, anti-tumor antibiotics, and platinum based compounds.

24. The method of claim 22, wherein the cytostatic drug is an alkylating agent selected from the group consisting of busulfan, chlorambucil, cyclophosphamide, melphalan, carmustine, and lomustine.

25. The method of claim 22, wherein the cytostatic drug is an antimetabolite selected from the group consisting of 5-fluorouracil, gemcitabine, and pemetrexed.

26. The method of claim 22, wherein the cytostatic drug is an antitumor antibiotic selected from the group consisting of doxorubicin, daunorubicin, mitomycin, actinomycin D, and bleomycin.

27. The method of claim 22, wherein the cytostatic drug is a mitotic inhibitor selected from the group consisting of paclitaxel, docetaxel, vinblastine, vincristine, and etoposide.

28. The method of claim 22, wherein the cytostatic drug is a platimun based compound selected from the group consisting of cisplatin, carboplatin, and oxaliplatin.

29. The method of claim 10, wherein the human has a cancer selected from the group consisting of lung, breast, colon, kidney, pancreatic, ovarian, stomach, cervix and prostate cancer.

30. The method of claim 10, wherein the tumor-targeted superantigen is administered prior to the administration of the chemotherapeutic agent.

31. The method of claim 10, wherein the tumor-targeted superantigen is administered after the administration of the chemotherapeutic agent.

32. The method of claim 10, wherein the tumor-targeted superantigen is administered during the administration of the chemotherapeutic agent.

33. The method of claim 10, wherein the tumor-targeted superantigen is administered between administration of the chemotherapeutic agent.

34. The method of claim 22, wherein the cytostatic drug is docetaxel.

35. The method of claim 22, wherein the cytostatic drug is gemcitabine.

36. The method of claim 22, wherein the cytostatic drug is cisplatin.

37. The method of claim 22, wherein the cytostatic drug is pemetrexed.

38. The method of claim 29, wherein the cancer is lung cancer.

39. The method of claim 29, wherein the cancer is colon cancer.

40. The method of claim 11, wherein the chemotherapeutic agent is a cytostatic drug.

41. The method of claim 40, wherein the cytostatic drug is selected from the group consisting of alkylating agents, antimetabolites, inhibitors of mitosis, anti-tumor antibiotics, and platinum based compounds.

42. The method of claim 40, wherein the cytostatic drug is an alkylating agent selected from the group consisting of busulfan, chlorambucil, cyclophosphamide, melphalan, carmustine, and lomustine.

43. The method of claim 40, wherein the cytostatic drug is an antimetabolite selected from the group consisting of 5-fluorouracil, gemcitabine, and pemetrexed.

44. The method of claim 40, wherein the cytostatic drug is an antitumor antibiotic selected from the group consisting of doxorubicin, daunorubicin, mitomycin, actinomycin D, and bleomycin.

45. The method of claim 40, wherein the cytostatic drug is a mitotic inhibitor selected from the group consisting of paclitaxel, docetaxel, vinblastine, vincristine, and etoposide.

46. The method of claim 40, wherein the cytostatic drug is a platimun based compound selected from the group consisting of cisplatin, carboplatin, and oxaliplatin.

47. The method of claim 11, wherein the human has a cancer selected from the group consisting of lung, breast, colon, kidney, pancreatic, ovarian, stomach, cervix and prostate cancer.

48. The method of claim 11, wherein the tumor-targeted superantigen is administered prior to the administration of the chemotherapeutic agent.

49. The method of claim 11, wherein the tumor-targeted superantigen is administered after the administration of the chemotherapeutic agent.

50. The method of claim 11, wherein the tumor-targeted superantigen is administered during the administration of the chemotherapeutic agent.

51. The method of claim 11, wherein the tumor-targeted superantigen is administered between administration of the chemotherapeutic agent.

52. The method of claim 40, wherein the cytostatic drug is docetaxel.

53. The method of claim 40, wherein the cytostatic drug is gemcitabine.

54. The method of claim 40, wherein the cytostatic drug is cisplatin.

55. The method of claim 40, wherein the cytostatic drug is pemetrexed.

56. The method of claim 47, wherein the cancer is lung cancer.

57. The method of claim 47, wherein the cancer is colon cancer.

* * * * *

SEQUENCE LISTING

<160> NUMBER OF SEQ ID NOS: 16

<210> SEQ ID NO 1
<211> LENGTH: 233
<212> TYPE: PRT
<213> ORGANISM: Staphylococcus sp

<400> SEQUENCE: 1

```
Ser Glu Lys Ser Glu Glu Ile Asn Glu Lys Asp Leu Arg Lys Lys Ser
1               5                   10                  15

Glu Leu Gln Arg Asn Ala Leu Ser Asn Leu Arg Gln Ile Tyr Tyr Tyr
            20                  25                  30

Asn Glu Lys Ala Ile Thr Glu Asn Lys Glu Ser Asp Asp Gln Phe Leu
        35                  40                  45

Glu Asn Thr Leu Leu Phe Lys Gly Phe Phe Thr Gly His Pro Trp Tyr
    50                  55                  60

Asn Asp Leu Leu Val Asp Leu Gly Ser Lys Asp Ala Thr Asn Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125
```

```
Leu Trp Ile Asp Gly Lys Gln Thr Thr Val Pro Ile Asp Lys Val Lys
        130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
                180                 185                 190

Thr Val Ser Tyr Asp Leu Phe Asp Ala Gln Gly Gln Tyr Pro Asp Thr
            195                 200                 205

Leu Leu Arg Ile Tyr Arg Asp Asn Lys Thr Ile Asn Ser Glu Asn Leu
        210                 215                 220

His Ile Asp Leu Tyr Leu Tyr Thr Thr
225                 230

<210> SEQ ID NO 2
<211> LENGTH: 233
<212> TYPE: PRT
<213> ORGANISM: Staphylococcus sp

<400> SEQUENCE: 2

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Leu
        35                  40                  45

Gln His Thr Ile Leu Phe Lys Gly Phe Phe Thr Asp His Ser Trp Tyr
    50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Lys Val Pro Ile Asn
        115                 120                 125

Leu Trp Leu Asp Gly Lys Gln Asn Thr Val Pro Leu Glu Thr Val Lys
    130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
            180                 185                 190

Ser Val Asn Tyr Asp Leu Phe Gly Ala Gln Gly Gln Tyr Ser Asn Thr
        195                 200                 205

Leu Leu Arg Ile Tyr Arg Asp Asn Lys Thr Ile Asn Ser Glu Asn Met
    210                 215                 220

His Ile Asp Ile Tyr Leu Tyr Thr Ser
225                 230

<210> SEQ ID NO 3
<211> LENGTH: 233
<212> TYPE: PRT
```

```
<213> ORGANISM: Artificial Sequence
<220> FEATURE:
<223> OTHER INFORMATION: Chimeric Protein

<400> SEQUENCE: 3

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Ser Lys Ala Ile Thr Ser Ser Glu Lys Ser Ala Asp Gln Phe Leu
        35                  40                  45

Thr Asn Thr Leu Leu Phe Lys Gly Phe Phe Thr Gly His Pro Trp Tyr
50                  55                  60

Asn Asp Leu Leu Val Asp Leu Gly Ser Thr Ala Ala Thr Ser Glu Tyr
65                  70                  75                  80

Glu Gly Ser Ser Val Asp Leu Tyr Gly Ala Tyr Tyr Gly Tyr Gln Cys
                85                  90                  95

Ala Gly Gly Thr Pro Asn Lys Thr Ala Cys Met Tyr Gly Gly Val Thr
            100                 105                 110

Leu His Asp Asn Asn Arg Leu Thr Glu Glu Lys Val Pro Ile Asn
        115                 120                 125

Leu Trp Ile Asp Gly Lys Gln Thr Thr Val Pro Ile Asp Lys Val Lys
130                 135                 140

Thr Ser Lys Lys Glu Val Thr Val Gln Glu Leu Asp Leu Gln Ala Arg
145                 150                 155                 160

His Tyr Leu His Gly Lys Phe Gly Leu Tyr Asn Ser Asp Ser Phe Gly
                165                 170                 175

Gly Lys Val Gln Arg Gly Leu Ile Val Phe His Ser Ser Glu Gly Ser
            180                 185                 190

Thr Val Ser Tyr Asp Leu Phe Asp Ala Gln Gly Gln Tyr Pro Asp Thr
        195                 200                 205

Leu Leu Arg Ile Tyr Arg Asp Asn Thr Thr Ile Ser Ser Thr Ser Leu
210                 215                 220

Ser Ile Ser Leu Tyr Leu Tyr Thr Thr
225                 230

<210> SEQ ID NO 4
<211> LENGTH: 233
<212> TYPE: PRT
<213> ORGANISM: Artificial Sequence
<220> FEATURE:
<223> OTHER INFORMATION: Mutated Protein

<400> SEQUENCE: 4

Ser Glu Lys Ser Glu Glu Ile Asn Glu Lys Asp Leu Arg Lys Lys Ser
1               5                   10                  15

Glu Leu Gln Gly Thr Ala Leu Gly Asn Leu Lys Gln Ile Tyr Tyr Tyr
            20                  25                  30

Asn Glu Lys Ala Lys Thr Glu Asn Lys Glu Ser His Asp Gln Phe Leu
        35                  40                  45

Gln His Thr Ile Leu Phe Lys Gly Phe Phe Thr Asp His Ser Trp Tyr
50                  55                  60

Asn Asp Leu Leu Val Asp Phe Asp Ser Lys Asp Ile Val Asp Lys Tyr
65                  70                  75                  80

Lys Gly Lys Lys Val Asp Leu Tyr Gly Ala Tyr Tyr Gly Tyr Gln Cys
                85                  90                  95
```

-continued

```
Ala Gly Gly Thr Pro Asn Lys Thr Ala Cys Met Tyr Gly Gly Val Thr
                100                 105                 110

Leu His Asp Asn Asn Arg Leu Thr Glu Glu Lys Lys Val Pro Ile Asn
            115                 120                 125

Leu Trp Leu Asp Gly Lys Gln Asn Thr Val Pro Leu Glu Thr Val Lys
        130                 135                 140

Thr Asn Lys Lys Asn Val Thr Val Gln Glu Leu Asp Leu Gln Ala Arg
145                 150                 155                 160

Arg Tyr Leu Gln Glu Lys Tyr Asn Leu Tyr Asn Ser Asp Val Phe Asp
                165                 170                 175

Gly Lys Val Gln Arg Gly Leu Ile Val Phe His Thr Ser Thr Glu Pro
            180                 185                 190

Ser Val Asn Tyr Asp Leu Phe Gly Ala Gln Gly Gln Tyr Ser Asn Thr
        195                 200                 205

Leu Leu Arg Ile Tyr Arg Asp Asn Lys Thr Ile Asn Ser Glu Asn Met
210                 215                 220

His Ile Ala Ile Tyr Leu Tyr Thr Ser
225                 230
```

<210> SEQ ID NO 5
<211> LENGTH: 679
<212> TYPE: PRT
<213> ORGANISM: Artificial Sequence
<220> FEATURE:
<223> OTHER INFORMATION: Conjugated Protein
<220> FEATURE:
<221> NAME/KEY: MISC_FEATURE
<222> LOCATION: (460)..(679)
<223> OTHER INFORMATION: Light Chain

<400> SEQUENCE: 5

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Tyr Ile Tyr Thr Asn Tyr Asn Gln Glu Phe
    50                  55                  60

Lys Asp Lys Val Thr Leu Thr Val Asp Glu Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Pro Tyr Gly Tyr Asp Glu Tyr Gly Leu Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205
```

```
Ala Ser Ser Thr Lys Val Asp Lys Lys Ile Val Pro Arg Asp Ser Gly
    210                 215                 220

Gly Pro Ser Glu Lys Ser Glu Ile Asn Glu Lys Asp Leu Arg Lys
225                 230                 235                 240

Lys Ser Glu Leu Gln Gly Thr Ala Leu Gly Asn Leu Lys Gln Ile Tyr
                    245                 250                 255

Tyr Tyr Asn Glu Lys Ala Lys Thr Glu Asn Lys Glu Ser His Asp Gln
                260                 265                 270

Phe Leu Gln His Thr Ile Leu Phe Lys Gly Phe Phe Thr Asp His Ser
            275                 280                 285

Trp Tyr Asn Asp Leu Leu Val Asp Phe Asp Ser Lys Asp Ile Val Asp
        290                 295                 300

Lys Tyr Lys Gly Lys Lys Val Asp Leu Tyr Gly Ala Tyr Tyr Gly Tyr
305                 310                 315                 320

Gln Cys Ala Gly Gly Thr Pro Asn Lys Thr Ala Cys Met Tyr Gly Gly
                    325                 330                 335

Val Thr Leu His Asp Asn Asn Arg Leu Thr Glu Glu Lys Lys Val Pro
                340                 345                 350

Ile Asn Leu Trp Leu Asp Gly Lys Gln Asn Thr Val Pro Leu Glu Thr
            355                 360                 365

Val Lys Thr Asn Lys Lys Asn Val Thr Val Gln Glu Leu Asp Leu Gln
        370                 375                 380

Ala Arg Arg Tyr Leu Gln Glu Lys Tyr Asn Leu Tyr Asn Ser Asp Val
385                 390                 395                 400

Phe Asp Gly Lys Val Gln Arg Gly Leu Ile Val Phe His Thr Ser Thr
                    405                 410                 415

Glu Pro Ser Val Asn Tyr Asp Leu Phe Gly Ala Gln Gly Gln Tyr Ser
                420                 425                 430

Asn Thr Leu Leu Arg Ile Tyr Arg Asp Asn Lys Thr Ile Asn Ser Glu
            435                 440                 445

Asn Met His Ile Asp Ile Tyr Leu Tyr Thr Ser Asp Ile Val Met Thr
        450                 455                 460

Gln Ser Pro Ser Ser Leu Thr Val Thr Ala Gly Glu Lys Val Thr Met
465                 470                 475                 480

Asn Cys Lys Ser Ser Gln Ser Leu Leu Asn Ser Arg Asn Gln Lys Asn
                    485                 490                 495

Tyr Leu Thr Trp Tyr Gln Gln Lys Pro Gly Gln Pro Pro Lys Leu Leu
                500                 505                 510

Ile Tyr Trp Ala Ser Thr Arg Glu Ser Gly Val Pro Asp Arg Phe Thr
            515                 520                 525

Gly Ser Gly Ser Gly Thr Asp Phe Thr Leu Thr Ile Ser Ser Val Gln
        530                 535                 540

Ala Glu Asp Leu Ala Val Tyr Tyr Cys Gln Asn Asp Tyr Val Tyr Pro
545                 550                 555                 560

Leu Thr Phe Gly Ala Gly Thr Lys Leu Glu Leu Lys Arg Ala Asp Ala
                    565                 570                 575

Ala Pro Thr Val Ser Ile Phe Pro Pro Ser Ser Glu Gln Leu Thr Ser
                580                 585                 590

Gly Gly Ala Ser Val Val Cys Phe Leu Asn Asn Phe Tyr Pro Lys Asp
            595                 600                 605

Ile Asn Val Lys Trp Lys Ile Asp Gly Ser Glu Arg Gln Asn Gly Val
        610                 615                 620
```

-continued

```
Leu Asn Ser Trp Thr Asp Gln Asp Ser Lys Asp Ser Thr Tyr Ser Met
625                 630                 635                 640

Ser Ser Thr Leu Thr Leu Thr Lys Asp Glu Tyr Glu Arg His Asn Ser
            645                 650                 655

Tyr Thr Cys Glu Ala Thr His Lys Thr Ser Thr Ser Pro Ile Val Lys
        660                 665                 670

Ser Phe Asn Arg Asn Glu Ser
        675

<210> SEQ ID NO 6
<211> LENGTH: 672
<212> TYPE: PRT
<213> ORGANISM: Artificial Sequence
<220> FEATURE:
<223> OTHER INFORMATION: Mutated and Conjugated Protein
<220> FEATURE:
<221> NAME/KEY: misc_feature
<222> LOCATION: (459)..(672)
<223> OTHER INFORMATION: Light Chain

<400> SEQUENCE: 6

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Val Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Ser Gly Gly
    210                 215                 220

Pro Ser Glu Lys Ser Glu Glu Ile Asn Glu Lys Asp Leu Arg Lys Lys
225                 230                 235                 240

Ser Glu Leu Gln Gly Thr Ala Leu Gly Asn Leu Lys Gln Ile Tyr Tyr
                245                 250                 255

Tyr Asn Glu Lys Ala Lys Thr Glu Asn Lys Glu Ser His Asp Gln Phe
            260                 265                 270

Leu Gln His Thr Ile Leu Phe Lys Gly Phe Phe Thr Asp His Ser Trp
        275                 280                 285
```

```
Tyr Asn Asp Leu Leu Val Asp Phe Asp Ser Lys Asp Ile Val Asp Lys
    290                 295                 300

Tyr Lys Gly Lys Lys Val Asp Leu Tyr Gly Ala Tyr Gly Tyr Gln
305                 310                 315                 320

Cys Ala Gly Gly Thr Pro Asn Lys Thr Ala Cys Met Tyr Gly Gly Val
                325                 330                 335

Thr Leu His Asp Asn Asn Arg Leu Thr Glu Glu Lys Lys Val Pro Ile
            340                 345                 350

Asn Leu Trp Leu Asp Gly Lys Gln Asn Thr Val Pro Leu Glu Thr Val
        355                 360                 365

Lys Thr Asn Lys Lys Asn Val Thr Val Gln Glu Leu Asp Leu Gln Ala
    370                 375                 380

Arg Arg Tyr Leu Gln Glu Lys Tyr Asn Leu Tyr Asn Ser Asp Val Phe
385                 390                 395                 400

Asp Gly Lys Val Gln Arg Gly Leu Ile Val Phe His Thr Ser Thr Glu
                405                 410                 415

Pro Ser Val Asn Tyr Asp Leu Phe Gly Ala Gln Gly Gln Tyr Ser Asn
            420                 425                 430

Thr Leu Leu Arg Ile Tyr Arg Asp Asn Lys Thr Ile Asn Ser Glu Asn
        435                 440                 445

Met His Ile Ala Ile Tyr Leu Tyr Thr Ser Ser Ile Val Met Thr Gln
    450                 455                 460

Thr Pro Thr Ser Leu Leu Val Ser Ala Gly Asp Arg Val Thr Ile Thr
465                 470                 475                 480

Cys Lys Ala Ser Gln Ser Val Ser Asn Asp Val Ala Trp Tyr Gln Gln
                485                 490                 495

Lys Pro Gly Gln Ser Pro Lys Leu Leu Ile Ser Tyr Thr Ser Ser Arg
            500                 505                 510

Tyr Ala Gly Val Pro Asp Arg Phe Ser Gly Ser Gly Ser Gly Thr Asp
        515                 520                 525

Phe Thr Leu Thr Ile Ser Ser Val Gln Ala Glu Asp Leu Ala Val Tyr
    530                 535                 540

Phe Cys Gln Gln Asp Tyr Asn Ser Pro Pro Thr Phe Gly Gly Gly Thr
545                 550                 555                 560

Lys Leu Glu Ile Lys Arg Ala Asp Ala Ala Pro Thr Val Ser Ile Phe
                565                 570                 575

Pro Pro Ser Ser Glu Gln Leu Thr Ser Gly Gly Ala Ser Val Val Cys
            580                 585                 590

Phe Leu Asn Asn Phe Tyr Pro Lys Asp Ile Asn Val Lys Trp Lys Ile
        595                 600                 605

Asp Gly Ser Glu Arg Gln Asn Gly Val Leu Asn Ser Trp Thr Asp Gln
    610                 615                 620

Asp Ser Lys Asp Ser Thr Tyr Ser Met Ser Ser Thr Leu Thr Leu Thr
625                 630                 635                 640

Lys Asp Glu Tyr Glu Arg His Asn Ser Tyr Thr Cys Glu Ala Thr His
                645                 650                 655

Lys Thr Ser Thr Ser Pro Ile Val Lys Ser Phe Asn Arg Asn Glu Ser
            660                 665                 670

<210> SEQ ID NO 7
<211> LENGTH: 672
<212> TYPE: PRT
<213> ORGANISM: Artificial Sequence
<220> FEATURE:
```

```
<223> OTHER INFORMATION: Conjugate Protein
<220> FEATURE:
<221> NAME/KEY: MISC_FEATURE
<222> LOCATION: (449)..(672)
<223> OTHER INFORMATION: Light Chain

<400> SEQUENCE: 7

Glu Val Gln Leu Gln Gln Ser Gly Pro Asp Leu Val Lys Pro Gly Ala
 1               5                  10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
 50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Ser Gly Gly
    210                 215                 220

Pro Ser Glu Lys Ser Glu Glu Ile Asn Glu Lys Asp Leu Arg Lys Lys
225                 230                 235                 240

Ser Glu Leu Gln Gly Thr Ala Leu Gly Asn Leu Lys Gln Ile Tyr Tyr
                245                 250                 255

Tyr Asn Ser Lys Ala Ile Thr Ser Ser Glu Lys Ser Ala Asp Gln Phe
            260                 265                 270

Leu Thr Asn Thr Leu Leu Phe Lys Gly Phe Phe Thr Gly His Pro Trp
        275                 280                 285

Tyr Asn Asp Leu Leu Val Asp Leu Gly Ser Thr Ala Ala Thr Ser Glu
    290                 295                 300

Tyr Glu Gly Ser Ser Val Asp Leu Tyr Gly Ala Tyr Tyr Gly Tyr Gln
305                 310                 315                 320

Cys Ala Gly Gly Thr Pro Asn Lys Thr Ala Cys Met Tyr Gly Gly Val
                325                 330                 335

Thr Leu His Asp Asn Asn Arg Leu Thr Glu Glu Lys Lys Val Pro Ile
            340                 345                 350

Asn Leu Trp Ile Asp Gly Lys Gln Thr Thr Val Pro Ile Asp Lys Val
        355                 360                 365

Lys Thr Ser Lys Lys Glu Val Thr Val Gln Glu Leu Asp Leu Gln Ala
    370                 375                 380
```

```
Arg His Tyr Leu His Gly Lys Phe Gly Leu Tyr Asn Ser Asp Ser Phe
385                 390                 395                 400

Gly Gly Lys Val Gln Arg Gly Leu Ile Val Phe His Ser Ser Glu Gly
            405                 410                 415

Ser Thr Val Ser Tyr Asp Leu Phe Asp Ala Gln Gly Gln Tyr Pro Asp
        420                 425                 430

Thr Leu Leu Arg Ile Tyr Arg Asp Asn Thr Thr Ile Ser Ser Thr Ser
            435                 440                 445

Leu Ser Ile Ser Leu Tyr Leu Tyr Thr Thr Ser Ile Val Met Thr Gln
    450                 455                 460

Thr Pro Thr Ser Leu Leu Val Ser Ala Gly Asp Arg Val Thr Ile Thr
465                 470                 475                 480

Cys Lys Ala Ser Gln Ser Val Ser Asn Asp Val Ala Trp Tyr Gln Gln
                485                 490                 495

Lys Pro Gly Gln Ser Pro Lys Leu Leu Ile Ser Tyr Thr Ser Ser Arg
            500                 505                 510

Tyr Ala Gly Val Pro Asp Arg Phe Ser Gly Ser Gly Tyr Gly Thr Asp
        515                 520                 525

Phe Thr Leu Thr Ile Ser Ser Val Gln Ala Glu Asp Ala Ala Val Tyr
            530                 535                 540

Phe Cys Gln Gln Asp Tyr Asn Ser Pro Pro Thr Phe Gly Gly Gly Thr
545                 550                 555                 560

Lys Leu Glu Ile Lys Arg Ala Asp Ala Ala Pro Thr Val Ser Ile Phe
                565                 570                 575

Pro Pro Ser Ser Glu Gln Leu Thr Ser Gly Gly Ala Ser Val Val Cys
            580                 585                 590

Phe Leu Asn Asn Phe Tyr Pro Lys Asp Ile Asn Val Lys Trp Lys Ile
            595                 600                 605

Asp Gly Ser Glu Arg Gln Asn Gly Val Leu Asn Ser Trp Thr Asp Gln
            610                 615                 620

Asp Ser Lys Asp Ser Thr Tyr Ser Met Ser Ser Thr Leu Thr Leu Thr
625                 630                 635                 640

Lys Asp Glu Tyr Glu Arg His Asn Ser Tyr Thr Cys Glu Ala Thr His
                645                 650                 655

Lys Thr Ser Thr Ser Pro Ile Val Lys Ser Phe Asn Arg Asn Glu Ser
            660                 665                 670

<210> SEQ ID NO 8
<211> LENGTH: 671
<212> TYPE: PRT
<213> ORGANISM: Staphylococcus sp

<400> SEQUENCE: 8

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
```

```
                    85                  90                  95
Ala Arg Ser Thr Met Ile Thr Asn Tyr Val Met Asp Tyr Trp Gly Gln
                100                 105                 110
Val Thr Ser Val Thr Val Ser Ser Ala Lys Thr Thr Pro Pro Ser Val
                115                 120                 125
Tyr Pro Leu Ala Pro Gly Ser Ala Ala Gln Thr Asn Ser Met Val Thr
    130                 135                 140
Leu Gly Cys Leu Val Lys Gly Tyr Phe Pro Glu Pro Val Thr Val Thr
145                 150                 155                 160
Trp Asn Ser Gly Ser Leu Ser Ser Gly Val His Thr Phe Pro Ala Val
                165                 170                 175
Leu Gln Ser Asp Leu Tyr Thr Leu Ser Ser Ser Val Thr Val Pro Ser
            180                 185                 190
Ser Thr Trp Pro Ser Glu Thr Val Thr Cys Asn Val Ala His Pro Ala
        195                 200                 205
Ser Ser Thr Lys Val Asp Lys Lys Ile Val Pro Arg Asp Ser Gly Gly
    210                 215                 220
Pro Ser Glu Lys Ser Glu Glu Ile Asn Glu Lys Asp Leu Arg Lys Lys
225                 230                 235                 240
Ser Glu Leu Gln Gly Thr Ala Leu Gly Asn Leu Lys Gln Ile Tyr Tyr
                245                 250                 255
Tyr Asn Glu Lys Ala Lys Thr Glu Asn Lys Glu Ser His Asp Gln Phe
                260                 265                 270
Leu Gln His Thr Ile Leu Phe Lys Gly Phe Phe Thr Asp His Ser Trp
            275                 280                 285
Tyr Asn Asp Leu Leu Val Asp Phe Asp Ser Lys Asp Ile Val Asp Lys
        290                 295                 300
Tyr Lys Gly Lys Lys Val Asp Leu Tyr Gly Ala Tyr Tyr Gly Tyr Gln
305                 310                 315                 320
Cys Ala Gly Gly Thr Pro Asn Lys Thr Ala Cys Met Tyr Gly Gly Val
                325                 330                 335
Thr Leu His Asp Asn Asn Arg Leu Thr Glu Glu Lys Lys Val Pro Ile
                340                 345                 350
Asn Leu Trp Leu Asp Gly Lys Gln Asn Thr Val Pro Leu Glu Thr Val
            355                 360                 365
Lys Thr Asn Lys Lys Asn Val Thr Val Gln Glu Leu Asp Leu Gln Ala
        370                 375                 380
Arg Arg Tyr Leu Gln Glu Lys Tyr Asn Leu Tyr Asn Ser Asp Val Phe
385                 390                 395                 400
Asp Gly Lys Val Gln Arg Gly Leu Ile Val Phe His Thr Ser Thr Glu
                405                 410                 415
Pro Ser Val Asn Tyr Asp Leu Phe Gly Ala Gln Gly Gln Tyr Ser Asn
                420                 425                 430
Thr Leu Leu Arg Ile Tyr Arg Asp Asn Lys Thr Ile Asn Ser Glu Asn
            435                 440                 445
Met His Ile Ala Ile Tyr Leu Tyr Thr Ser Ser Ile Val Met Thr Gln
        450                 455                 460
Thr Pro Thr Ser Leu Leu Val Ser Ala Gly Asp Arg Val Thr Ile Thr
465                 470                 475                 480
Cys Lys Ala Ser Gln Ser Val Ser Asn Asp Val Ala Trp Tyr Gln Gln
                485                 490                 495
Lys Pro Gly Gln Ser Pro Lys Leu Leu Ile Ser Tyr Thr Ser Ser Arg
                500                 505                 510
```

```
Tyr Ala Gly Val Pro Asp Arg Phe Ser Gly Ser Gly Ser Gly Thr Asp
        515                 520                 525

Phe Thr Leu Thr Ile Ser Ser Val Gln Ala Glu Asp Leu Ala Val Tyr
    530                 535                 540

Phe Cys Gln Gln Asp Tyr Asn Ser Pro Pro Thr Phe Gly Gly Gly Thr
545                 550                 555                 560

Lys Leu Glu Ile Lys Arg Ala Asp Ala Ala Pro Thr Val Ser Ile Phe
                565                 570                 575

Pro Pro Ser Ser Glu Gln Leu Thr Ser Gly Gly Ala Ser Val Val Cys
            580                 585                 590

Phe Leu Asn Asn Phe Tyr Pro Lys Asp Ile Asn Val Lys Trp Lys Ile
        595                 600                 605

Asp Gly Ser Glu Arg Gln Asn Gly Val Leu Asn Ser Trp Thr Asp Gln
    610                 615                 620

Asp Ser Lys Asp Ser Thr Tyr Ser Met Ser Ser Thr Leu Thr Leu Thr
625                 630                 635                 640

Lys Asp Glu Tyr Glu Arg His Asn Ser Tyr Thr Cys Glu Ala Thr His
                645                 650                 655

Lys Thr Ser Thr Ser Pro Ile Val Lys Ser Phe Asn Arg Asn Glu
            660                 665                 670

<210> SEQ ID NO 9
<211> LENGTH: 4284
<212> TYPE: DNA
<213> ORGANISM: Staphylococcus sp

<400> SEQUENCE: 9
gaggtccagc ttcagcagtc tggacctgac ctggtgaagc tggggcttc agtgaagata      60 ctccaggtcg aagtcgtcag acctggactg gaccacttcg accccgaag tcacttctat     120 tcctgcaagg cttctggtta ctcattcact ggctactaca tgcactgggt gaagcagagc     180
aggacgttcc gaagaccaat gagtaagtga ccgatgatgt acgtgaccca cttcgtctcg     240
catggaaaga gccttgagtg gattggacgt attaatccta acaatggtgt tactctctac     300
gtacctttct cggaactcac ctaacctgca taattaggat tgttaccaca atgagagatg     360
aaccagaaat tcaaggacaa ggccatatta actgtagaca agtcatccac cacagcctac     420
ttggtcttta agttcctgtt ccggtataat tgacatctgt tcagtaggtg gtgtcggatg     480
atggagctcc gcagcctgac atctgaggac tctgcggtct attactgtgc aagatctact     540
tacctcgagg cgtcggactg tagactcctg agacgccaga taatgacacg ttctagatga     600
atgattacga actatgttat ggactactgg ggtcaagtaa cctcagtcac cgtctcctca     660
tactaatgct tgatacaata cctgatgacc ccagttcatt ggagtcagtg cagaggagt      720 gccaaaacga cacccccatc tgtctatcca ctggccccgg atctgctgc ccaaactaac      780 cggttttgct gtgggggtag acagataggt gaccggggcc ctagacgacg ggtttgattg     840
tccatggtga ccctgggatg cctggtcaag ggctatttcc ctgagccagt gacagtgacc     900
aggtaccact gggaccctac ggaccagttc ccgataaagg gactcggtca ctgtcactgg     960
tggaactctg gatccctgtc cagcggtgtg cacaccttcc cagctgtcct gcagtctgac    1020
accttgagac ctagggacag gtcgccacac gtgtggaagg gtcgacagga cgtcagactg    1080
ctctacactc tgagcagctc agtgactgtc ccctccagca cctggcccag cgagaccgtc    1140
gagatgtgag actcgtcgag tcactgacag gggaggtcgt ggaccgggtc gctctggcag    1200
```

```
acctgcaacg ttgcccaccc ggccagcagc accaaggtgg acaagaaaat tgtgcccagg   1260
tggacgttgc aacgggtggg ccggtcgtcg tggttccacc tgttcttta  acacgggtcc   1320 gactcgggcg gtccgagcga gaaaagcgaa gaaataaatg aaaaagattt gcgaaaaaag   1380
ctgagcccgc caggctcgct cttttcgctt ctttatttac tttttctaaa cgcttttttc   1440
tctgaattgc agggaacagc tttaggcaat cttaaacaaa tctattatta caatgaaaaa   1500
agacttaacg tcccttgtcg aaatccgtta gaatttgttt agataataat gttacttttt   1560
gctaaaactg aaaataaaga gagtcacgat caatttttac agcatactat attgtttaaa   1620
cgattttgac ttttatttct ctcagtgcta gttaaaaatg tcgtatgata taacaaattt   1680
ggctttttta cagatcattc gtggtataac gatttattag tagattttga ttcaaaggat   1740
ccgaaaaaat gtctagtaag caccatattg ctaaataatc atctaaaact aagtttccta   1800
attgttgata aatataaagg gaaaaagta  gacttgtatg gtgcttatta tggttatcaa   1860
taacaactat ttatatttcc cttttttcat ctgaacatac cacgaataat accaatagtt   1920
tgtgcgggtg gtacaccaaa caaaacagct tgtatgtatg gtggtgtaac gttacatgat   1980
acacgcccac catgtggttt gttttgtcga acatacatac caccacattg caatgtacta   2040
aataatcgat tgaccgaaga gaaaaaagtg ccgatcaatt tatggctaga cggtaaacaa   2100
ttattagcta actggcttct cttttttcac ggctagttaa ataccgatct gccatttgtt   2160
aatacagtac ctttggaaac ggttaaaacg aataagaaaa atgtaactgt tcaggagttg   2220
ttatgtcatg gaaacctttg ccaatttttgc ttattctttt tacattgaca agtcctcaac   2280
gatcttcaag caagacgtta tttacaggaa aaatataatt tatataactc tgatgttttt   2340
ctagaagttc gttctgcaat aaatgtcctt tttatattaa atatattgag actacaaaaa   2400
gatgggaagg ttcagagggg attaatcgtg tttcatactt ctacagaacc ttcggttaat   2460
ctacccttcc aagtctcccc taattagcac aaagtatgaa gatgtcttgg aagccaatta   2520
tacgatttat ttggtgctca aggacagtat tcaaatacac tattaagaat atatagagat   2580
atgctaaata aaccacgagt tcctgtcata agtttatgtg ataattctta tatatctcta   2640
aataaaacga ttaactctga aaacatgcat attgctatat atttatatac tagttaataa   2700
ttattttgct aattgagact tttgtacgta taacgatata taaatatatg atcaattatt   2760
gaattaagct tggccgtata ggccactttta caaatacata caggggtat  taatttgaaa   2820 cttaattcga accggcatat ccggtgaaat gtttatgtat gtcccccata attaaacttt   2880
aagaccatgg cactcatcct tgcgtctatt cttgttttt  ctttggtaac caatgcatac   2940
ttctggtacc gtgagtagga acgcagataa gaacaaaaaa gaaaccattg gttacgtatg   3000
gcgagtattg tgatgaccca gactcccact agtctgcttg tttcagcagg agacagggtt   3060
cgctcataac actactgggt ctgagggtga tcagacgaac aaagtcgtcc tctgtcccaa   3120
accataacct gcaaggccag tcagagtgtg agtaatgatg tagcttggta ccaacagaag   3180
tggtattgga cgttccggtc agtctcacac tcattactac atcgaaccat ggttgtcttc   3240
ccagggcagt ctcctaagct gctcatatcc tatacatcca gtcgctacgc tggagtccct   3300
ggtcccgtca gaggattcga cgagtatagg atatgtaggt cagcgatgcg acctcaggga   3360
gatcgcttca gcggcagtgg gtccgggacg gatttcactc tgacgatatc cagtgtacag   3420
ctagcgaagt cgccgtcacc caggccctgc ctaaagtgag actgctatag gtcacatgtc   3480
gctgaagacc tggcagttta tttctgtcag caagattata attctcctcc gacgttcggt   3540
cgacttctgg accgtcaaat aaagacagtc gttctaatat taagaggagg ctgcaagcca   3600
```

| ggaggcacca agctggaaat caaacgggct gatgcggcgc caactgtatc catcttccca | 3660 |
| cctccgtggt tcgacctttà gtttgcccga ctacgccgcg gttgacatag gtagaagggt | 3720 |
| ccatccagtg agcagttaac atctggaggt gcctcagtcg tgtgcttctt gaacaacttc | 3780 |
| ggtaggtcac tcgtcaattg tagacctcca cggagtcagc acacgaagaa cttgttgaag | 3840 |
| tacccçaaag acatcaatgt caagtggaag attgatggca gtgaacgaca aaatggcgtc | 3900 |
| atggggtttc tgtagttaca gttcaccttc taactaccgt cacttgctgt tttaccgcag | 3960 |
| ctgaacagtt ggactgatca ggacagcaaa gacagcacct acagcatgag cagcaccctc | 4020 |
| gacttgtcaa cctgactagt cctgtcgttt ctgtcgtgga tgtcgtactc gtcgtgggag | 4080 |
| acgttgacca aggacgagta tgaacgacat aacagctata cctgtgaggc cactcacaag | 4140 |
| tgcaactggt tcctgctcat acttgctgta ttgtcgatat ggacactccg gtgagtgttc | 4200 |
| acatcaactt cacccattgt caagagcttc aaccgtaatg agtgtagttg aagtgggtaa | 4260 |
| cagttctcga agttggcatt actc | 4284 |

<210> SEQ ID NO 10
<211> LENGTH: 2142
<212> TYPE: DNA
<213> ORGANISM: Staphylococcus sp

<400> SEQUENCE: 10

| gaggtccagc ttcagcagtc tggacctgac ctggtgaagc ctggggcttc agtgaagata | 60 |
| tcctgcaagg cttctggtta ctcattcact ggctactaca tgcactgggt gaagcagagc | 120 |
| catggaaaga gccttgagtg gattggacgt attaatccta acaatggtgt tactctctac | 180 |
| aaccagaaat tcaaggacaa ggccatatta actgtagaca agtcatccac cacagcctac | 240 |
| atggagctcc gcagcctgac atctgaggac tctgcggtct attactgtgc aagatctact | 300 |
| atgattacga actatgttat ggactactgg ggtcaagtaa cctcagtcac cgtctcctca | 360 |
| gccaaaacga caccccatc tgtctatcca ctggccccgg gatctgctgc ccaaactaac | 420 |
| tccatggtga ccctgggatg cctggtcaag ggctatttcc ctgagccagt gacagtgacc | 480 |
| tggaactctg gatccctgtc cagcggtgtg cacaccttcc cagctgtcct gcagtctgac | 540 |
| ctctacactc tgagcagctc agtgactgtc ccctccagca cctggcccag cgagaccgtc | 600 |
| acctgcaacg ttgcccaccc ggccagcagc accaaggtgg acaagaaaat tgtgcccagg | 660 |
| gactcgggcg gtccgagcga gaaaagcgaa gaaataaatg aaaagagattt gcgaaaaaag | 720 |
| tctgaattgc agggaacagc tttaggcaat cttaaacaaa tctattatta caatgaaaaa | 780 |
| gctaaaactg aaaataaaga gagtcacgat caattttttac agcatactat attgtttaaa | 840 |
| ggctttttta cagatcattc gtggtataac gatttattag tagattttga ttcaaaggat | 900 |
| attgttgata aatataaagg gaaaaaagta gacttgtatg gtgcttatta tggttatcaa | 960 |
| tgtgcgggtg gtacaccaaa caaaacagct tgtatgtatg gtggtgtaac gttacatgat | 1020 |
| aataatcgat tgaccgaaga gaaaaaagtg ccgatcaatt tatggctaga cggtaaacaa | 1080 |
| aatacagtac ctttggaaac ggttaaaacg aataagaaaa atgtaactgt tcaggagttg | 1140 |
| gatcttcaag caagacgtta tttacaggaa aaatataatt tatataactc tgatgttttt | 1200 |
| gatgggaagg ttcagagggg attaatcgtg tttcatactt ctacagaacc ttcggttaat | 1260 |
| tacgatttat ttggtgctca aggacagtat tcaaatacac tattaagaat atatagagat | 1320 |
| aataaaacga ttaactctga aaacatgcat attgctatat atttatatac tagttaataa | 1380 |

```
gaattaagct tggccgtata ggccacttta caaatacata caggggggtat taatttgaaa    1440 aagaccatgg cactcatcct tgcgtctatt cttgttttt ctttggtaac caatgcatac      1500
gcgagtattg tgatgaccca gactcccact agtctgcttg tttcagcagg agacagggtt    1560
accataacct gcaaggccag tcagagtgtg agtaatgatg tagcttggta ccaacagaag    1620
ccagggcagt ctcctaagct gctcatatcc tatacatcca gtcgctacgc tggagtccct    1680
gatcgcttca gcggcagtgg gtccgggacg gatttcactc tgacgatatc cagtgtacag    1740
gctgaagacc tggcagttta tttctgtcag caagattata attctcctcc gacgttcggt    1800
ggaggcacca agctggaaat caaacgggct gatgcggcgc caactgtatc catcttccca    1860
ccatccagtg agcagttaac atctggaggt gcctcagtcg tgtgcttctt gaacaacttc    1920
taccccaaag acatcaatgt caagtggaag attgatggca gtgaacgaca aaatggcgtc    1980
ctgaacagtt ggactgatca ggacagcaaa gacagcacct acagcatgag cagcaccctc    2040
acgttgacca aggacgagta tgaacgacat aacagctata cctgtgaggc cactcacaag    2100
acatcaactt cacccattgt caagagcttc aaccgtaatg ag                       2142

<210> SEQ ID NO 11
<211> LENGTH: 678
<212> TYPE: PRT
<213> ORGANISM: Staphylococcus sp

<400> SEQUENCE: 11

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Tyr Ile Tyr Thr Asn Tyr Asn Gln Glu Phe
    50                  55                  60

Lys Asp Lys Val Thr Leu Thr Val Asp Glu Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Pro Tyr Gly Tyr Asp Glu Tyr Gly Leu Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
        195                 200                 205

Ala Ser Ser Thr Lys Val Asp Lys Lys Ile Val Pro Arg Asp Ser Gly
    210                 215                 220

Gly Pro Ser Glu Lys Ser Glu Glu Ile Asn Glu Lys Asp Leu Arg Lys
225                 230                 235                 240
```

-continued

```
Lys Ser Glu Leu Gln Gly Thr Ala Leu Gly Asn Leu Lys Gln Ile Tyr
            245                 250                 255

Tyr Tyr Asn Glu Lys Ala Lys Thr Glu Asn Lys Glu Ser His Asp Gln
        260                 265                 270

Phe Leu Gln His Thr Ile Leu Phe Lys Gly Phe Phe Thr Asp His Ser
            275                 280                 285

Trp Tyr Asn Asp Leu Leu Val Asp Phe Asp Ser Lys Asp Ile Val Asp
290                 295                 300

Lys Tyr Lys Gly Lys Lys Val Asp Leu Tyr Gly Ala Tyr Tyr Gly Tyr
305                 310                 315                 320

Gln Cys Ala Gly Gly Thr Pro Asn Lys Thr Ala Cys Met Tyr Gly Gly
                325                 330                 335

Val Thr Leu His Asp Asn Asn Arg Leu Thr Glu Glu Lys Lys Val Pro
            340                 345                 350

Ile Asn Leu Trp Leu Asp Gly Lys Gln Asn Thr Val Pro Leu Glu Thr
            355                 360                 365

Val Lys Thr Asn Lys Lys Asn Val Thr Val Gln Glu Leu Asp Leu Gln
    370                 375                 380

Ala Arg Arg Tyr Leu Gln Glu Lys Tyr Asn Leu Tyr Asn Ser Asp Val
385                 390                 395                 400

Phe Asp Gly Lys Val Gln Arg Gly Leu Ile Val Phe His Thr Ser Thr
                405                 410                 415

Glu Pro Ser Val Asn Tyr Asp Leu Phe Gly Ala Gln Gly Gln Tyr Ser
            420                 425                 430

Asn Thr Leu Leu Arg Ile Tyr Arg Asp Asn Lys Thr Ile Asn Ser Glu
        435                 440                 445

Asn Met His Ile Asp Ile Tyr Leu Tyr Thr Ser Asp Ile Val Met Thr
    450                 455                 460

Gln Ser Pro Ser Ser Leu Thr Val Thr Ala Gly Glu Lys Val Thr Met
465                 470                 475                 480

Asn Cys Lys Ser Ser Gln Ser Leu Leu Asn Ser Arg Asn Gln Lys Asn
                485                 490                 495

Tyr Leu Thr Trp Tyr Gln Lys Pro Gly Gln Pro Pro Lys Leu Leu
            500                 505                 510

Ile Tyr Trp Ala Ser Thr Arg Glu Ser Gly Val Pro Asp Arg Phe Thr
    515                 520                 525

Gly Ser Gly Ser Gly Thr Asp Phe Thr Leu Thr Ile Ser Ser Val Gln
530                 535                 540

Ala Glu Asp Leu Ala Val Tyr Tyr Cys Gln Asn Asp Tyr Val Tyr Pro
545                 550                 555                 560

Leu Thr Phe Gly Ala Gly Thr Lys Leu Glu Leu Lys Arg Ala Asp Ala
                565                 570                 575

Ala Pro Thr Val Ser Ile Phe Pro Pro Ser Glu Gln Leu Thr Ser
            580                 585                 590

Gly Gly Ala Ser Val Val Cys Phe Leu Asn Asn Phe Tyr Pro Lys Asp
        595                 600                 605

Ile Asn Val Lys Trp Lys Ile Asp Gly Ser Glu Arg Gln Asn Gly Val
    610                 615                 620

Leu Asn Ser Trp Thr Asp Gln Asp Ser Lys Asp Ser Thr Tyr Ser Met
625                 630                 635                 640

Ser Ser Thr Leu Thr Leu Thr Lys Asp Glu Tyr Glu Arg His Asn Ser
                645                 650                 655

Tyr Thr Cys Glu Ala Thr His Lys Thr Ser Thr Ser Pro Ile Val Lys
```

Ser Phe Asn Arg Asn Glu
    675

<210> SEQ ID NO 12
<211> LENGTH: 4326
<212> TYPE: DNA
<213> ORGANISM: Staphylococcus sp

<400> SEQUENCE: 12

| | | | |
|---|---|---|---|
| caggtccaac tgcagcagcc tggggctgaa ctggtgaggc tggggcttc agtgaagctg | 60 |
| gtccaggttg acgtcgtcgg accccgactt gaccactccg gaccccgaag tcacttcgac | 120 |
| tcctgcaagg cttctggcta cccttcacc aactactgga taaactgggt gaagcagagg | 180 |
| aggacgttcc gaagaccgat gtggaagtgg ttgatgacct atttgaccca cttcgtctcc | 240 |
| cctggacaag gccttgagtg gatcggaaat atttatcctt cttatatta tactaactac | 300 |
| ggacctgttc cggaactcac ctagccttta taaataggaa gaatataaat atgattgatg | 360 |
| aatcaagagt tcaaggacaa ggtcacattg actgtagacg aatcctccag cacagcctac | 420 |
| ttagttctca agttcctgtt ccagtgtaac tgacatctgc ttaggaggtc gtgtcggatg | 480 |
| atgcagctca gcagcccgac atctgaggac tctgcggtct attactgtac aagatcccct | 540 |
| tacgtcgagt cgtcgggctg tagactcctg agacgccaga taatgacatg ttctagggga | 600 |
| tatggttacg acgagtatgg tctggactac tggggtcaag gaacctcagt caccgtctcc | 660 |
| ataccaatgc tgctcatacc agacctgatg accccagttc cttggagtca gtggcagagg | 720 |
| tcagccaaaa caacacccc atctgtctat ccactggccc cgggatctgc tgcccaaact | 780 |
| agtcggtttt gttgtgggg tagacagata ggtgaccggg gccctagacg acgggtttga | 840 |
| aactccatgg tgaccctggg atgcctggtc aagggctatt ccctgagcc agtgacagtg | 900 |
| ttgaggtacc actgggaccc tacgaccag ttcccgataa agggactcgg tcactgtcac | 960 |
| acctggaact ctggatctct gtccagcggt gtgcacacct cccagctgt cctccagtct | 1020 |
| tggaccttga gacctagaga caggtcgcca cacgtgtgga agggtcgaca ggaggtcaga | 1080 |
| gacctctaca ctctgagcag ctcagtgact gtcccctcca gcacctggcc cagcgagacc | 1140 |
| ctggagatgt gagactcgtc gagtcactga caggggaggt cgtggaccgg tcgctctgg | 1200 |
| gtcacctgca acgttgccca cccggccagc agcaccaagg tggacaagaa aattgtgccc | 1260 |
| cagtggacgt tgcaacgggt gggccggtcg tcgtggttcc acctgttctt ttaacacggg | 1320 |
| agggactcgg gcggtccgag cgagaaaagc gaagaaataa atgaaaaaga tttgcgaaaa | 1380 |
| tccctgaggc cgccaggctc gctcttttcg cttctttatt tacttttct aaacgctttt | 1440 |
| aagtctgaat tgcagggaac agcttaggc aatcttaaac aaatctatta ttacaatgaa | 1500 |
| ttcagactta acgtcccttg tcgaaatccg ttagaatttg tttagataat aatgttactt | 1560 |
| aaagctaaaa ctgaaaataa agagagtcac gatcaatttt tacagcatac tatattgttt | 1620 |
| tttcgatttt gacttttatt tctctcagtg ctagttaaaa atgtcgtatg atataacaaa | 1680 |
| aaaggctttt ttacagatca ttcgtggtat aacgattat tagtagattt tgattcaaag | 1740 |
| tttccgaaaa aatgtctagt aagcaccata ttgctaaata atcatctaaa actaagtttc | 1800 |
| gatattgttg ataaatataa agggaaaaaa gtagacttgt atggtgctta ttatggttat | 1860 |
| ctataacaac tatttatatt tccctttttt catctgaaca taccacgaat aataccaata | 1920 |
| caatgtgcgg gtggtacacc aaacaaaaca gcttgtatgt atggtggtgt aacgttacat | 1980 |

```
gttacacgcc caccatgtgg tttgttttgt cgaacataca taccaccaca ttgcaatgta    2040
gataataatc gattgaccga agagaaaaaa gtgccgatca atttatggct agacggtaaa    2100
ctattattag ctaactggct tctctttttt cacggctagt taaataccga tctgccattt    2160
caaaatacag tacctttgga aacggttaaa acgaataaga aaaatgtaac tgttcaggag    2220
gttttatgtc atggaaacct ttgccaattt tgcttattct ttttacattg acaagtcctc    2280
ttggatcttc aagcaagacg ttatttacag gaaaaatata atttatataa ctctgatgtt    2340
aacctagaag ttcgttctgc aataaatgtc cttttatat taaatatatt gagactacaa     2400
tttgatggga aggttcagag gggattaatc gtgtttcata cttctacaga accttcggtt    2460
aaactaccct tccaagtctc ccctaattag cacaaagtat gaagatgtct tggaagccaa    2520
aattacgatt tatttggtgc tcaaggacag tattcaaata cactattaag aatatataga    2580
ttaatgctaa ataaaccacg agttcctgtc ataagtttat gtgataattc ttatatatct    2640
gataataaaa cgattaactc tgaaaacatg catattgata tatatttata tacaagttaa    2700
ctattatttt gctaattgag acttttgtac gtataactat atataaatat atgttcaatt    2760
taagaattaa gcttggccgt ataggccact ttacaaatac atacagggg tattaatttg      2820 attcttaatt cgaaccggca tatccggtga aatgtttatg tatgtccccc ataattaaac    2880
aaaaagacca tggcactcat ccttgcgtct attcttgttt tttctttggt aaccaatgca    2940 ttttctggt accgtgagta ggaacgcaga taagaacaaa aaagaaacca ttggttacgt      3000
tacgcggaca ttgtgatgac tcagtctcca tcctccctga ctgtgacagc aggagagaag    3060
atgcgcctgt aacactactg agtcagaggt aggagggact gacactgtcg tcctctcttc    3120
gtcactatga actgcaagtc cagtcagagt ctgttaaaca gtagaaatca aaagaactac    3180
cagtgatact tgacgttcag gtcagtctca gacaatttgt catctttagt tttcttgatg    3240
ttgacctggt accagcagaa accagggcag cctcctaaac tgttgatata ctgggcatcc    3300
aactggacca tggtcgtctt tggtcccgtc ggaggatttg acaactatat gacccgtagg    3360
actagggaat ctggggtccc tgatcgcttc acaggcagtg gatctggaac agatttcact    3420
tgatccctta gaccccaggg actagcgaag tgtccgtcac ctagaccttg tctaaagtga    3480
ctcaccatca gcagtgtgca ggctgaagac ctggcagttt attactgtca gaatgattat    3540
gagtggtagt cgtcacacgt ccgacttctg gaccgtcaaa taatgacagt cttactaata    3600
gtttatccgc tcacgttcgg tgctgggacc aagctggagc tgaaacgggc tgatgcggcg    3660
caaataggcg agtgcaagcc acgaccctgg ttcgacctcg actttgcccg actacgccgc    3720
ccaactgtat ccatcttccc accatccagt gagcagttaa catctggagg tgcctcagtc    3780
ggttgacata ggtagaaggg tggtaggtca ctcgtcaatt gtagacctcc acggagtcag    3840
gtgtgcttct tgaacaactt ctaccccaaa gacatcaatg tcaagtggaa gattgatggc    3900
cacacgaaga acttgttgaa gatggggttt ctgtagttac agttcacctt ctaactaccg    3960
agtgaacgac aaaatggcgt cctgaacagt tggactgatc aggacagcaa agacagcacc    4020
tcacttgctg ttttaccgca ggacttgtca acctgactag tcctgtcgtt tctgtcgtgg    4080
tacagcatga gcagcaccct cacgttgacc aaggacgagt atgaacgaca taacagctat    4140
atgtcgtact cgtcgtggga gtgcaactgg ttcctgctca tacttgctgt attgtcgata    4200
acctgtgagg ccactcacaa gacatcaact tcacccattg tcaagagctt caaccgtaat    4260
tggacactcc ggtgagtgtt ctgtagttga agtgggtaac agttctcgaa gttggcatta    4320
gagctc                                                               4326
```

<210> SEQ ID NO 13
<211> LENGTH: 2163
<212> TYPE: DNA
<213> ORGANISM: Staphylococcus sp

<400> SEQUENCE: 13

| | | | | | |
|---|---|---|---|---|---|
| caggtccaac | tgcagcagcc | tggggctgaa | ctggtgaggc | ctggggcttc | agtgaagctg | 60 |
| tcctgcaagg | cttctggcta | caccttcacc | aactactgga | taaactgggt | gaagcagagg | 120 |
| cctggacaag | gccttgagtg | gatcggaaat | atttatcctt | cttatattta | tactaactac | 180 |
| aatcaagagt | tcaaggacaa | ggtcacattg | actgtagacg | aatcctccag | cacagcctac | 240 |
| atgcagctca | gcagcccgac | atctgaggac | tctgcggtct | attactgtac | aagatcccct | 300 |
| tatggttacg | acgagtatgg | tctggactac | tggggtcaag | gaacctcagt | caccgtctcc | 360 |
| tcagccaaaa | caacaccccc | atctgtctat | ccactggccc | cgggatctgc | tgcccaaact | 420 |
| aactccatgg | tgaccctggg | atgcctggtc | aagggctatt | ccctgagcc | agtgacagtg | 480 |
| acctggaact | ctggatctct | gtccagcggt | gtgcacacct | tcccagctgt | cctccagtct | 540 |
| gacctctaca | ctctgagcag | ctcagtgact | gtcccctcca | gcacctggcc | cagcgagacc | 600 |
| gtcacctgca | acgttgccca | cccggccagc | agcaccaagg | tggacaagaa | aattgtgccc | 660 |
| agggactcgg | gcggtccgag | cgagaaaagc | gaagaaataa | atgaaaaaga | tttgcgaaaa | 720 |
| aagtctgaat | tgcagggaac | agctttaggc | aatcttaaac | aaatctatta | ttacaatgaa | 780 |
| aaagctaaaa | ctgaaaataa | agagagtcac | gatcaatttt | tacagcatac | tatattgttt | 840 |
| aaaggctttt | ttacagatca | ttcgtggtat | aacgatttat | tagtagattt | tgattcaaag | 900 |
| gatattgttg | ataaatataa | agggaaaaaa | gtagacttgt | atggtgctta | ttatggttat | 960 |
| caatgtgcgg | gtggtacacc | aaacaaaaca | gcttgtatgt | atggtggtgt | aacgttacat | 1020 |
| gataataatc | gattgaccga | agagaaaaaa | gtgccgatca | atttatggct | agacggtaaa | 1080 |
| caaaatacag | tacctttgga | aacggttaaa | acgaataaga | aaatgtaac | tgttcaggag | 1140 |
| ttggatcttc | aagcaagacg | ttatttacag | gaaaaatata | atttatataa | ctctgatgtt | 1200 |
| tttgatggga | aggttcagag | gggattaatc | gtgtttcata | cttctacaga | accttcggtt | 1260 |
| aattacgatt | tatttggtgc | tcaaggacag | tattcaaata | cactattaag | aatatataga | 1320 |
| gataataaaa | cgattaactc | tgaaaacatg | catattgata | tatatttata | tacaagttaa | 1380 |
| taagaattaa | gcttggccgt | ataggccact | ttacaaatac | atacaggggg | tattaatttg | 1440 |
| aaaaagacca | tggcactcat | ccttgcgtct | attcttgttt | tttctttggt | aaccaatgca | 1500 |
| tacgcggaca | ttgtgatgac | tcagtctcca | tcctccctga | ctgtgacagc | aggagagaag | 1560 |
| gtcactatga | actgcaagtc | cagtcagagt | ctgttaaaca | gtagaaatca | aaagaactac | 1620 |
| ttgacctggt | accagcagaa | accagggcag | cctcctaaac | tgttgatata | ctgggcatcc | 1680 |
| actagggaat | ctggggtccc | tgatcgcttc | acaggcagtg | gatctggaac | agatttcact | 1740 |
| ctcaccatca | gcagtgtgca | ggctgaagac | ctggcagttt | attactgtca | gaatgattat | 1800 |
| gtttatccgc | tcacgttcgg | tgctgggacc | aagctggagc | tgaaacgggc | tgatgcggcg | 1860 |
| ccaactgtat | ccatcttccc | accatccagt | gagcagttaa | catctggagg | tgcctcagtc | 1920 |
| gtgtgcttct | tgaacaactt | ctaccccaaa | gacatcaatg | tcaagtggaa | gattgatggc | 1980 |
| agtgaacgac | aaaatggcgt | cctgaacagt | tggactgatc | aggacagcaa | agacagcacc | 2040 |
| tacagcatga | gcagcaccct | cacgttgacc | aaggacgagt | atgaacgaca | taacagctat | 2100 |

```
acctgtgagg ccactcacaa gacatcaact tcacccattg tcaagagctt caaccgtaat    2160
gag                                                                 2163
```

<210> SEQ ID NO 14
<211> LENGTH: 671
<212> TYPE: PRT
<213> ORGANISM: Staphylococcus sp

<400> SEQUENCE: 14

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Pro Gly Lys Gly Leu Glu Trp Ile
        35                  40                  45

Gly Arg Ile Asn Pro Asn Asn Gly Val Thr Leu Tyr Asn Gln Lys Phe
    50                  55                  60

Lys Asp Lys Ala Thr Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Met Ile Thr Asn Tyr Val Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Ser Gly Gly
    210                 215                 220

Pro Ser Glu Lys Ser Glu Glu Ile Asn Glu Lys Asp Leu Arg Lys Lys
225                 230                 235                 240

Ser Glu Leu Gln Gly Thr Ala Leu Gly Asn Leu Lys Gln Ile Tyr Tyr
                245                 250                 255

Tyr Asn Ser Lys Ala Ile Thr Ser Ser Glu Lys Ser Ala Asp Gln Phe
            260                 265                 270

Leu Thr Asn Thr Leu Leu Phe Lys Gly Phe Phe Thr Gly His Pro Trp
        275                 280                 285

Tyr Asn Asp Leu Leu Val Asp Leu Gly Ser Thr Ala Ala Thr Ser Glu
    290                 295                 300

Tyr Glu Gly Ser Ser Val Asp Leu Tyr Gly Ala Tyr Tyr Gly Tyr Gln
305                 310                 315                 320

Cys Ala Gly Gly Thr Pro Asn Lys Thr Ala Cys Met Tyr Gly Gly Val
                325                 330                 335

Thr Leu His Asp Asn Asn Arg Leu Thr Glu Glu Lys Lys Val Pro Ile
            340                 345                 350

Asn Leu Trp Ile Asp Gly Lys Gln Thr Thr Val Pro Ile Asp Lys Val
```

355                 360                 365
Lys Thr Ser Lys Lys Glu Val Thr Val Gln Glu Leu Asp Leu Gln Ala
            370                 375                 380
Arg His Tyr Leu His Gly Lys Phe Gly Leu Tyr Asn Ser Asp Ser Phe
385                 390                 395                 400
Gly Gly Lys Val Gln Arg Gly Leu Ile Val Phe His Ser Ser Glu Gly
                405                 410                 415
Ser Thr Val Ser Tyr Asp Leu Phe Asp Ala Gln Gly Gln Tyr Pro Asp
            420                 425                 430
Thr Leu Leu Arg Ile Tyr Arg Asp Asn Thr Thr Ile Ser Ser Thr Ser
            435                 440                 445
Leu Ser Ile Ser Leu Tyr Leu Tyr Thr Thr Ser Ile Val Met Thr Gln
450                 455                 460
Thr Pro Thr Ser Leu Leu Val Ser Ala Gly Asp Arg Val Thr Ile Thr
465                 470                 475                 480
Cys Lys Ala Ser Gln Ser Val Ser Asn Asp Val Ala Trp Tyr Gln Gln
                485                 490                 495
Lys Pro Gly Gln Ser Pro Lys Leu Leu Ile Ser Tyr Thr Ser Ser Arg
            500                 505                 510
Tyr Ala Gly Val Pro Asp Arg Phe Ser Gly Ser Gly Tyr Gly Thr Asp
            515                 520                 525
Phe Thr Leu Thr Ile Ser Ser Val Gln Ala Glu Asp Ala Ala Val Tyr
            530                 535                 540
Phe Cys Gln Gln Asp Tyr Asn Ser Pro Pro Thr Phe Gly Gly Gly Thr
545                 550                 555                 560
Lys Leu Glu Ile Lys Arg Ala Asp Ala Ala Pro Thr Val Ser Ile Phe
                565                 570                 575
Pro Pro Ser Ser Glu Gln Leu Thr Ser Gly Gly Ala Ser Val Val Cys
            580                 585                 590
Phe Leu Asn Asn Phe Tyr Pro Lys Asp Ile Asn Val Lys Trp Lys Ile
            595                 600                 605
Asp Gly Ser Glu Arg Gln Asn Gly Val Leu Asn Ser Trp Thr Asp Gln
610                 615                 620
Asp Ser Lys Asp Ser Thr Tyr Ser Met Ser Ser Thr Leu Thr Leu Thr
625                 630                 635                 640
Lys Asp Glu Tyr Glu Arg His Asn Ser Tyr Thr Cys Glu Ala Thr His
                645                 650                 655
Lys Thr Ser Thr Ser Pro Ile Val Lys Ser Phe Asn Arg Asn Glu
            660                 665                 670

<210> SEQ ID NO 15
<211> LENGTH: 4264
<212> TYPE: DNA
<213> ORGANISM: Staphylococcus sp

<400> SEQUENCE: 15
gaggtccagc ttcagcagtc tggacctgac ctggtgaagc ctggggcttc agtgaagata      60
ctccaggtcg aagtcgtcag acctggactg gaccacttcg accccgaagt cacttctat     120 tcctgcaagg cttctggtta ctcattcact ggctactaca tgcactgggt gaagcagagc     180
aggacgttcc gaagaccaat gagtaagtga ccgatgatgt acgtgaccca cttcgtctcg     240
ccgggaaaag gccttgagtg gattggacgt attaatccta acaatggtgt tactctctac     300
ggcccttttc cggaactcac ctaacctgca taattaggat tgttaccaca atgagagatg     360

```
aaccagaaat tcaaggacaa ggccacgtta actgtagaca agtcatccac cacagcctac    420 ttggtctttα agttcctgtt ccggtgcaat tgacatctgt tcagtaggtg gtgtcggatg    480
atggagctcc gcagcctgac atctgaggac tctgcggtct attactgtgc aagatctact    540
tacctcgagg cgtcggactg tagactcctg agacgccaga taatgacacg ttctagatga    600
atgattacga actatgttat ggactactgg ggtcaaggga cgtcagtcac cgtctcctca    660
tactaatgct tgatacaata cctgatgacc ccagttccct gcagtcagtg gcagaggagt    720
gccaaaacga caccccatc tgtctatcca ctggccccgg gatctgctgc ccaaactaac     780
cggttttgct gtgggggtag acagataggt gaccggggcc ctagacgacg ggtttgattg    840
tccatggtga ccctgggatg cctggtcaag ggctatttcc ctgagccagt gacagtgacc    900
aggtaccact gggaccctac ggaccagttc ccgataaagg gactcggtca ctgtcactgg    960
tggaactctg gatccctgtc cagcggtgtg cacaccttcc cagctgtcct gcagtctgac   1020
accttgagac ctaggacagg tcgccacac gtgtggaagg tcgacagga cgtcagactg     1080 ctctacactc tgagcagctc agtgactgtc ccctccagca cctggcccag cgagaccgtc   1140
gagatgtgag actcgtcgag tcactgacag ggaggtcgt ggaccgggtc gctctggcag    1200
acctgcaacg ttgcccaccc ggccagcagc accaaggtgg acaagaaaat tgtgcccagg   1260
tggacgttgc aacgggtggg ccggtcgtcg tggttccacc tgttctttta cacgggtcc    1320 gactcgggcg gtccgtccga aagagcgaa gaaataaatg aaaaagatct gcgaaaaaag    1380
ctgagcccgc caggcaggct cttctcgctt ctttatttac ttttttctaga cgcttttttc   1440 tctgagctcc aaggtaccgc cctaggcaat cttaagcaaa tttattatta taatagcaaa   1500
agactcgagt tccatggcg ggatccgtta gaattcgttt aaataataat attatcgttt    1560
gctataacta gcagcgaaaa gagtgcggat cagtttctca cgaatacttt gttatttaaa   1620
cgatattgat cgtcgctttt ctcacgccta gtcaaagagt gcttatgaaa caataaattt   1680
ggttttttca caggtcatcc atggtataac gacttactag tggatcttgg ttcaaccgcg   1740
ccaaaaaagt gtccagtagg taccatattg ctgaatgatc acctagaacc aagttggcgc   1800
gctactagcg aatatgaagg gagtagtgta gatctatatg gtgcttatta tggatatcaa   1860
cgatgatcgc ttatacttcc ctcatcacat ctagatatac cacgaataat acctatagtt   1920
tgtgctggag gcacaccaaa taaaacagca tgtatgtacg ggggtgtaac attacatgat   1980
acacgacctc cgtgtggttt attttgtcgt acatacatgc ccccacattg taatgtacta   2040
aataatcgat tgaccgaaga aaaaaagta ccaattaact tgtggataga cggaaaacaa    2100
ttattagcta actggcttct ttttttcat ggttaattga acacctatct gccttttgtt    2160
actacagtac ctatagataa agttaaaaca agcaaaaaag aagtaactgt tcaagagcta   2220
tgatgtcatg gatatctatt tcaattttgt tcgttttttc ttcattgaca agttctcgat   2280
gaccttcagg cgcgccatta tttacacgga aaatttggtt tatataactc agacagcttt   2340
ctggaagtcc gcgcggtaat aaatgtgcct tttaaaccaa atatattgag tctgtcgaaa   2400
ggcggtaagg tgcaaagagg cttgattgtg tttcattctt ctgaagggtc cacggtaagt   2460
ccgccattcc acgtttctcc gaactaacac aaagtaagaa gacttcccag gtgccattca   2520
tatgatttgt tgatgctcα agggcaatat ccagatacat tactccggat ttacagagat    2580
atactaaaca aactacgagt tcccgttata ggtctatgta atgaggccta aatgtctcta   2640
aataccacta tttcgtctac gagcctcagc attagcttgt atttgtacac aacttaagct   2700
ttatggtgat aaagcagatg ctcggagtcg taatcgaaca taaacatgtg ttgaattcga   2760
```

-continued

```
tggccgtata ggccacttta caaatacata cagggggtat taatttgaaa aagaccatgg    2820
accggcatat ccgtgaaat gtttatgtat gtccccata attaaacttt ttctggtacc    2880
cactcatcct tgcgtctatt cttgttttttt ctttggtaac caatgcatac gcgagtattg    2940
gtgagtagga acgcagataa aacaaaaaa gaaaccattg gttacgtatg cgctcataac    3000
tgatgaccca gactcccact agtctgcttg tttcagcagg agacagggtt accataacct    3060
actactgggt ctgagggtga tcagacgaac aaagtcgtcc tctgtcccaa tggtattgga    3120
gcaaggccag tcagagtgtg agtaatgatg tagcttggta ccaacagaag ccagggcagt    3180
cgttccggtc agtctcacac tcattactac atcgaaccat ggttgtcttc ggtcccgtca    3240
ctcctaagct gctcatatcc tatacatcca gtcgctacgc tggagtccct gatcgcttca    3300
gaggattcga cgagtatagg atatgtaggt cagcgatgcg acctcaggga ctagcgaagt    3360
gcggcagtgg gtacgggacg gatttcactc tgacgatatc cagtgtacag gctgaagacg    3420
cgccgtcacc catgccctgc ctaaagtgag actgctatag gtcacatgtc cgacttctgc    3480
cagcagttta tttctgtcag caagattata attctcctcc gacgttcggt ggaggcacca    3540
gtcgtcaaat aaagacagtc gttctaatat taagaggagg ctgcaagcca cctccgtggt    3600
agctggaaat caaacgggct gatgcggcgc caactgtatc catcttccca ccatccagtg    3660 tcgacccttta gtttgcccga ctacgccgcg gttgacatag gtagaagggt ggtaggtcac    3720
agcagttaac atctggaggt gcctcagtcg tgtgcttctt gaacaacttc taccccaaag    3780
tcgtcaattg tagacctcca cggagtcagc acacgaagaa cttgttgaag atggggttttc    3840 acatcaatgt caagtggaag attgatggca gtgaacgaca aaatggcgtc ctgaacagtt    3900
tgtagttaca gttcaccttc taactaccgt cacttgctgt tttaccgcag gacttgtcaa    3960
ggactgatca ggacagcaaa gacagcacct acagcatgag cagcaccctc acgttgacca    4020
cctgactagt cctgtcgttt ctgtcgtgga tgtcgtactc gtcgtgggag tgcaactggt    4080
aggacgagta tgaacgacat aacagctata cctgtgaggc cactcacaag acatcaactt    4140
tcctgctcat acttgctgta ttgtcgatat ggacactccg gtgagtgttc tgtagttgaa    4200
cacccattgt caagagcttc aaccgtaatg aggtgggtaa cagttctcga agttggcatt    4260
actc                                                                 4264
```

<210> SEQ ID NO 16
<211> LENGTH: 2132
<212> TYPE: DNA
<213> ORGANISM: Staphylococcus sp

<400> SEQUENCE: 16

```
gaggtccagc ttcagcagtc tggacctgac ctggtgaagc ctggggcttc agtgaagata     60
tcctgcaagg cttctggtta ctcattcact ggctactaca tgcactgggt gaagcagagc    120
ccgggaaaag gccttgagtg gattggacgt attaatccta caatggtgt tactctctac    180 aaccagaaat tcaaggacaa ggccacgtta actgtagaca gtcatccac cacagcctac    240 atggagctcc gcagcctgac atctgaggac tctgcggtct attactgtgc aagatctact    300
atgattacga actatgttat ggactactgg ggtcaaggga gtcagtcac cgtctcctca    360 gccaaaacga cacccccatc tgtctatcca ctggcccgg gatctgctgc ccaaactaac    420
tccatggtga ccctgggatg cctggtcaag ggctatttcc ctgagccagt gacagtgacc    480
tggaactctg gatccctgtc cagcggtgtg cacaccttcc cagctgtcct gcagtctgac    540
```

```
ctctacactc tgagcagctc agtgactgtc ccctccagca cctggcccag cgagaccgtc    600
acctgcaacg ttgcccaccc ggccagcagc accaaggtgg acaagaaaat tgtgcccagg    660
gactcgggcg gtccgtccga gaagagcgaa gaaataaatg aaaaagatct gcgaaaaaag    720
tctgagctcc aaggtaccgc cctaggcaat cttaagcaaa tttattatta taatagcaaa    780
gctataacta gcagcgaaaa gagtgcggat cagtttctca cgaatacttt gttatttaaa    840
ggttttttca caggtcatcc atggtataac gacttactag tggatcttgg ttcaaccgcg    900
gctactagcg aatatgaagg gagtagtgta gatctatatg gtgcttatta tggatatcaa    960
tgtgctggag gcacaccaaa taaaacagca tgtatgtacg ggggtgtaac attacatgat   1020
aataatcgat tgaccgaaga aaaaaagta ccaattaact tgtggataga cggaaaacaa    1080
actacagtac ctatagataa agttaaaaca agcaaaaaag aagtaactgt tcaagagcta   1140
gaccttcagg cgcgccatta tttacacgga aaatttggtt tatataactc agacagcttt   1200
ggcggtaagt tgcaaagagg cttgattgtg tttcattctt ctgaagggtc cacggtaagt   1260
tatgatttgt ttgatgctca agggcaatat ccagatacat tactccggat ttacagagat   1320
aataccacta tttcgtctac gagcctcagc attagcttgt atttgtacac aacttaagct   1380
tggccgtata ggccacttta caaatacata caggggtat taatttgaaa aagaccatgg    1440
cactcatcct tgcgtctatt cttgttttt ctttggtaac caatgcatac gcgagtattg    1500
tgatgaccca gactcccact agtctgcttg tttcagcagg agacagggtt accataacct   1560
gcaaggccag tcagagtgtg agtaatgatg tagcttggta ccaacagaag ccagggcagt   1620
ctcctaagct gctcatatcc tatacatcca gtcgctacgc tggagtccct gatcgcttca   1680
gcggcagtgg gtacgggacg gatttcactc tgacgatatc cagtgtacag gctgaagacg   1740
cagcagttta tttctgtcag caagattata attctcctcc gacgttcggt ggaggcacca   1800
agctggaaat caaacgggct gatgcggcgc caactgtatc catcttccca ccatccagtg   1860
agcagttaac atctggaggt gcctcagtcg tgtgcttctt gaacaacttc taccccaaag   1920
acatcaatgt caagtggaag attgatggca gtgaacgaca aaatggcgtc ctgaacagtt   1980
ggactgatca ggacagcaaa gacagcacct acagcatgag cagcaccctc acgttgacca   2040
aggacgagta tgaacgacat aacagctata cctgtgaggc cactcacaag acatcaactt   2100
cacccattgt caagagcttc aaccgtaatg ag                                 2132
```